United States Patent
Jorand-Lebrun et al.

(10) Patent No.: US 9,550,794 B2
(45) Date of Patent: Jan. 24, 2017

(54) MACROCYCLIC PYRIDAZINONE DERIVATIVES

(71) Applicant: Merck Patent GmbH, Darmstadt (DE)

(72) Inventors: Catherine Jorand-Lebrun, Contamine-Sarzin (FR); Santosh Kulkarni, Bangalore (IN); Serge Christmann-Franck, Geneva (CH)

(73) Assignee: MERCK PATENT GmbH, Darmstadt (DE)

( * ) Notice: Subject to any disclaimer, the term of this patent is extended or adjusted under 35 U.S.C. 154(b) by 0 days.

(21) Appl. No.: 14/766,291

(22) PCT Filed: Feb. 7, 2014

(86) PCT No.: PCT/EP2014/000337
§ 371 (c)(1),
(2) Date: Aug. 6, 2015

(87) PCT Pub. No.: WO2014/121942
PCT Pub. Date: Aug. 14, 2014

(65) Prior Publication Data
US 2015/0376206 A1    Dec. 31, 2015

(30) Foreign Application Priority Data

Feb. 7, 2013   (EP) .................................. 13154391

(51) Int. Cl.
| | | |
|---|---|---|
| *C07D 487/18* | (2006.01) | |
| *C07D 498/18* | (2006.01) | |
| *A61K 31/504* | (2006.01) | |
| *A61K 45/06* | (2006.01) | |
| *C07D 471/22* | (2006.01) | |
| *C07D 487/22* | (2006.01) | |

(52) U.S. Cl.
CPC ........... *C07D 498/18* (2013.01); *A61K 31/504* (2013.01); *A61K 45/06* (2013.01); *C07D 471/22* (2013.01); *C07D 487/18* (2013.01); *C07D 487/22* (2013.01)

(58) Field of Classification Search
CPC .................................................. C07D 487/18
See application file for complete search history.

(56) References Cited

U.S. PATENT DOCUMENTS

2006/0142292 A1    6/2006  Kyotani et al.

FOREIGN PATENT DOCUMENTS

EP     1 604 984 A1    12/2005

OTHER PUBLICATIONS

U.S. Appl. No. 14/766,671, filed Aug. 7, 2015, Jorand-Lebrun et al.
International Search Report Issued Mar. 27, 2014 in PCT/EP14/000337 Filed Feb. 7, 2014.

*Primary Examiner* — Bruck Kifle
(74) *Attorney, Agent, or Firm* — Oblon, McClelland, Maier & Neustadt, L.L.P.

(57) ABSTRACT

The present invention relates to compounds of formula (I) Wherein R1, R2, R3, R4, L and Z have the meaning given in claim 1, and their use in the prophylaxis and treatment of diseases.

10 Claims, No Drawings

MACROCYCLIC PYRIDAZINONE DERIVATIVES

The present invention provides Macrocyclic Pyridazinone derivatives of Formula (I) as IRAK inhibitors and their use in the treatment of cancer, and other diseases related to IRAK overexpression, like rheumatoid arthritis, systemic lupus erythematosus or lupus nephritis.

BACKGROUND

Kinases catalyze the phosphorylation of proteins, lipids, sugars, nucleosides and other cellular metabolites and play key roles in all aspects of eukaryotic cell physiology. Especially, protein kinases and lipid kinases participate in the signaling events which control the activation, growth, differentiation and survival of cells in response to extracellular mediators or stimuli such as growth factors, cytokines or chemokines. In general, protein kinases are classified in two groups, those that preferentially phosphorylate tyrosine residues and those that preferentially phosphorylate serine and/or threonine residues.

Kinases are important therapeutic targets for the development of anti-inflammatory drugs (Cohen, 2009. Current Opinion in Cell Biology 21, 1-8), for example kinases that are involved in the orchestration of adaptive and innate immune responses. Kinase targets of particular interest are members of the IRAK family.

The interleukin-1 receptor-associated kinases (IRAKs) are critically involved in the regulation of intracellular signaling networks controlling inflammation (Ringwood and Li, 2008. Cytokine 42, 1-7). IRAKs are expressed in many cell types and can mediate signals from various cell receptors including toll-like receptors (TLRs). IRAK4 is thought to be the initial protein kinase activated downstream of the interleukin-1 (IL-1) receptor and all toll-like-receptors (TLRs) except TLR3, and initiates signaling in the innate immune system via the rapid activation of IRAK1 and slower activation of IRAK2. IRAK1 was first identified through biochemical purification of the IL-1 dependent kinase activity that co-immunoprecipitates with the IL-1 type 1 receptor (Cao et al., 1996. Science 271(5252): 1128-31). IRAK2 was identified by the search of the human expressed sequence tag (EST) database for sequences homologous to IRAKI (Muzio et al., 1997. Science 278 (5343): 1612-5). IRAK3 (also called IRAKM) was identified using a murine EST sequence encoding a polypeptide with significant homology to IRAK1 to screen a human phytohaemagglutinin-activated peripheral blood leukocyte (PBL) cDNA library (Wesche et al., 1999. J. Biol. Chem. 274(27): 19403-10). IRAK4 was identified by database searching for IRAK-like sequences and PCR of a universal cDNA library (Li et al., 2002. Proc. Natl. Acad. Sci. USA 99(8):5567-5572).

Mice that express a catalytically inactive mutant of IRAK4 instead of the wild-type kinase are completely resistant to septic shock triggered by several TLR agonists and are impaired in their response to IL-1. Children who lack IRAK4 activity due to a genetic defect suffer from recurring infection by pyogenic bacteria. It appears that IRAK-dependent TLRs and IL-1Rs are vital for childhood immunity against some pyogenic bacteria but play a redundant role in protective immunity to most infections in adults. Therefore IRAK4 inhibitors may be useful for the treatment of chronic inflammatory diseases in adults without making them too susceptible to bacterial and viral infections (Cohen, 2009. Current Opinion in Cell Biology 21, 1-8). Potent IRAK4 inhibitors have been developed (Buckley et al., 2008. Bioorg Med Chem Lett. 18(12):3656-60). IRAK1 is essential for the TLR7-mediated and TLR9-mediated activation of IRF7 and the production of interferon-alpha (IFN-α) suggesting that IRAK1 inhibitors may be useful for the treatment of Systemic lupus erythematosus (SLE). IRAK2 is activated downstream of IRAK4 and plays a role in proinflammatory cytokine production. Therefore IRAK2 inhibitors may be useful for inflammatory diseases.

SUMMARY OF THE INVENTION

According to one aspect of the invention, are provided compounds of Formula (I).

According to another aspect of the invention, are provided compounds of Formula (I) which are suitable for the treatment and/or prevention of disorders related to IRAK.

According to another aspect of the invention, are provided compounds, which are able to modulate, especially inhibit the activity or function of IRAK in disease states in mammals, especially in humans.

According to another aspect of the invention, are provided methods for the treatment and/or prevention of disorders selected from auto-immune, inflammatory disorders, cardiovascular diseases, neurodegenerative disorders, bacterial and viral infections, allergy, asthma, pancreatitis, multi-organ failure, kidney diseases, platelet aggregation, cancer, transplantation, sperm motility, erythrocyte deficiency, graft rejection, lung injuries, respiratory diseases and ischemic conditions.

According to another aspect, the present invention provides compounds of Formula (I), which are selective of IRAK-4 and/or IRAK-1.

According to another aspect of the invention is provided a kit or a set comprising at least one compound of Formula (I), preferably in combination with immunomodulating agents.

Preferably, the kit consists of separate packs of:
(a) an effective amount of a compound of the formula (I) and/or pharmaceutically usable derivatives or tautomers, solvates, salts, hydrates and stereoisomers thereof, including mixtures thereof in all ratios, and
(b) an effective amount of a further medicament active ingredient.

According to another aspect of the invention, is provided a process for the synthesis of compounds of formula (I) and related formula.

DETAILED DESCRIPTION OF THE INVENTION

In one embodiment, the present invention provides a compound of formula (I)

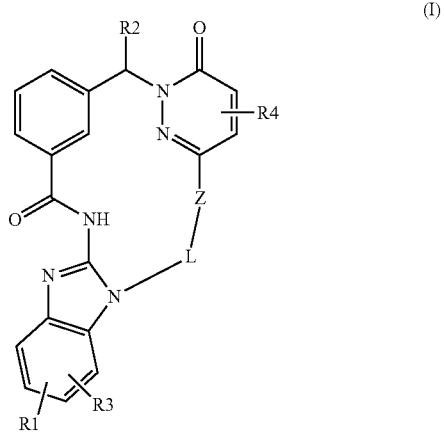

wherein
R1, R3 denote each, independently of one another H, $(CH_2)_p CON(R5)_2$, OA, Hal, COOH, COOA, $(CH_2)_p NHCOA$, $(CH_2)_p Het1$, $(CH_2)_p NR2R5$, or OH;
R2 denotes H or linear or branched alkyl with 1, 2 or 3 C atoms, wherein one or two H atoms of the alkyl group may be replaced by OR6, NR5R6, NHCOR5, CONR5R6;
R4 denotes H or A;
R5 denotes H or linear or branched alkyl with 1, 2 or 3 C atoms;
R6 denotes H or linear or branched alkyl with 1, 2 or 3 C atoms;
Z is absent or Ar-diyl or Het-diyl;
L denotes $(CH_2)_n$ wherein one or two $CH_2$ groups may be replaced by O and/or a CH=CH-group, and/or wherein one or two H atoms may be replaced by OR2, NR2R5 or Het1;
Ar-diyl denotes 1,2-, 1,3- or 1,4-phenylen optionally substituted with from 1 to 5 groups independently selected from Hal, CN, —$CF_3$, —$OCF_3$, OH, OA, $SO_2$-A, COOH, COOA, —CO-A, O-phenyl, $SO_2$-phenyl, $SO_2$—$CF_3$, Het2 and/or A;
Het-diyl denotes an unsaturated, saturated or aromatic 5- or 6-membered heterocycle having 1 to 2 N, O and/or S atoms, which may be unsubstituted or mono-, di- or trisubstituted by Hal, CN, —$CF_3$, —$OCF_3$, OA, $SO_2$-A, COOH, COOA, —CO-A, O-phenyl, $SO_2$-phenyl, $SO_2$—$CF_3$, Het2 and/or A;
A denotes an unbranched or branched alkyl having 1 to 10 C atoms, in which 1 to 5 H atoms may be replaced by F and/or in which one or two non-adjacent $CH_2$ groups may be replaced by O;
Het1 denotes morpholinyl, piperidinyl or pyrrolidinyl;
Het2 denotes morpholinyl, piperidinyl or pyrrolidinyl;
Hal denotes F, Cl, Br, I;
n denotes 1, 2, 3, 4, 5 or 6;
p denotes 0, 1 or 2;
and pharmaceutically usable tautomers, solvates, salts and stereoisomers thereof, including mixtures thereof in all ratios.

The present invention includes in particular tautomeric form (I'):

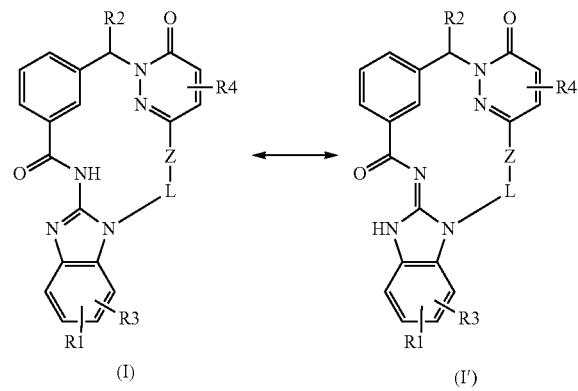

In case R2 is alkyl, the carbon atom which carries R2 may have an absolute stereo configuration being R or S.

R2 preferably denotes H or linear or branched alkyl with 1, 2 or 3 C atoms, wherein one or two (most preferably one) of the H atoms may be replaced by OR6, NR5R6, NHCOR5, CONR5R6, wherein R5 and R6, independently from one another, denote preferably H, methyl, ethyl, n-propyl or isopropyl.

R3 preferably denotes H or $(CH_2)_p CON(R5)_2$, OA, F, Cl, COOH, COOA, $(CH_2)_p NHCOA$, $(CH_2)_p Het1$, $(CH_2)_p NR2R5$, or OH, wherein A denotes methyl, ethyl, propyl, isopropyl, butyl, isobutyl, sec-butyl or tert-butyl, pentyl, 1-, 2- or 3-methylbutyl, 1,1-, 1,2- or 2,2-dimethylpropyl, 1-ethylpropyl or hexyl in which 1 to 5 H atoms may be replaced by F and/or in which one or two non-adjacent $CH_2$ groups may be replaced by O, A most preferably denotes methyl, ethyl, propyl, isopropyl in which 1 to 5 H atoms may be replaced by F. Most preferably R3 denotes $(CH_2)_2 NR5R6$, $(CH_2)_2 OR5$, $(CH_2)_2 NHCOCH3$, $(CH_2)_2 CONR5R6$ or OH, wherein R5 and R6, independently from one another, denote preferably H, methyl, ethyl, n-propyl or isopropyl.

In particular preferred embodiments R4 is H or methyl.

Het-diyl preferably denotes pyridine-diyl, pyrimidine-diyl, pyridazin-diyl, pyrazol-diyl, imidazol-diyl, piperidin-diyl or pyrrolidin-diyl, each of which is unsubstituted or mono- or disubstituted by A.

Alkyl particularly denotes methyl, ethyl, n-propyl or isopropyl.

In other preferred embodiments R3 is H and R1 denotes $(CH_2)_p CON(R5)_2$, OA, Hal, COOH, COOA, $(CH_2)_p NHCOA$, $(CH_2)_p Het1$, $(CH_2)_p NR5R6$, or OH. In these embodiments A preferably denotes methyl, ethyl, propyl, isopropyl, butyl, isobutyl, sec-butyl or tert-butyl, pentyl, 1-, 2- or 3-methylbutyl, 1,1-, 1,2- or 2,2-dimethylpropyl, 1-ethylpropyl or hexyl in which 1 to 5 H atoms may be replaced by F and/or in which one or two non-adjacent $CH_2$ groups may be replaced by O, A most preferably denotes methyl, ethyl, propyl, isopropyl in which 1 to 5 H atoms may be replaced by F.

In case neither R1 nor R3 is H, R1 and R3 are preferably the same groups (e.g. R1=R3=$(CH_2)_p CON(R5)_2$, OA, Hal, COOH, COOA, $(CH_2)_p NHCOA$, $(CH_2)_p Het1$, $(CH_2)_p NH_2$, or OH). In such cases A most preferably denotes methyl, ethyl, propyl, isopropyl, butyl, isobutyl, sec-butyl or tert-butyl, pentyl, 1-, 2- or 3-methylbutyl, 1,1-, 1,2- or 2,2-dimethylpropyl, 1-ethylpropyl or hexyl, most preferably methyl, ethyl, propyl, isopropyl in which 1 to 5 H atoms may be replaced by F and/or in which one or two non-adjacent $CH_2$ groups may be replaced by O, A most preferably denotes methyl, ethyl, propyl, isopropyl in which 1 to 5 H atoms may be replaced by F.

In case Z is absent, n is preferably 4, 5 or 6. In case Z is not absent, n preferably denotes 1 or 2. In preferred embodiments in which Z is absent, one $CH_2$ group of L is replaced by O and one H atom of L is replaced by OH. In another embodiment one $CH_2$ group of L is replaced by O and another $CH_2$ group of L is replaced by a CH=CH-group.

Z preferably denotes 1,3-phenylen, which is unsubstituted or monosubstituted by A, Hal, OH, or OA. In such cases A most preferably denotes methyl, ethyl, propyl, isopropyl, butyl, isobutyl, sec-butyl or tert-butyl, pentyl, 1-, 2- or 3-methylbutyl, 1,1-, 1,2- or 2,2-dimethylpropyl, 1-ethylpropyl or hexyl, most preferably methyl, ethyl, propyl, isopropyl in which 1 to 5 H atoms may be replaced by F and/or in which one or two non-adjacent $CH_2$ groups may be replaced by O. And most preferably A denotes methyl, ethyl, propyl, isopropyl in which 1 to 5 H atoms may be replaced by F.

A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

In particular preferred embodiment R4 is H or methyl, Het-diyl denotes pyridine-diyl, pyrimidine-diyl, pyridazin-diyl, pyrazol-diyl, imidazol-diyl, piperidin-diyl or pyrrolidin-diyl, each of which is unsubstituted or mono- or disubstituted by A, and n of group L denotes 1 or 2. Furthermore, in these embodiments A most preferably denotes methyl, ethyl, propyl, isopropyl, butyl, isobutyl, sec-butyl or tert-butyl, pentyl, 1-, 2- or 3-methylbutyl, 1,1-, 1,2- or 2,2-dimethylpropyl, 1-ethylpropyl or hexyl, most preferably methyl, ethyl, propyl, isopropyl in which 1 to 5 H atoms may be replaced by F and/or in which one or two non-adjacent $CH_2$ groups may be replaced by O. And most preferably A denotes methyl, ethyl, propyl, isopropyl in which 1 to 5 H atoms may be replaced by F.

In another preferred embodiment R4 is H or methyl, Z denotes 1,3-phenylen, which is unsubstituted or monosubstituted by A, Hal, OH, or OA and n of group L denotes 1 or 2. Furthermore, also in these embodiments A most preferably denotes methyl, ethyl, propyl, isopropyl, butyl, isobutyl, sec-butyl or tert-butyl, pentyl, 1-, 2- or 3-methylbutyl, 1,1-, 1,2- or 2,2-dimethylpropyl, 1-ethylpropyl or hexyl, most preferably methyl, ethyl, propyl, isopropyl in which 1 to 5 H atoms may be replaced by F and/or in which one or two non-adjacent $CH_2$ groups may be replaced by O. And most preferably A denotes methyl, ethyl, propyl, isopropyl in which 1 to 5 H atoms may be replaced by F.

Compounds according to formula (I) in which R2 is H or linear or branched alkyl with 1, 2 or 3 C atoms, wherein one or two (most preferably one) of the H atoms may be replaced by $(CH_2)_2NR5R6$, $(CH_2)_2OR5$, $(CH_2)_2NHCOCH_3$ or $(CH_2)_2CONR5R6$ and R4 is H or methyl, R1 denotes H and $R^3$ denotes $(CH_2)_pCON(R5)_2$, OA, Hal, COOH, COOA, $(CH_2)_pNHCOA$, $(CH_2)_pHet1$, $(CH_2)_pNR5R6$, or OH, Het-diyl denotes pyridine-diyl, pyrimidine-diyl, pyridazin-diyl, pyrazol-diyl, imidazol-diyl, piperidin-diyl or pyrrolidin-diyl, each of which is unsubstituted or mono- or disubstituted by A and n of group L denotes 1 or 2. In such cases A most preferably denotes methyl, ethyl, propyl, isopropyl, butyl, isobutyl, sec-butyl or tert-butyl, pentyl, 1-, 2- or 3-methylbutyl, 1,1-, 1,2- or 2,2-dimethylpropyl, 1-ethylpropyl or hexyl, most preferably methyl, ethyl, propyl, isopropyl in which 1 to 5 H atoms may be replaced by F and/or in which one or two non-adjacent $CH_2$ groups may be replaced by O. And most preferably A denotes methyl, ethyl, propyl, isopropyl in which 1 to 5 H atoms may be replaced by F.

The invention also relates in particular to compounds according to formula (I) in which R4 is H or methyl, R1 denotes H and $R^3$ denotes $(CH_2)_pCON(R5)_2$, OA, Hal, COOH, COOA, $(CH_2)_pNHCOA$, $(CH_2)_pHet1$, $(CH_2)_pNR5R6$, or OH, Z denotes 1,3-phenylen, which is unsubstituted or monosubstituted by A, Hal, OH, or OA and n of group L denotes 1 or 2. In such cases again A most preferably denotes methyl, ethyl, propyl, isopropyl, butyl, isobutyl, sec-butyl or tert-butyl, pentyl, 1-, 2- or 3-methylbutyl, 1,1-, 1,2- or 2,2-dimethylpropyl, 1-ethylpropyl or hexyl, most preferably methyl, ethyl, propyl, isopropyl in which 1 to 5 H atoms may be replaced by F and/or in which one or two non-adjacent $CH_2$ groups may be replaced by O. And most preferably A denotes methyl, ethyl, propyl, isopropyl in which 1 to 5 H atoms may be replaced by F.

In another preferred embodiment, the present invention provides following compound

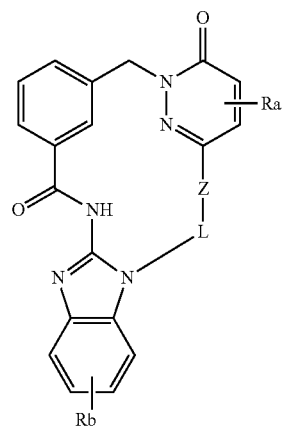

wherein
Ra, Rb denote each independently H, Hal or X,
Z is Ar or Het,
L is alkylen or alkoxyalkylene having 1 to 4 C-atoms
Ar denotes 1,2-, 1,3- or 1,4-phenylen optionally substituted with from 1 to 5 groups independently selected from Hal, CN, —$CF_3$, —$OCF_3$, OH (to include ex. 12), O-alkyl, $SO_2$-alkyl, COOR, —CO-alkyl, O-phenyl, $SO_2$-phenyl, $SO_2$—$CF_3$, O—$(CH_2)_n$-alkyl, X,
R denotes H or a linear or branched alkyl having 1 to 12 C-atoms,
Het denotes a monocyclic 5-8-membered divalent ring being saturated, unsaturated or aromatic, containing 1 to 3 heteroatoms independently selected from N, O and S, and or a group CO, and optionally substituted with from 1 to 5 groups independently selected from Hal, CN, —$CF_3$, —$OCF_3$, O-alkyl, $SO_2$-alkyl, COOR, —CO-alkyl, O-phenyl, $SO_2$-phenyl, $SO_2$—$CF_3$, O—$(CH_2)_n$-alkyl, X,
X is branched or linear alkyl having 1 to 12 C-atoms, wherein one or more, such as 1 to 7, H atoms may be replaced by Hal, OR, COOR, CN or $NR_2$ and wherein one or more, preferably 1 to 5 $CH_2$-groups may be replaced by O, CO, NR or S, SO, $SO_2$, 1,2-, 1,3- or 1,4-phenylen, —CH═CH— or —C≡C—,
and
Hal denotes F, Cl, Br, I
and pharmaceutically usable derivatives, solvates, salts and stereoisomers thereof, including mixtures thereof in all ratios.

The present invention includes in particular tautomeric form:

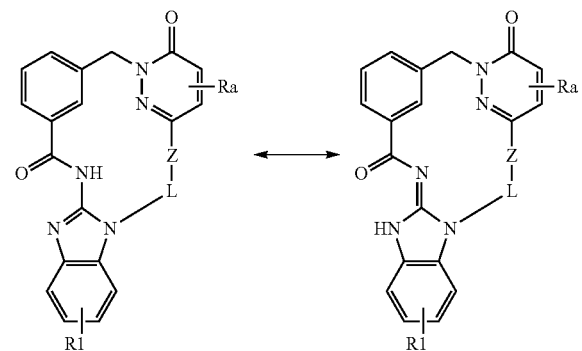

If not indicated otherwise, alkyl denotes a carbon chain having 1 to 12 carbon atoms, preferably 1 to 8 carbon atoms and most preferably 1 to 6 carbon atoms. Alkyl very preferably denotes methyl, furthermore ethyl, propyl, isopropyl, butyl, isobutyl, sec-butyl or tert-butyl, furthermore also pentyl, 1, 2 or 3 methylbutyl, 1,1, 1,2- or 2,2-dimethylpropyl, 1-ethylpropyl, hexyl, 1, 2, 3 or 4 methylpentyl, 1,1, 1,2, 1,3, 2,2, 2,3- or 3,3-dimethylbutyl, 1 or 2 ethylbutyl, 1 ethyl-1-methylpropyl, 1 ethyl-2-methylpropyl, 1,1,2- or 1,2,2-trimethylpropyl.

The group Oalkyl preferably denotes methoxy and ethoxy.

Ar preferably denotes 1,3-phenylene, which may be unsubstituted or monosubstituted, disubstituted or trisubstituted by a substitutent selected from a group mentioned under the definition of Ar. Most preferably Ar is unsubstituted or substituted by alkyl, Hal or CN.

R is preferably methyl, ethyl, n-propyl or n-butyl.

Ra is preferably H, Hal, Oalkyl or alkyl.

Rb denotes preferably H, alkyl, Hal, Oalkyl or $(CH_2)_n$CONHR or $(CH_2)_n$COOR, wherein n is 0, 1, 2, 3, 4, 5, or 6 and R is as defined above.

Z is preferably Ar and most preferably 1,3-phenylen.

L is preferably $(CH_2)_n$ or $(CH_2)_nO(CH_2)_n$ or $(CH_2)_nO$, wherein n is 0, 1, 2, 3, 4, 5, or 6. In another preferred embodiment L is alkylen, wherein one H atom is replaced by OH.

Het preferably denotes, not withstanding further substitutions, for example, a divalent pyrimidine or pyridine group.

Above and below, all radicals and indices have the meaning indicated under the generic structural formula, unless expressly stated otherwise.

Generally, compounds of formula I are the more preferred, the more preferred substituents they carry.

Throughout the invention, all radicals which occur more than once may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above.

Preferred compounds No. 1 to 42 of formula (I) are given below together with their activities ($IC_{50}$ values were obtained according to the IRAK 1 and IRAK 4 enzymatic assays described in Example 42):

| Compound No. | Structure | $IC_{50}$ IRAK1 | $IC_{50}$ IRAK4 |
|---|---|---|---|
| 1 | 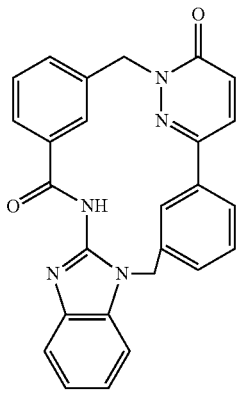 [SMILES: O=C1Nc2nc3ccccc3n2Cc2cccc(c2)-c2ccc(=O)n(n2)Cc2cccc1c2] | * | * |
| 2 | 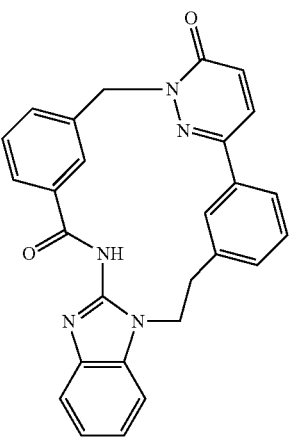 [SMILES: O=C1Nc2nc3ccccc3n2CCc2cccc(c2)-c2ccc(=O)n(n2)Cc2cccc1c2] | * | * |
| 3a | 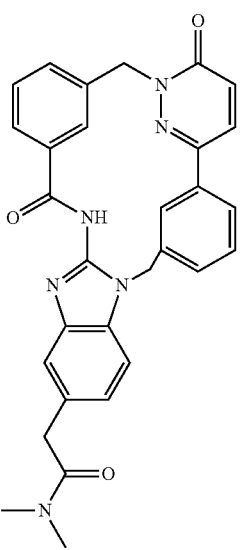 [SMILES: CN(C)C(=O)Cc1ccc2c(c1)nc1n2Cc2cccc(c2)-c2ccc(=O)n(n2)Cc2cccc(c2)C(=O)N1] | * | * |
| 4 | 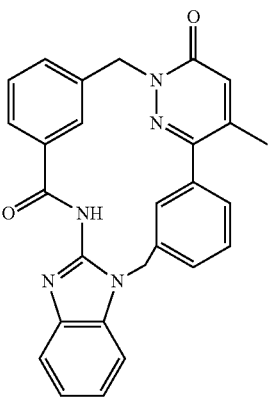 [SMILES: Cc1ccc2cc1-c1ccc(=O)n(n1)Cc1cccc(c1)C(=O)Nc1nc3ccccc3n1C2] | * |  |

| Compound No. | Structure | IC$_{50}$ IRAK1 | IC$_{50}$ IRAK4 |
|---|---|---|---|
| 3b | 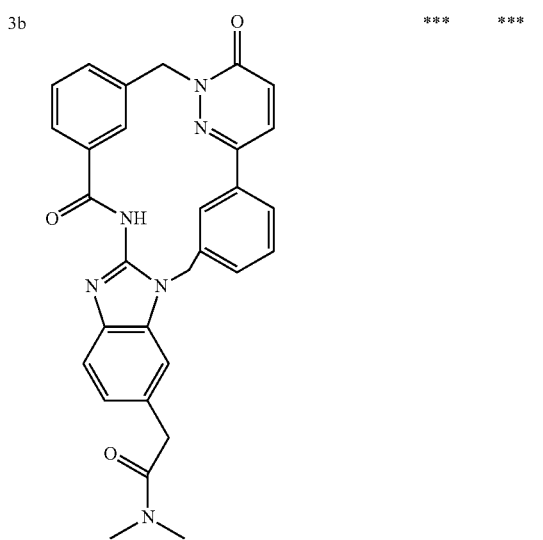 | * | * |
| 5 | 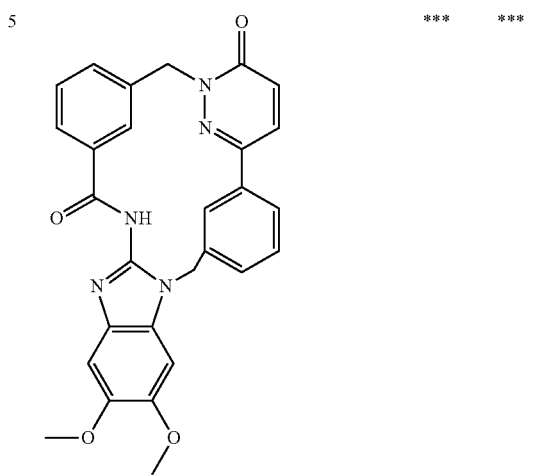 | * | * |
| 6 | 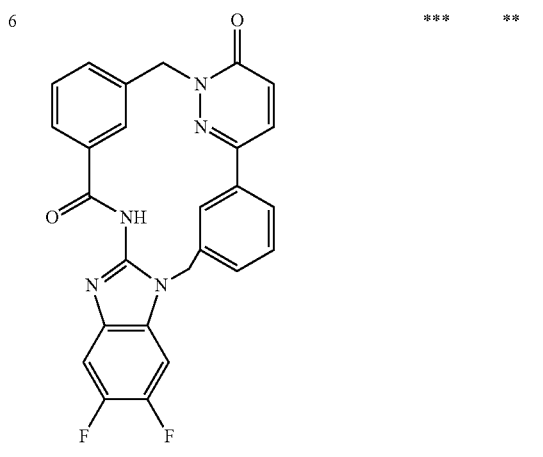 | * |  |
| Compound No. | Structure | IC$_{50}$ IRAK1 | IC$_{50}$ IRAK4 |
|---|---|---|---|
| 7 | 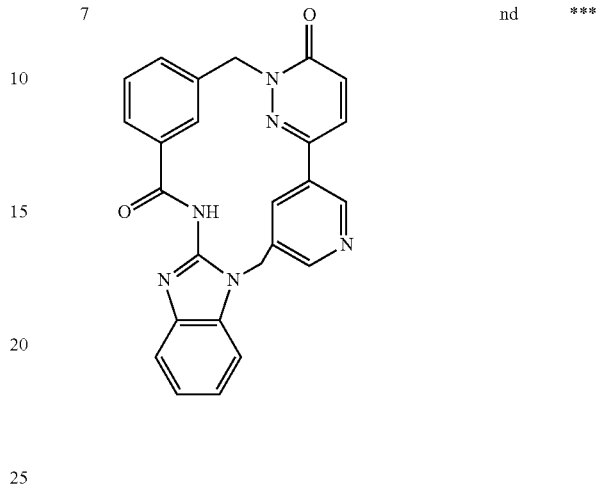 | nd | *** |
| 8 | 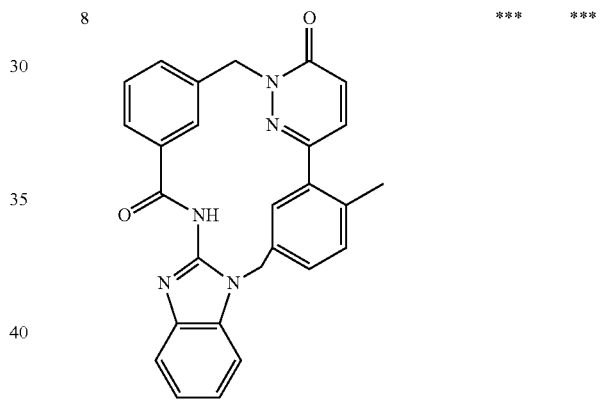 | * | * |
| 9 | 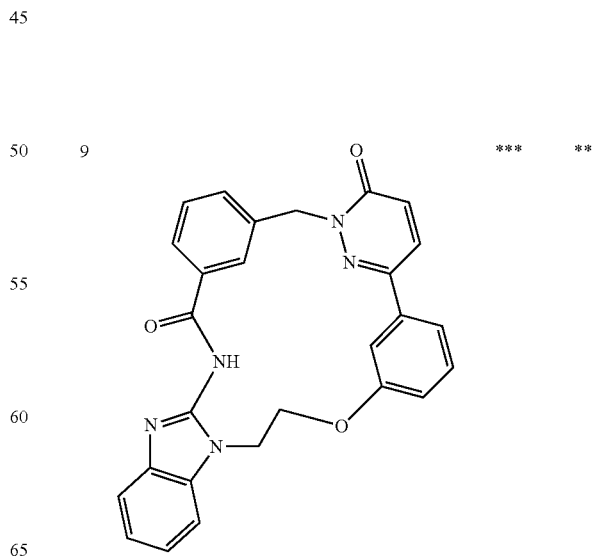 | * |  |

-continued
| Compound No. | Structure | IC$_{50}$ IRAK1 | IC$_{50}$ IRAK4 |
|---|---|---|---|
| 10 | 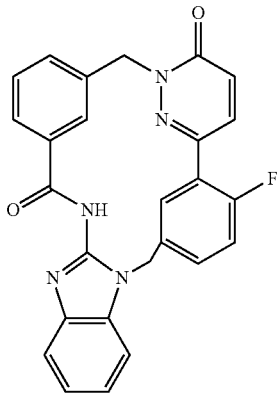 [SMILES: O=C1Nc2nc3ccccc3n2Cc2ccc(F)c(c2)-c2ccc(=O)n(n2)Cc2cccc1c2] | * |  |
| 11 | 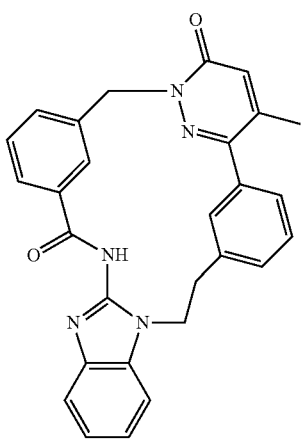 [SMILES: Cc1cc(=O)n2nc1-c1cccc(c1)CCn1c(nc3ccccc31)NC(=O)c1cccc(c1)C2] | * | * |
| 12 | 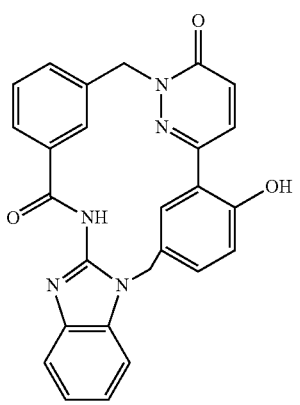 [SMILES: O=C1Nc2nc3ccccc3n2Cc2ccc(O)c(c2)-c2ccc(=O)n(n2)Cc2cccc1c2] | * | * |
-continued
| Compound No. | Structure | IC$_{50}$ IRAK1 | IC$_{50}$ IRAK4 |
|---|---|---|---|
| 13 | 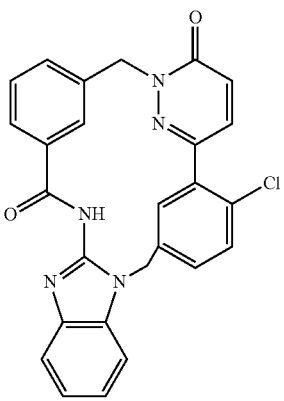 [SMILES: O=C1Nc2nc3ccccc3n2Cc2ccc(Cl)c(c2)-c2ccc(=O)n(n2)Cc2cccc1c2] | * |  |
| 14 | 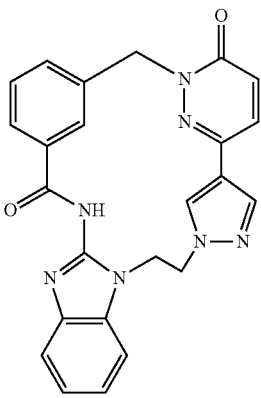 [SMILES: O=C1Nc2nc3ccccc3n2CCn2cc(cn2)-c2ccc(=O)n(n2)Cc2cccc1c2] | * | * |
| 15 | 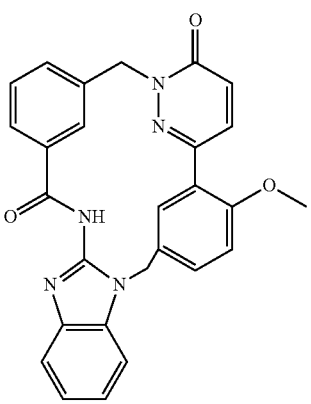 [SMILES: COc1ccc2cc1-c1ccc(=O)n(n1)Cc1cccc(c1)C(=O)Nc1nc3ccccc3n1C2] | * | * |

-continued

| Compound No. | Structure | IC$_{50}$ IRAK1 | IC$_{50}$ IRAK4 |
|---|---|---|---|
| 16 | | *** | *** |
| 17 | | *** | *** |
| 18 | | *** | *** |
| 19 | | ** | *** |
| 20 | | *** | *** |
| 21 | | *** | *** |

-continued
| Compound No. | Structure | IC50 IRAK1 | IC50 IRAK4 |
|---|---|---|---|
| 22 | 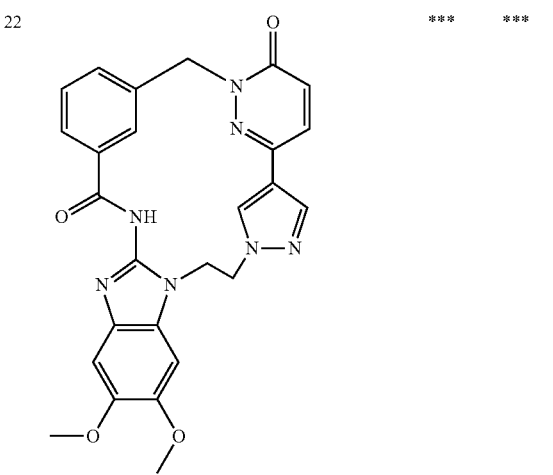 | * | * |
| 23 | 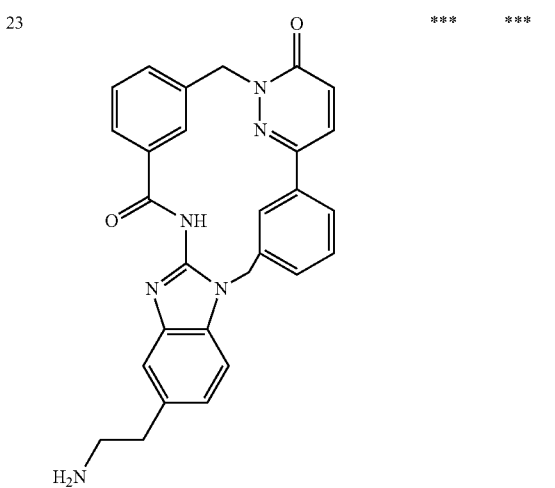 | * | * |
| 24 | 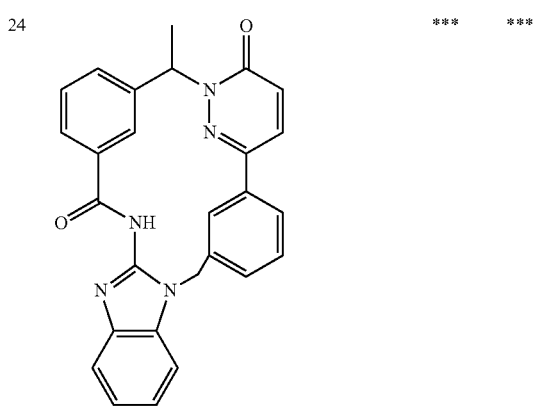 | * | * |
-continued
| Compound No. | Structure | IC50 IRAK1 | IC50 IRAK4 |
|---|---|---|---|
| 25 | 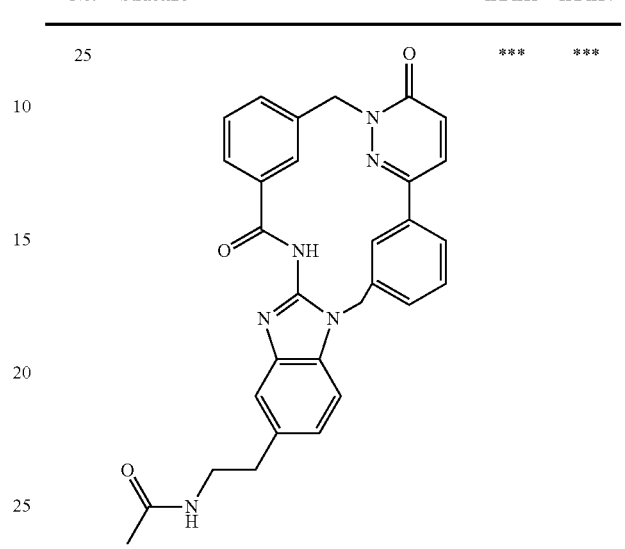 | * | * |
| 26 | | * | * |
| 27 | | *** | *** |
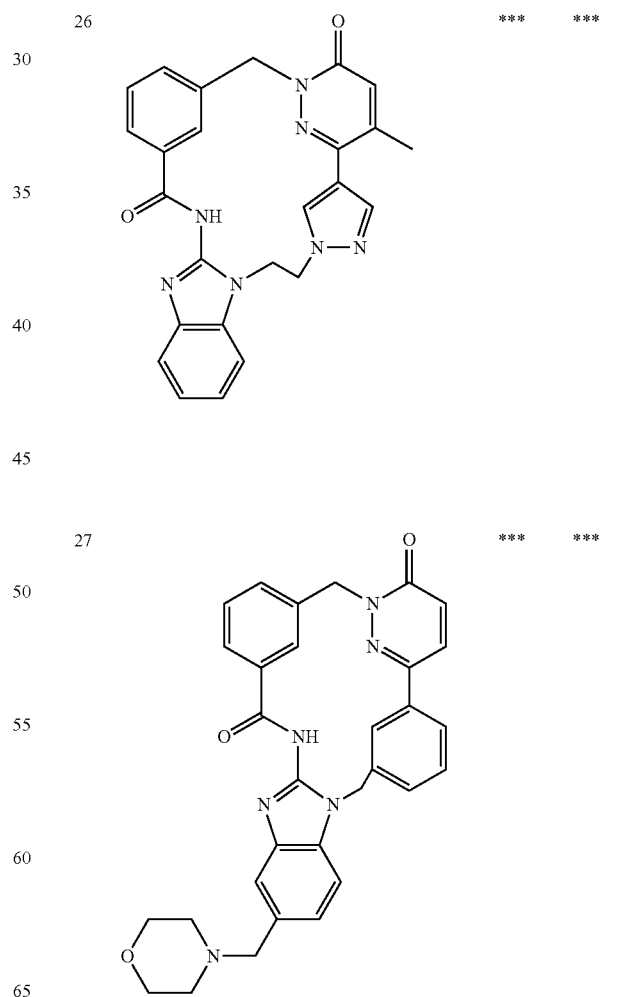

-continued
| Compound No. | Structure | IC50 IRAK1 | IC50 IRAK4 |
|---|---|---|---|
| 28 | 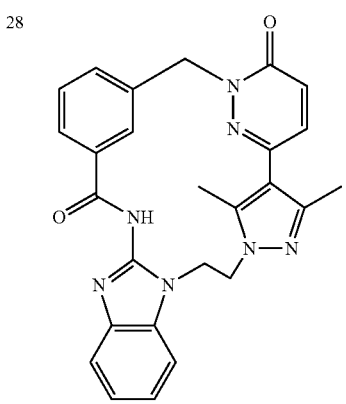 |  |  |
| 29 | 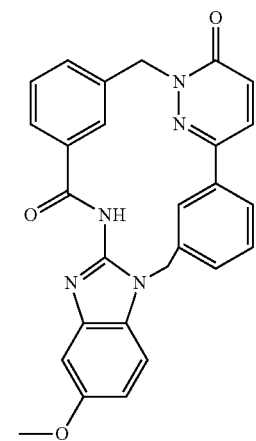 [SMILES: COc1ccc2c(c1)nc1n2Cc2cccc(c2)-c2ccc(=O)n(n2)Cc2cccc(c2)C(=O)N1] | * | * |
| 30 | 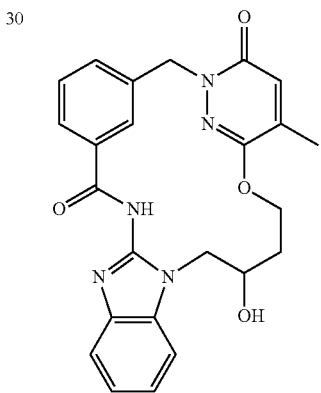 | * | * |
-continued
| Compound No. | Structure | IC50 IRAK1 | IC50 IRAK4 |
|---|---|---|---|
| 31 | 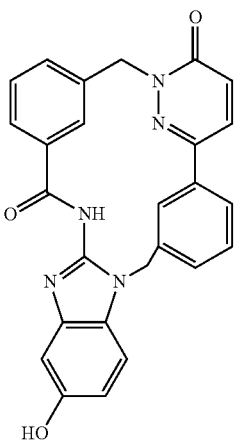 [SMILES: O=C1Nc2nc3cc(O)ccc3n2Cc2cccc(c2)-c2ccc(=O)n(n2)Cc2cccc1c2] | * |  |
| 32a | 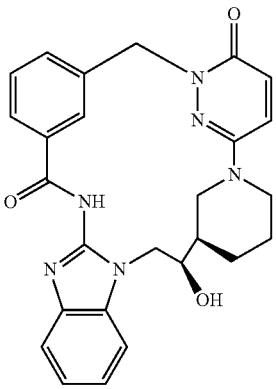 [SMILES: O=C1Nc2nc3ccccc3n2C[C@H](O)[C@@H]2CCCN(C2)c2ccc(=O)n(n2)Cc2cccc1c2] | * | * |
| 32b | 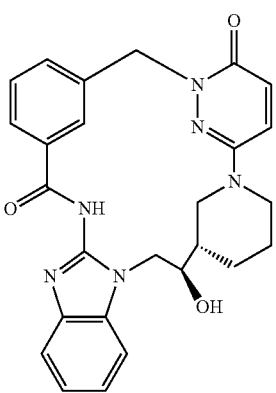 [SMILES: O=C1Nc2nc3ccccc3n2C[C@H](O)[C@H]2CCCN(C2)c2ccc(=O)n(n2)Cc2cccc1c2] | * | * |

-continued
| Compound No. | Structure | IC50 IRAK1 | IC50 IRAK4 |
|---|---|---|---|
| 33 | 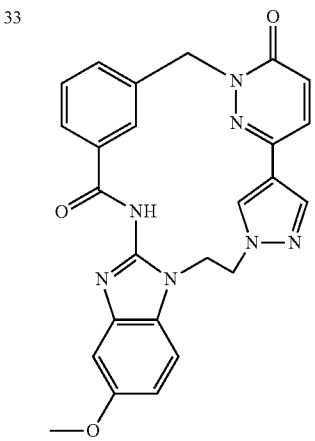 | * | * |
| 34 | 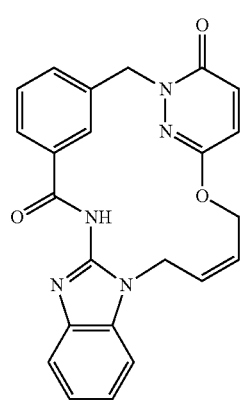 [SMILES: O=C1Nc2nc3ccccc3n2C/C=C\COc2ccc(=O)n(n2)Cc2cccc1c2] | * | * |
| 35 | 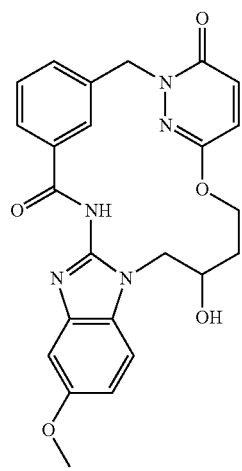 [SMILES: COc1ccc2c(c1)nc1n2CC(O)CCOc2ccc(=O)n(n2)Cc2cccc(c2)C(=O)N1] | * | * |
-continued
| Compound No. | Structure | IC50 IRAK1 | IC50 IRAK4 |
|---|---|---|---|
| 36a | 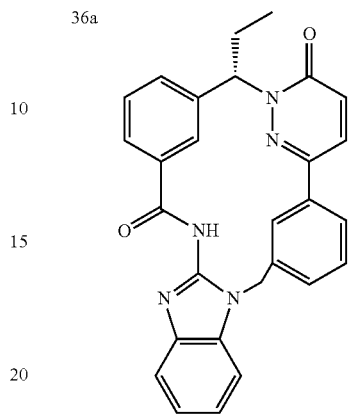 | * | * |
| 36b | | * |  |
| 37 | | *** | *** |

-continued

| Compound No. | Structure | IC$_{50}$ IRAK1 | IC$_{50}$ IRAK4 |
|---|---|---|---|
| 38 | | *** | *** |
| 39 | 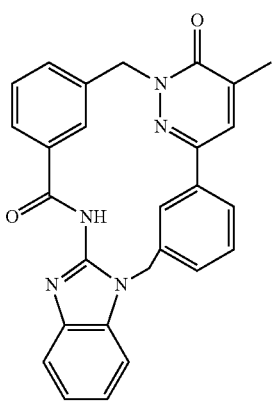 [SMILES: Cc1cc2nn(c1=O)Cc1cccc(c1)C(=O)Nc1nc3ccccc3n1Cc1cccc-2c1] | nd | nd |
| 40 | 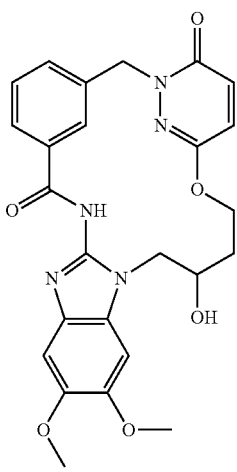 [SMILES: COc1cc2nc3n(c2cc1OC)CC(O)CCOc1ccc(=O)n(n1)Cc1cccc(c1)C(=O)N3] | nd | nd |

-continued

| Compound No. | Structure | IC$_{50}$ IRAK1 | IC$_{50}$ IRAK4 |
|---|---|---|---|
| 41 | 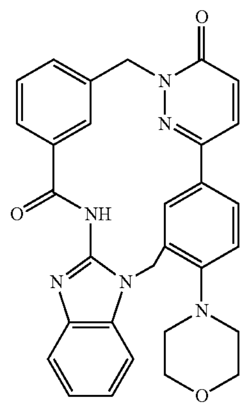 [SMILES: O=C1Nc2nc3ccccc3n2Cc2cc(ccc2N2CCOCC2)-c2ccc(=O)n(n2)Cc2cccc1c2] | nd | nd |
| 42 | 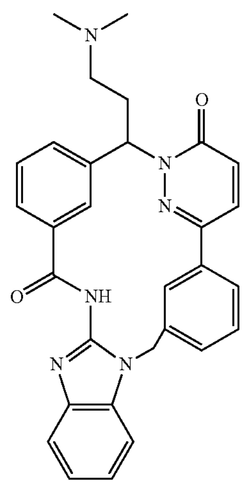 [SMILES: CN(C)CCC1c2cccc(c2)C(=O)Nc2nc3ccccc3n2Cc2cccc(c2)-c2ccc(=O)n1n2] | nd | nd |

\*: 1 µM < IC$_{50}$ < 5 µM
\*\*: 0.1 µM < IC$_{50}$ < 1 µM
\*\*\*: IC$_{50}$ < 0.1 µM
n.d: not determined Pharmaceutical Salts and Other Forms The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphor-sulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese (III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethyl-aminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanol-amine, triethylamine, trimethylamine, tripropylamine and tris(hydroxymethyl)-methylamine (tromethamine), but this is not intended to represent a restriction.

Compounds of the present invention which contain basic nitrogen-containing groups can be quaternised using agents such as $(C_1$-$C_4)$alkyl halides, for example methyl, ethyl, isopropyl and tert-butyl chloride, bromide and iodide; di($C_1$-$C_4$)alkyl sulfates, for example dimethyl, diethyl and diamyl sulfate; $(C_{10}$-$C_{18})$alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

Particular preference is given to hydrochloride, dihydrochloride, hydrobromide, maleate, mesylate, phosphate, sulfate and succinate.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The following abbreviations refer to the abbreviations used below:
Ac (acetyl), BINAP (2,2'-bis(disphenylphosphino)-1,1'-binaphthalene), dba (dibenzylidene acetone), Bu (Butyl), tBu (tert-Butyl), DCE (dichloroethane), DCM (Dichloromethane), DIEA (di-isopropyl ethylamine), DMA (dimethyl acetamide), 4-DMAP (4-dimethylaminopyridine), DMSO (Dimethyl Sulfoxide), DMF (N,N-Dimethylformamide), Dppf (1,1'-bis(diphenyl phosphine ferrocene)), EtOAc (Ethyl acetate), EtOH (Ethanol), g (gram), cHex (Cyclohexane), HATU (N-[(Dimethylamino)(3H-[1,2,3]triazolo[4,5-b]pyridin-3-yloxy)methylene]-N-methylmethanaminium-hexafluoro phosphate), HBTU (N,N,N',N'-Tetramethyl-O-(1H-benzotriazol-1-yl)uronium hexafluorophosphate), HPLC (High Performance Liquid Chromatography), hr (hour), LC (Liquid Chromatography), LDA (lithium diisopropyl amine), LiHMDS (lithium bis(trimethylsilyl)amide), MHz (Megahertz), MeOH (Methanol), min (minute), mL (milliliter), mmol (millimole), mM (millimolar), mp (melting point), MS (Mass Spectrometry), MW (microwave), NMM (N-methylmorpholine), NMP (N-methylpyrolidine), NMR (Nuclear Magnetic Resonance), O/N (overnight), PBS (Phosphate Buffered Saline), PPh$_3$ (triphenylphosphine), RT (room temperature), TEA (Triethyl amine), TFA (Trifluoroacetic acid), THF (Tetrahydrofuran), TLC (Thin Layer Chromatography), oTol (ortho-tolyl), T3P (Propylphosphonic anhydride), UV (Ultraviolet).

In general, the compounds according to Formula (I) and related formulae of this invention can be prepared from readily available starting materials. If such starting materials are not commercially available, they may be prepared by standard synthetic techniques. In general, the synthesis pathways for any individual compound of Formula (I) and related formulae will depend on the specific substituents of each molecule, such factors being appreciated by those of ordinary skilled in the art. The following general methods and procedures described hereinafter in the examples may be employed to prepare compounds of Formula (I) and related formulae. Reaction conditions depicted in the following schemes, such as temperatures, solvents, or co-reagents, are given as examples only and are not restrictive. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3$^{rd}$ Edition 1999.

Depending on the nature of the substituents (R1, Z and L etc.) different synthetic strategies may be selected for the synthesis of compounds of the invention. In the process illustrated in the following schemes the substituents (R1, Z and L etc.) are as above defined in the description unless otherwise mentioned.

Compounds of formula (I) can be prepared by intramolecular coupling of a carboxylic acid compound of general formula (II) wherein A1 is H, Li, Na or K as outlined in scheme 1. General protocols for such reaction are given below in the examples, using conditions and methods well known to those skilled in the art. Standard coupling agent, such as HBTU, EDC, T3P or isobutyl chloroformate can be used in the presence or not of an additive such as HOBt and a base such as DIEA, TEA or NMM in a suitable solvent such as DMF, Acetonitrile, THF or DCM at a temperature rising from about 0° C. to 50° C. Alternatively, a carboxylic acid derivative (such as acyl chloride) can be reacted using conditions and methods well known to those skilled in the art, in the presence of a base such as pyridine or DIEA in a suitable solvent such as toluene, DCM, THF or DMF, at a temperature rising from about 0° C. to RT, preferably at RT, for a few hours. In this cyclisation step, typical concentration of compound of general formula (II) ranges from 0.01 to 1M.

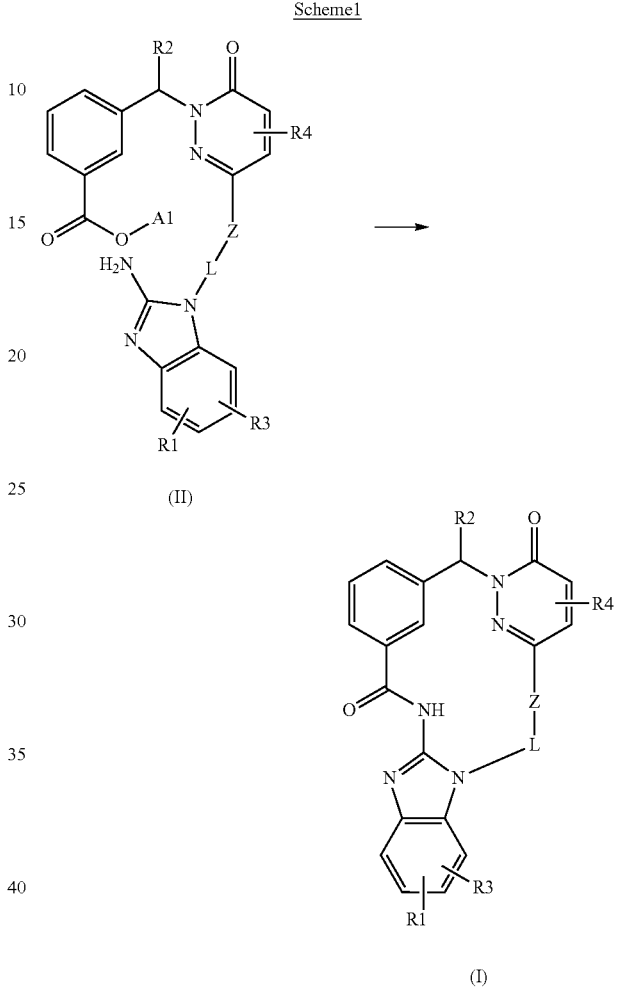

Scheme 1

Compounds of formula (II) wherein A1 is H or Li, Na or K can be prepared in two steps by alkylation of an amino benzimidazole compound of general formula (IV) with a compound of general formula (V) wherein R is an alkyl group and LG1 is a leaving group such as bromine, chlorine, iodine, an alkylsulfonate or any other suitable leaving group known to those skilled in the art followed by a hydrolysis of intermediate ester of general formula (III) wherein R is an alkyl group as outlined in scheme 2a. Alternatively intermediates of general formula (III) can be obtained by alkylation of an amino benzimidazole compound of general formula (IV) with an epoxide of general formula (V') wherein R is an alkyl group and L' is (CH$_2$)$_{n-1}$ as outlined in scheme 2b. General protocols for such reaction are given below in the examples, using conditions and methods well known to those skilled in the art. In a typical procedure, a compound of Formula (V) wherein LG1 is as defined above is treated with a base, such as but not limited to NaH, K$_2$CO$_3$, Cs$_2$CO$_3$, KOH, LDA, LiHMDS, preferably NaH, and with an aminobenzimidazole of general formula (IV) in a suitable solvent such as THF, dioxane, DMF, DMA, at a temperature between −20° C. to about 150° C., for a time between a few minutes to a few hours. Hydrolysis of the ester (III) wherein R is as above defined can be performed, for example, using HCl, H$_2$SO$_4$, or using LiOH, NaOH or KOH in water, water/THF, water/THF/ethanol or water/dioxane, at temperatures between 0 and 100° C. Acid or salt form is obtained depending on the reaction treatment selected (basic or acidic conditions).

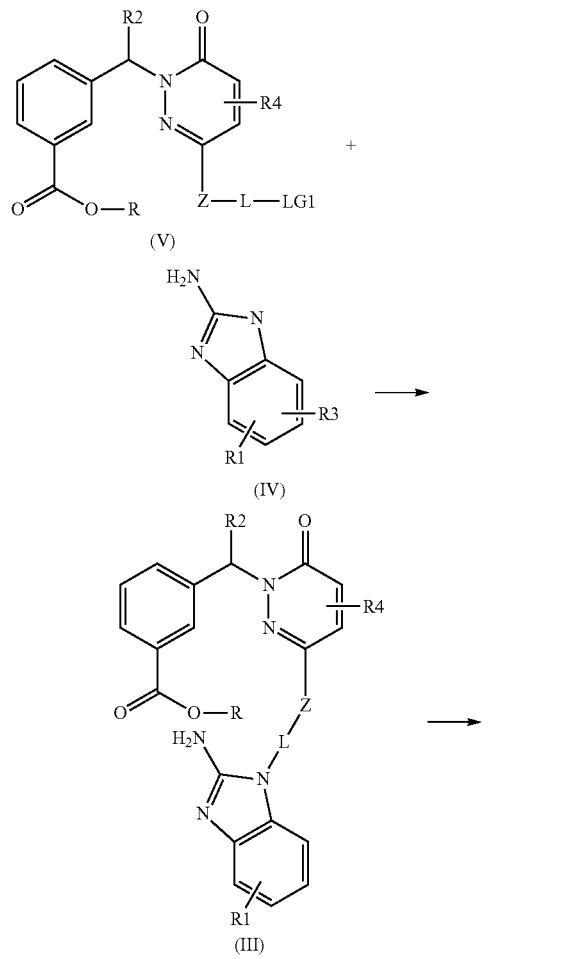

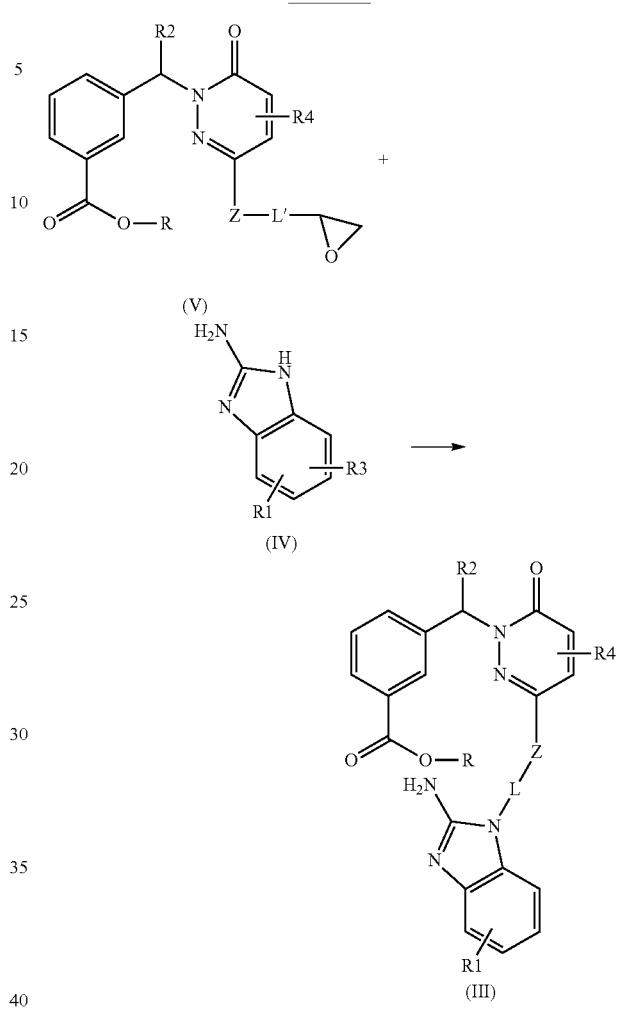

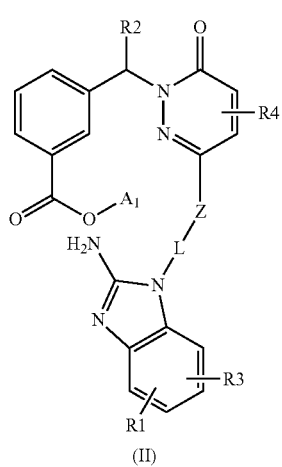

Aminobenzimidazoles of general formula (IV) can be obtained from commercial sources or can be synthesized following procedures well known to those skilled in the art such as but not limited to those described in *J. Org. Chem.* 1977, 42, 542 or *Bioorganic & Medicinal Chemistry Letters* 2006, 16, 2842-2845.

Compounds of formula (V) wherein LG1 is a leaving group such as bromine, chlorine, iodine, an alkylsulfonate or any other suitable leaving group known to those skilled in the art can be prepared from an alcohol of general formula (VI) wherein R is as above defined using conditions and methods well known to those skilled in the art as outlined in scheme 3. In a typical procedure, to obtain a compound of general formula (V) wherein R is as above defined and LG1 is an halogen, a compound of Formula (VI) wherein R is as above defined, can be treated with an halogenation agent such as SOCl$_2$, POCl$_3$, PCl$_5$, PBr$_3$ in a solvent such as DCM at a temperature rising from 0° C. to 60° C., preferably at RT for a few hours. To obtain a compound of general Formula (V) wherein LG1 is an alkylsulfonate, typical sulfonylation conditions use appropriate sulfonyl chloride in presence of a base such as TEA, DIEA or pyridine, optionally, a catalytic amount of 4-DMAP in a solvent such as DCM or THF at a temperature rising from 0° C. to 50° C., preferably at RT.

Scheme 3

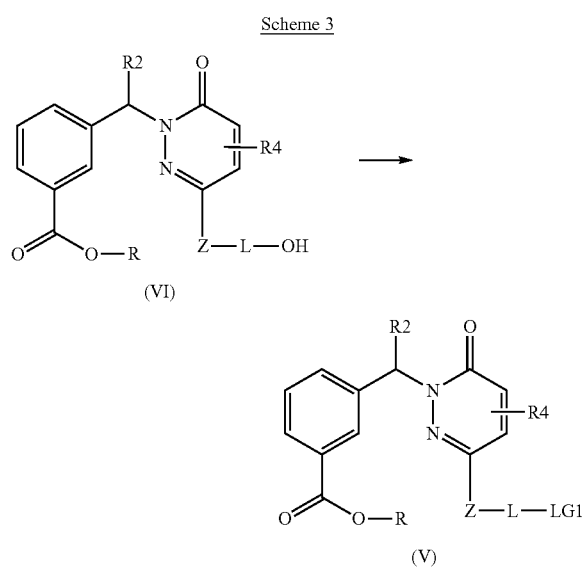

Compounds of formula (VI) wherein R is as above defined can be prepared by Suzuki-Miyura coupling reaction between a pyridazinone of general formula (VIII) wherein LG2 is halogen or a trifluoromethanesulfonate group and R is as above defined and a boronic acid or ester of Formula (VII) wherein R is as above defined as outlined in Scheme 4. General protocols for the Suzuki-Miyura coupling reaction are given below in the Examples, using conditions and methods well known to those skilled in the art to perform such coupling (see for example Miyaura, N.; Suzuki, A. Chem. Rev. 1995, 95, 2457; Takahiro I. and Toshiaki M., Tetrahedron Lett. 2005, 46, 3573-3577). In a typical procedure, an pyridazinone of general formula (VIII) and a boronic acid or ester of Formula (VII) are heated in a suitable solvent, such as THF, toluene, DMF or dioxane, in the presence or absence of water as a co-solvent, in the presence of a base, such as $Cs_2CO_3$, $Na_2CO_3$, $K_2CO_3$, CsF, and with an appropriate catalyst such as but not limited to dichlorobis(triphenylphosphine)palladium(II), $Pd(PPh_3)_4$ or 1,1'-bis(diphenylphosphino)ferrocenedichloro palladium (II), $Pd(OAc)_2$, $Pd_2(dba)_3$, $Pd(Cl)_2(PPh_3)_2$ or Pd/C in the presence or absence of an additional ligand, such as but not limited to $P(tBu)_3$, $P(oTol)_3$, $PPh_3$, BINAP. This coupling reaction can be carried out at a temperature between about 20° C. to about 150° C., preferably at about 120° C., for a few minutes to a few hours, possibly under microwave irradiation.

Scheme 4

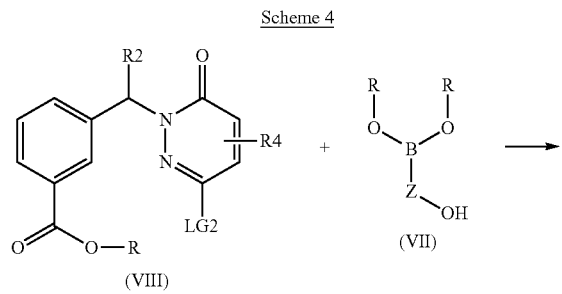

Boronic acid and esters of general formula (VII) wherein R is as above defined can be obtained from commercial sources or can be synthesized following procedures well known to those skilled in the art such as but not limited to those described in Boronic Acids, Edited by Dennis G. Hall 2005 WILEY-VCH Verlag GmbH & Co. KGaA, Weinheim or J. Chem. Soc., 60, 1995, 7508-7510.

Alternatively, Compounds of formula (VI) wherein R is as above defined can be prepared by Suzuki-Miyura coupling reaction between a pyridazinone boronic ester of general formula (X) wherein R is as above defined and a compound of general formula (IX) wherein LG2 is an halogen or a trifluoromethanesulfonate group as outlined in scheme 5. Typical procedures for those transformations are the same as described above.

Scheme 5

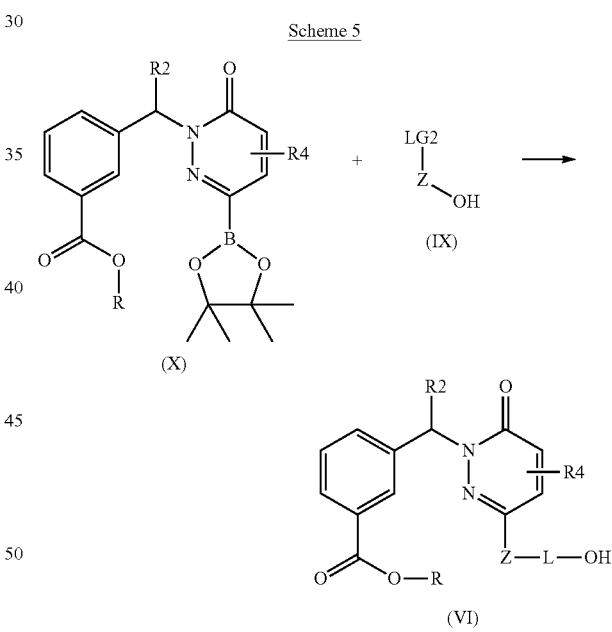

Boronic esters of general formula (X) wherein R is as above defined can be prepared from a pyridazinone of general formula (VIII) wherein LG2 is halogen or a trifluoromethanesulfonate group and R is as above defined by reaction with an appropriate diboron derivative, such as but not limited to bis(pinacolato)diboron, bis(catecholate)diboron, bis(diethyl-D-tartrate glycolato)diboron, bis(hexyleneglycolato)diboron, bis(neopentylglycolato)diboron, preferably bis(pinacolato)diboron, in the presence of a suitable catalyst, such as but not limited to 1,1'bis(diphenylphosphino)ferrocenedichloro palladium(II), dichlorobis(triphenylphosphine)palladium(II), $Pd(PPh_3)_4$, $Pd(OAc)_2$, $Pd_2(dba)_3$, $Pd(Cl)_2(PPh_3)_2$, preferably 1,1'bis(diphenylphosphino)ferrocenedichloro palladium(II), in the presence of a suitable base such as but not limited to potassium acetate, cesium fluoride, potassium carbonate, preferably potassium acetate, in the presence of a solvent such as but not limited to THF, dioxane, DCE, DMF, preferably THF or dioxane, at a temperature between about 20° C. to about 150° C., preferably at about 120° C., for a few minutes to a few hours, possibly under microwave irradiation.

Compounds of formula (VIII) wherein LG2 is halogen or a trifluoromethanesulfonate group and R is as above defined can be prepared by alkylation of a pyridazinone of general formula (XI) wherein LG2 is as above defined with a compound of general formula (XII) wherein R is as above define and LG1 is a leaving group such as bromine, chlorine, iodine, an alkylsulfonate or any other suitable leaving group known to those skilled in the art or an OH group as outline in scheme 6. General protocols for such transformation are given below in the Examples, using conditions and methods well known to those skilled in the art. In a typical procedure, a pyridazinone of general formula (XI) wherein LG2 is as above defined is treated with a base, such as but not limited to NaH, $K_2CO_3$, $Cs_2CO_3$, LDA, LiHMDS, preferably NaH, and with compound of general formula (XII) wherein R is as above define and LG1 is a leaving group such as bromine, chlorine, iodine, an alkylsulfonate or any other suitable leaving group known to those skilled in the art, in a suitable solvent like THF, dioxane, DMF, DMA, at a temperature between −20° C. to about 150° C., for a time between a few minutes to a few hours. Alternatively, Compounds of formula (VIII) wherein R and LG2 are as above defined can be obtained by reaction of a compound of Formula (XII) wherein L1 is an OH group with a pyridazinone of Formula (XI) wherein LG2 is as above defined using conditions well known to those skilled in the art for a Mitsunobu reaction (see for example Hughes, D. L. *Organic Reactions* (New York), 1992, 42, 335-656; Reynolds, A. J.; Kassiou, M. *Current Organic Chemistry*, 2009, 13 (16); 1610-1632). Typically, the reaction takes place in the presence of a phosphine, such as but not limited to $P(tBu)_3$, $PPBu_3$, $P(oTol)_3$, $PPh_3$, in the presence of an azadicarboxylate, such as but not limited to diethylazadicarboxylate, diisopropylazadicarboxylate, Tetramethylazodicarboxamide, in a solvent such as THF, dioxane, DCM, DCE, at a temperature between −20° C. to about 150° C., preferably at room temperature, for a time between a few minutes to a few hours.

Scheme 6

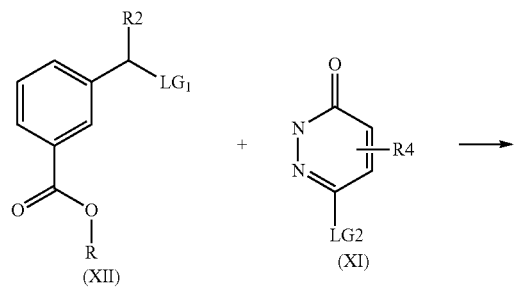

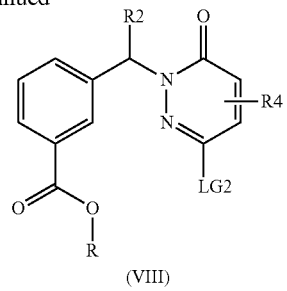

(VIII)

Compounds of this invention can be isolated in association with solvent molecules by crystallization from an appropriate solvent or by evaporation of an appropriate solvent. The pharmaceutically acceptable anionic salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent.

The pharmaceutically acceptable cationic salts of the compounds of Formula (I), which contain an acidic center, may be prepared in a conventional manner. For example, a solution of the free acid may be treated with a suitable base, either neat or in a suitable solution, and the resulting salt isolated either by filtration or by evaporation under vacuum of the reaction solvent. In some cases, salts can be prepared by mixing a solution of the acid with a solution of an alkali or earth alkali salt (such as sodium ethylhexanoate, magnesium oleate), employing a solvent in which the desired alkali or earth alkali salt of the compounds of formula (I) precipitates, or can be otherwise isolated by concentration and addition of a non-solvent.

Both types of salts may be formed or interconverted using ion-exchange resin techniques.

Depending on the conditions used, the reaction times are generally between a few minutes and 14 days. The reaction temperature is between about −30° C. and about 140° C., normally between −10° C. and 90° C., in particular between about 0° C. and 70° C. The formula (I) and related formulae also encompasses the optically active forms (stereoisomers), the enantiomers, the racemates, the diastereomers and the hydrates and solvates of these compounds. The term "solvates of the compounds" is taken to mean adductions of inert solvent molecules onto the compounds which form owing to their mutual attractive force. Solvates are, for example, mono- or dihydrates or alcoholates.

The synthetic strategies and methods described above can be used to obtain all compounds according to the present invention. In particular all synthetic strategies and methods described can be used for the synthesis of following compounds:

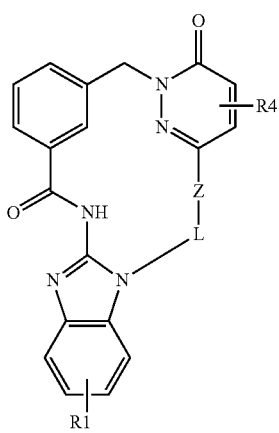

The term "pharmaceutically usable derivatives" is taken to mean, for example, the salts of the compounds of the formula I and so-called pro-drug compounds.

The term "prodrug derivatives" is taken to mean compounds of the formula I which have been modified with, for example, alkyl or acyl groups, sugars or oligopeptides and which are rapidly cleaved in the organism to form the active compounds. Preferably "prodrug", as of the compounds of formula I, refers to derivative compounds that are rapidly transformed in vivo to yield the parent compound of the formula I, as for example by hydrolysis in blood. T. Higuchi and V. Stella provide a thorough discussion of the prodrug concept in "Pro-drugs as Novel Delivery Systems", Vol 14 of the A.C.S. Symposium Series, American Chemical Society (1975). Examples of esters useful as prodrugs for compounds containing carboxyl groups can be found on pages 14-21 of "Bioreversible Carriers in Drug Design: Theory and Application", edited by E. B. Roche, Pergamon Press: New York (1987). It is intended that these references, and any others cited throughout this specification, are incorporated herein by reference.

These also include biodegradable polymer derivatives of the compounds according to the invention, as described, for example, in Int. J. Pharm. 115, 61-67 (1995).

The formula (I) and related formulae also encompasses mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

Pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The active ingredients can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds. Syrups can be prepared by dissolving the compounds in an aqueous solution with a suitable flavour, while elixirs are prepared using a non-toxic alcoholic vehicle. Suspensions can be formulated by dispersion of the compounds in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula (I), and related formulae and salts, solvates and physiologically functional derivatives thereof and the other active ingredients can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula (I), and related formulae and the salts, solvates and physiologically functional derivatives thereof and the other active ingredients can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropyl-methacrylamidophenol, polyhydroxyethylaspartamido-phenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, poly-orthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or sus-pended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insuf-flators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula (I), and related formulae and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

The present invention furthermore relates to a method for treating a subject suffering from a IRAK related disorder, comprising administering to said subject an effective amount of a compound of formula I and related formulae. The present invention preferably relates to a method, wherein the IRAK associated disorder is an autoimmune disorder or condition associated with an overactive immune response or cancer. The present invention furthermore relates to a method of treating a subject suffering from an immunoregulatory abnormality, comprising administering to said subject a compound of formula (I), and related formulae in an amount that is effective for treating said immunoregulatory abnormality. The present invention preferably relates to a method wherein the immunoregulatory abnormality is an autoimmune or chronic inflammatory disease selected from the group consisting of: allergic diseases, amyotrophic lateral sclerosis (ALS), systemic lupus erythematosus, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma. The present invention furthermore relates to a method wherein the immunoregulatory abnormality is bone marrow or organ transplant rejection or graft-versus-host disease. The present invention furthermore relates to a method wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, systemic sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, parkison diseases, trauma, and chronic bacterial infection.

Preferably, disorders associated with IRAK are selected from Rheumatoid Arthritis Psoriatic arthritis, Osteoarthritis, Systemic Lupus Erythematosus, Lupus nephritis, Ankylosing Spondylitis, Osteoporosis, Systemic sclerosis, Multiple Sclerosis, Psoriasis, Type I diabetes, Type II diabetes, Inflammatory Bowel Disease (Cronh's Disease and Ulcerative Colitis), Hyperimmunoglobulinemia D and periodic fever syndrome, Cryopyrin-associated periodic syndromes, Schnitzler's syndrome, Systemic juvenile idiopathic arthritis, Adult's onset Still's disease, Gout, Pseudogout, SAPHO syndrome, Castleman's disease, Sepsis, Stroke, Atherosclerosis, Celiac disease, DIRA (Deficiency of IL-1 Receptor Antagonist), Alzheimer's disease, Parkinson's disease, Cancer.

Preferred compounds of formula (I), and related formulae exhibit a IC50 for the binding to IRAK of less than about 5 µM, preferably less than about 1 µM and even more preferably less than about 0.100 µM.

EXPERIMENTAL PART

In the following the present invention shall be illustrated by means of some examples, which are not construed to be viewed as limiting the scope of the invention.
General:
The HPLC and LC data provided in the examples described below were obtained as followed.
Method A:
Column Waters Xbridge™ C8 50 mm×4.6 mm at a flow of 2 mL/min; 8 min gradient $H_2O:CH_3CN:TFA$ from 100:0:0.1% to 0:100:0.1%

Method B:

Column Waters Xbridge™ C8 50 mm×4.6 mm at a flow of 1 mL/min; 8 min gradient $H_2O:CH_3CN:NH_4HCO_3$ from 100:0:0.1% to 0:100:0.1%

Method C:

Column Waters Xbridge™ C8 50 mm×4.6 mm at a flow of 1 mL/min; 8 min gradient $H_2O:CH_3CN:NH_4OAc$ from 100:0:0.1% to 0:100:0.1% UV detection: max plot or specified wave length.

Mass spectrum: AGILENT 1100 series with Single Quad Detector

The NMR data provided in the examples described below were obtained using a Bruker AV-400 MHz.

The compounds of invention have been named according to the standards used in the program Autonom or IUPAC Name from Chemaxon.

The compounds according to formula (I) can be prepared from readily available starting materials by several synthetic approaches, using both solution-phase and solid-phase chemistry protocols or mixed solution and solid phase protocols. Examples of synthetic pathways are described below in the examples. Unless otherwise stated, compounds of Formula (I) and related formulae obtained as a racemic mixture can be separated to provide an enantiomerically enriched mixture or a pure enantiomer.

The commercially available starting materials used in the following experimental description were purchased from Aldrich or Sigma or ABCR unless otherwise reported.

Intermediate 1

3-(3-Chloro-6-oxo-6H-pyridazin-1-ylmethyl)-benzoic acid methyl ester

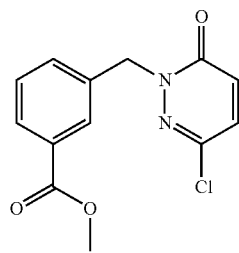 [SMILES: COC(=O)c1cccc(Cn2nc(Cl)ccc2=O)c1]

A solution of 3-bromomethyl-benzoic acid methyl ester (9.6, 41.9 mmol), 6-chloro-2H-pyridazin-3-one (5.4 g, 41.9 mmol) and cesium carbonate (13.6 g, 41.9 mmol) in NMP (10 mL) was stirred at RT overnight. The reaction mixture was then treated with ice cold water and the solid formed was filtered. Purification by flash chromatography on silica of this crude afforded the title compound as an off-white solid (9.8 g, 94%). $^1$H NMR (400 MHz, DMSO-$d_6$): δ 7.90-7.88 (m, 2H), 7.58 (dd, J=5.88, 5.64 Hz, 2H), 7.53-7.49 (m, 1H), 7.11 (d, J=9.72 Hz, 1H), 5.27 (s, 2H), 3.84 (s, 3H). LC/MS: (Method A) 279.0 (M+H), RT. 3.7 min, 93.8% (Max), 93.9% (254 nm).

Intermediate 2

Methyl 3-((3-(3-(bromomethyl)phenyl)-6-oxopyridazin-1(6H)-yl)methyl)benzoate

Step 1: Formation of 3-[3-(3-Hydroxymethyl-phenyl)-6-oxo-6H-pyridazin-1-ylmethyl]-benzoic acid methyl ester

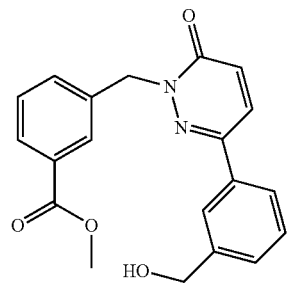 [SMILES: COC(=O)c1cccc(Cn2nc(-c3cccc(CO)c3)ccc2=O)c1]

A mixture of 3-(3-chloro-6-oxo-6H-pyridazin-1-ylmethyl)-benzoic acid methyl ester (2 g, 7.1 mmol) and [3-(4,4,5,5-Tetramethyl-[1,3,2]dioxaborolan-2-yl)-phenyl]methanol (1.64 g, 10.7 mmol) in $DMF/H_2O$ (9 mL/1 mL) was degassed under $N_2$ atmosphere for min. $Na_2CO_3$ (10.5 mL, 2 M solution, 21.1 mmol) and bis(triphenylphosphine)palladium(II) dichloride (250 mg, 0.35 mmol) were then added and the mixture was heated at 100° C. for 3 h. The reaction solvent was removed under reduced pressure and the residue was diluted with water and extracted with EtOAc (2×150 mL). The combined organic phases were washed with water, brine, dried over anhydrous $Na_2SO_4$, filtered and concentrated. Purification by flash chromatography on silica (EtOAc:n-Hexane; 70:30) of the crude obtained afforded the tittle compound as a yellow solid (1.5 g, 60%). $^1$H NMR (400 MHz, DMSO-$d_6$): 400 MHz, DMSO-d6: δ 8.06 (d, J=9.76 Hz, 1H), 7.96 (s, 1H), 7.88 (d, J=7.72 Hz, 1H), 7.82 (s, 1H), 7.74 (d, J=7.52 Hz, 1H), 7.63 (d, J=7.68 Hz, 1H), 7.51 (t, J=7.64 Hz, 1H), 7.46-7.39 (m, 2H), 7.10 (d, J=9.72 Hz, 1H), 5.40 (s, 2H), 5.28 (t, J=5.68 Hz, 1H), 4.56 (d, J=4.40 Hz, 2H), 3.83 (s, 3H). LC/MS: (Method A) 351.2 (M+H), RT. 3.63 min, 77.7% (Max).

Step 2: Formation of Methyl 3-((3-(3-(bromomethyl)phenyl)-6-oxopyridazin-1(6H)-yl)methyl)benzoate

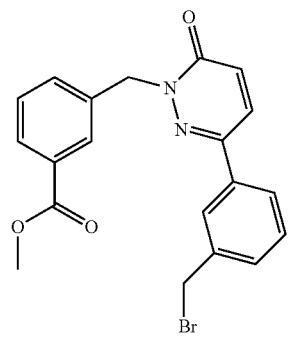 [SMILES: COC(=O)c1cccc(Cn2nc(-c3cccc(CBr)c3)ccc2=O)c1]

Phosphorous tribromide (0.5 mL, 4.7 mmol) was slowly added to a solution of Methyl 3-[3-(3-Hydroxymethyl-phenyl)-6-oxo-6H-pyridazin-1-ylmethyl]-benzoic acid methyl ester (1.5 g, 4.2 mmol) in DCM (10 mL) maintained at 0° C. The reaction mixture was then allowed to warm to RT and stirred for 1 h. It was quenched with water and extracted with DCM (3×10 mL). The combined organic phases were dried over anhydrous $Na_2SO_4$, filtered and concentrated to give the title compound as a yellow solid (1.5 g, 88%). $^1$H NMR (400 MHz, DMSO-$d_6$): δ 8.08 (dd, J=9.76, 2.32 Hz, 1H), 8.06-7.97 (m, 2H), 7.88 (d, J=7.76 Hz, 1H), 7.83 (d, J=7.60 Hz, 1H), 7.65-7.61 (m, 1H), 7.56-7.49 (m, 3H), 7.12 (d, J=9.72 Hz, 1H), 5.41 (s, 2H), 4.76 (s, 2H), 3.83 (s, 3H). LC/MS: (Method A) 415.0 (M+H), RT. 4.8 min, 72.3% (Max).

Intermediate 3

3-(6-Oxo-3-{3-[2-(toluene-4-sulfonyloxy)-ethyl]-phenyl}-6H-pyridazin-1-ylmethyl)-benzoic acid methyl ester Step 1: Formation of 3-{3-[3-(2-Hydroxy-ethyl)-phenyl]-6-oxo-6H-pyridazin-1-ylmethyl}-benzoic acid methyl ester

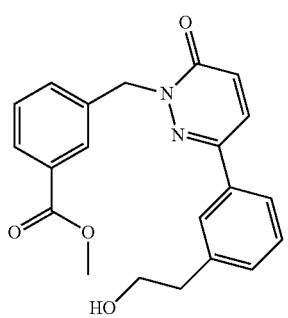 [SMILES: COC(=O)c1cccc(Cn2nc(-c3cccc(CCO)c3)ccc2=O)c1]

The title compound was obtained following procedure described for intermediate 2, step 2 as a yellow solid (3 g, 60%). $^1$H NMR (400 MHz, DMSO-$d_6$): δ 8.07 (d, J=9.72 Hz, 1H), 7.97 (s, 1H), 7.88 (d, J=7.76 Hz, 1H), 7.72-7.68 (m, 2H), 7.64 (d, J=7.76 Hz, 1H), 7.51 (t, J=7.64 Hz, 1H), 7.39 (t, J=7.64 Hz, 1H), 7.30 (d, J=7.64 Hz, 1H), 7.10 (d, J=9.76 Hz, 1H), 5.40 (s, 2H), 4.66 (t, J=5.20 Hz, 1H), 3.83 (s, 3H), 3.65-3.61 (m, 2H), 2.78 (t, J=6.96 Hz, 2H). LC/MS: (Method A) 365.2 (M+H), RT. 3.72 min, 95.91% (Max), 97.6% (254 nm).

Step 2: Formation of 3-(6-Oxo-3-{3-[2-(toluene-4-sulfonyloxy)-ethyl]-phenyl}-6H-pyridazin-1-ylmethyl)-benzoic acid methyl ester

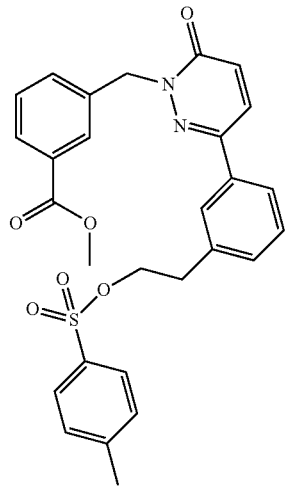 [SMILES: COC(=O)c1cccc(Cn2nc(-c3cccc(CCOS(=O)(=O)c4ccc(C)cc4)c3)ccc2=O)c1]

4-Dimethyl amino pyridine (0.01 g, 0.08 mmol) followed by para-toluene sulphonyl chloride (0.5 g, 2.6 mmol) were slowly added to a solution of 3-{3-[3-(2-Hydroxy-ethyl)-phenyl]-6-oxo-6H-pyridazin-1-ylmethyl}-benzoic acid methyl ester (1.0 g, 2.7 mmol) and TEA (0.47 mL, 3.3 mmol) in DCM (10 mL) maintained at 0° C. The reaction mixture was then allowed to warm to RT and stirred for 1 h. It was quenched with water and extracted with DCM (3×10 mL). Combined organic phases were dried over anhydrous $Na_2SO_4$, filtered and concentrated to give the title compound as a yellow solid (4.3 g, 98%). LC/MS: (Method A) 519.0 (M+H), RT 5.20 min, 62.6% (Max).

Intermediate 4

2-(2-amino-1H-benzo[d]imidazol-5-yl)-N,N-dimethylacetamide

Step 1: Formation of 2-(benzo[c][1,2,5]thiadiazol-5-yl)-N,N-dimethylacetamide

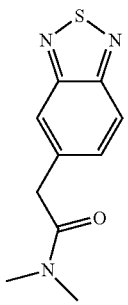

$T_3P$ (50% w/v solution in ethyl acetate, 49 ml, 77.2 mmol) was added to a solution of Benzo[1,2,5]thiadiazol-5-yl-acetic acid (5 g, 25.7 mmol), N,N-Dimethylamine (15.4 ml, 30.8 mmol) and triethylamine (0.1 mL, 0.8 mmol) in THF (50 mL) maintained at 0° C. The reaction mixture was allowed to warm to RT. After 12 h, a 10% sodium bicarbonate solution (15 mL) was added to the reaction mixture which was then extracted with dichloromethane (3×10 mL). The combined organic phases were washed with a 10% citric acid solution, dried over anhydrous $Na_2SO_4$, filtered and concentrated in vacuum to give the title compound as a yellow solid (3 g, 53%). $^1$H NMR (400 MHz, DMSO-$d_6$): δ 8.00 (d, J=9.00 Hz, 1H), 7.88 (d, J=0.68 Hz, 1H), 7.58-7.56 (m, 1H), 3.93 (s, 2H), 3.06 (s, 3H), 2.85 (s, 3H). LC/MS: (Method A) 222.0 (M+H), RT. 2.4 min, 96.1% (Max), 96.5% (220 nm).

Step 2: Formation of 2-(3,4-diaminophenyl)-N,N-dimethylacetamide

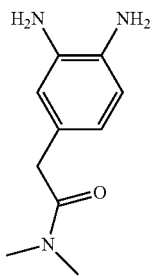

A suspension of 2-(benzo[c][1,2,5]thiadiazol-5-yl)-N,N-dimethylacetamide (3 g, 13.5 mmol) and Raney nickel (9 g, 40.5 mmol) in methanol (100 mL) was heated at 45° C. in an autoclave (pressure=2 kg/cm$^2$) for 12 h. The hot suspension was then filtered through a celite pad which was washed with methanol. The filtrate was concentrated under reduced pressure to afford the title compound as brown solid (2 g, 76%). $^1$H NMR (400 MHz, DMSO-$d_6$): δ 6.72-6.35 (m, 2H), 6.29-6.16 (m, 1H), 4.39 (brs, 2H), 4.29 (brs, 2H), 3.32 (s, 2H), 2.92 (s, 3H), 2.78 (s, 3H). LC/MS: (Method B) 194.3 (M+H), RT. 2.4 min, 92.9% (Max).

Step 3: Formation of 2-(2-amino-1H-benzo[d]imidazol-5-yl)-N,N-dimethylacetamide

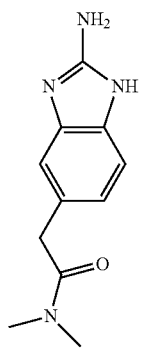 [SMILES: CN(C)C(=O)Cc1ccc2[nH]c(N)nc2c1]

A solution of 2-(3,4-diaminophenyl)-N,N-dimethylacetamide (3.0 g, 15.5 mmol) in ethanol (15 mL) was added over the period of 30 min to a stirred solution of Cyanogen bromide (1.8 g, 17.0 mmol) in water (100 mL). After 20 h, ethanol was removed under reduced pressure and the resulting aqueous solution was washed with ethyl acetate (3×50 mL). The ethyl acetate layer was back extracted with water. The combined aqueous layers were basified with a saturated solution of $NaHCO_3$ and extracted with ethyl acetate (2×50 mL). The combined organic phases were dried over anhydrous $Na_2SO_4$, filtered and concentrated in vacuum to afford the title compound as brown solid (1.0 g, 45%). $^1$H NMR (400 MHz, DMSO-$d_6$): δ 10.58 (s, 1H), 6.99-6.95 (m, 1H), 6.95-6.90 (m, 1H), 6.70 (d, m, 1H), 6.05 (brs, 2H), 3.62 (s, 2H), 2.95 (s, 3H), 2.81 (s, 3H). LC/MS: (Method A) 219.2 (M+H), RT. 1.5 min, 97.0% (Max), 97.0% (220 nm).

Intermediate 5

3-(3-Chloro-4-methyl-6-oxo-6H-pyridazin-1-ylmethyl)-benzoic acid methyl ester

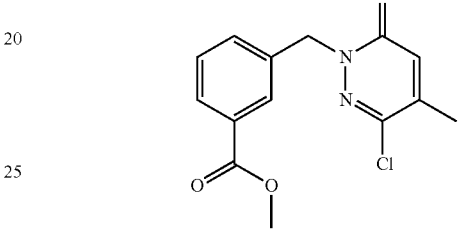

The title compound was obtained following procedure described for intermediate 1 from 3-bromomethyl-benzoic acid methyl ester and 6-Chloro-5-methyl-2H-pyridazin-3-one (purchased from Combi-blocks) as an off-white solid (3.8 g, 94%). $^1$H NMR (400 MHz, DMSO-$d_6$): δ 7.89-7.87 (m, 2H), 7.57 (t, J=6.44 Hz, 1H), 7.50 (t, J=7.68 Hz, 1H), 7.04 (d, J=1.20 Hz, 1H), 5.25 (s, 2H), 3.84 (s, 3H), 2.19 (s, 3H). LC/MS: (Method A) 293.0 (M+H), RT. 4.4 min, 90.1% (Max).

Intermediate 6

3-[3-(3-Bromomethyl-phenyl)-4-methyl-6-oxo-6H-pyridazin-1-ylmethyl]-benzoic acid methyl ester Step 1: Formation of 3-[3-(3-Hydroxymethyl-phenyl)-4-methyl-6-oxo-6H-pyridazin-1-ylmethyl]-benzoic acid methyl ester

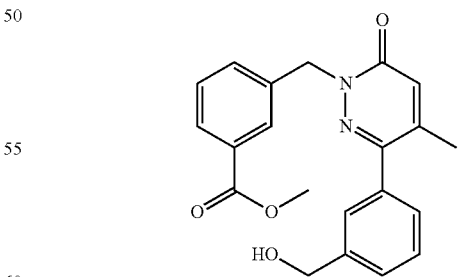

The title compound was obtained following procedure described for intermediate 2, step 1 from 3-(3-Chloro-4-methyl-6-oxo-6H-pyridazin-1-ylmethyl)-benzoic acid methyl ester and 3-hydroxymethyl phenyl boronic acid, as a yellow solid (1.0 g, 55%). $^1$H NMR (400 MHz, DMSO-$d_6$): δ 7.98 (s, 1H), 7.94 (s, 1H), 7.88 (d, J=1.24 Hz, 1H), 7.49

(t, J=7.64 Hz, 1H), 7.42-7.39 (m, 3H), 7.36-7.33 (m, 1H), 6.95 (d, J=1.16 Hz, 1H), 5.33 (s, 2H), 5.26 (t, J=5.72 Hz, 1H), 4.53 (d, J=5.76 Hz, 2H), 3.84 (s, 3H), 2.12 (s, 3H). LC/MS: (Method A) 365.2 (M+H), RT. 3.65 min, 87.40% (Max), 95.3% (254 nm).

Step 2: Formation of 3-[3-(3-Bromomethyl-phenyl)-4-methyl-6-oxo-6H-pyridazin-1-ylmethyl]-benzoic acid methyl ester

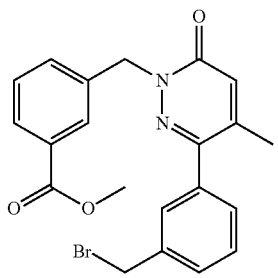 [SMILES: COC(=O)c1cccc(Cn2nc(-c3cccc(CBr)c3)c(C)cc2=O)c1]

The title compound was obtained following procedure described for intermediate 2, step 2 from 3-[3-(3-Hydroxymethyl-phenyl)-4-methyl-6-oxo-6H-pyridazin-1-ylmethyl]-benzoic acid methyl ester as a yellow solid (1.0 g, 90%). $^1$H NMR (400 MHz, DMSO-$d_6$): δ 8.11 (s, 1H), 7.94 (d, J=1.32 Hz, 1H), 7.60-7.53 (m, 3H), 7.46-7.42 (m, 3H), 6.96 (d, J=1.20 Hz, 1H), 5.35 (s, 2H), 4.75 (s, 2H), 3.84 (s, 3H), 2.13 (s, 3H). LC/MS: (Method A) 429.0 (M+2), RT. 4.99 min, 81.5% (Max).

Intermediate 7

[4-Methyl-3-(4,4,5,5-tetramethyl-[1,3,2]dioxaborolan-2-yl)-phenyl]-methanol

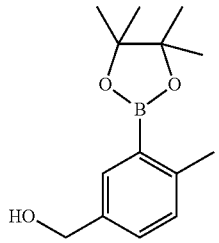 [SMILES: Cc1ccc(CO)cc1B1OC(C)(C)C(C)(C)O1]

A mixture of (3-Bromo-4-methyl-phenyl)-methanol (8.5 g, 42.2 mmol) and bis(pinacolato)diboron (11.8 g, 46.50 mmol) in 1,4-dioxane (50 mL) was degassed under $N_2$ atmosphere for 10 min. Potassium acetate (8.2 g, 84.55 mmol) was added to the above followed by [1,1'-Bis(diphenylphosphino)ferrocene]dichloropalladium(II).CH$_2$Cl$_2$ (1.54 g, 2.11 mmol) and the reaction mixture was heated at 100° C. for 15 h. The solvents were removed under reduced pressure, the residue obtained was diluted with water and extracted with EtOAc (2×150 mL). Combined organic phases were washed with water, brine, dried over anhydrous Na$_2$SO$_4$, filtered and concentrated. Purification of this crude by flash chromatography on silica (EtOAc:n-hexane; 70:30) afforded the title compound as a brown liquid (5.0 g, 84%). $^1$H NMR (400 MHz, DMSO-$d_6$): δ 7.59 (d, J=1.72 Hz, 1H), 7.25 (dd, J=7.76, 1.88 Hz, 1H), 7.11 (d, J=7.76 Hz, 1H), 5.10 (t, J=5.72 Hz, 1H), 4.43 (d, J=5.72 Hz, 2H), 2.42 (s, 3H), 1.29 (s, 12H).

Intermediate 8

3-[3-(5-Bromomethyl-2-methyl-phenyl)-6-oxo-6H-pyridazin-1-ylmethyl]-benzoic acid methyl ester Step 1: Formation of 3-[3-(5-Hydroxymethyl-2-methyl-phenyl)-6-oxo-6H-pyridazin-1-ylmethyl]-benzoic acid methyl ester

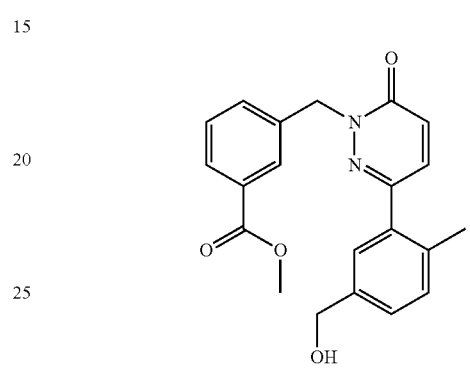

The title compound was obtained following procedure described for intermediate 2, step 1 from 3-(3-Chloro-6-oxo-6H-pyridazin-1-ylmethyl)-benzoic acid methyl ester and [4-Methyl-3-(4,4,5,5-tetramethyl-[1,3,2]dioxaborolan-2-yl)-phenyl]-methanol as a yellow solid (1.8 g, 69%). $^1$H NMR (400 MHz, DMSO-$d_6$): δ 7.94 (s, 1H), 7.90-7.87 (m, 1H), 7.67-7.61 (m, 3H), 7.53-7.49 (m, 1H), 7.30-7.24 (m, 2H), 7.07 (d, J=9.60 Hz, 1H), 5.37 (s, 2H), 5.19 (t, J=5.60 Hz, 1H), 4.49 (d, J=5.72 Hz, 2H), 3.84 (s, 3H), 2.24 (s, 3H). LC/MS: (Method A) 365.0 (M+H), RT. 3.75 min, 76.8% (Max).

Step 2: 3-[3-(5-Bromomethyl-2-methyl-phenyl)-6-oxo-6H-pyridazin-1-ylmethyl]-benzoic acid methyl ester

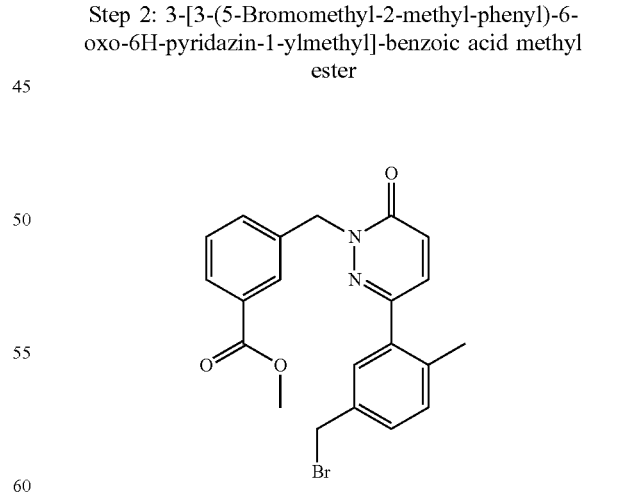

The title compound was obtained following procedure described for intermediate 2, step 2 from 3-[3-(5-Hydroxymethyl-2-methyl-phenyl)-6-oxo-6H-pyridazin-1-ylmethyl]-benzoic acid methyl ester as a yellow solid (1.9 g, 90%). LC/MS: (Method A) 429.0 (M+2), RT. 5.02 min, 60.8% (Max).

Intermediate 9

3-{6-Oxo-3-[5-(toluene-4-sulfonyloxymethyl)-pyridin-3-yl]-6H-pyridazin-1-ylmethyl}-benzoic acid methyl ester Step 1: Formation of 3-[3-(5-Hydroxymethyl-pyridin-3-yl)-6-oxo-6H-pyridazin-1-ylmethyl]-benzoic acid methylester

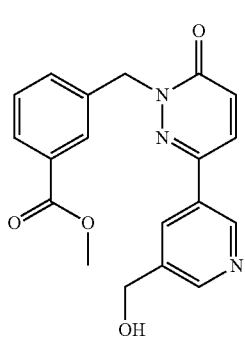 [SMILES: COC(=O)c1cccc(Cn2nc(-c3cncc(CO)c3)ccc2=O)c1]

The title compound was obtained following procedure described for intermediate 2, step 1 from 3-(3-chloro-6-oxo-6H-pyridazin-1-ylmethyl)-benzoic acid methyl ester (2 g, 7.1 mmol) and (5-(hydroxymethyl)pyridin-3-yl)boronic acid (2.5 g, 10.7 mmol) as a brown solid (1.0 g, 84%). $^1$H NMR (400 MHz, DMSO-$d_6$): δ 8.96 (d, J=2.16 Hz, 1H), 8.59 (d, J=1.80 Hz, 1H), 8.18-8.13 (m, 2H), 7.98 (s, 1H), 7.89 (d, J=1.20 Hz, 1H), 7.65 (d, J=7.76 Hz, 1H), 7.51 (t, J=7.72 Hz, 1H), 7.15 (d, J=9.72 Hz, 1H), 5.43-5.42 (m, 3H), 4.60 (d, J=5.64 Hz, 2H), 3.83 (s, 3H). LC/MS: (Method A) 352.0 (M+H), RT. 2.32 min, 93.68% (Max), 92.1% (254 nm).

Step 2: Formation of 3-{6-Oxo-3-[5-(toluene-4-sulfonyloxymethyl)-pyridin-3-yl]-6H-pyridazin-1-ylmethyl}-benzoic acid methyl ester

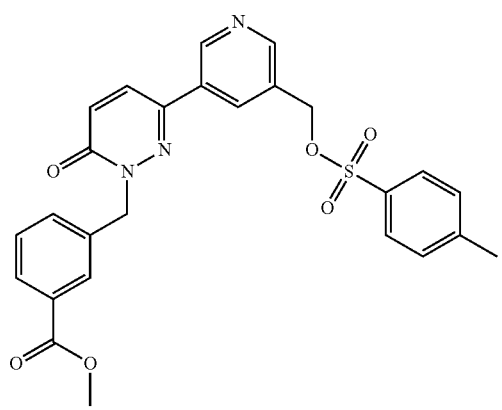 [SMILES: COC(=O)c1cccc(Cn2nc(-c3cncc(COS(=O)(=O)c4ccc(C)cc4)c3)ccc2=O)c1]

The title compound was obtained following procedure described for intermediate 3, step 2 from Methyl 3-[3-(5-Hydroxymethyl-pyridin-3-yl)-6-oxo-6H-pyridazin-1-ylmethyl]-benzoic acid methyl ester as a beige solid (1.5 g, 98%). $^1$H NMR (400 MHz, DMSO-$d_6$): δ 9.11 (t, J=2.20 Hz, 1H), 8.78 (dd, J=6.00, 1.96 Hz, 1H), 8.48-8.46 (m, 1H), 8.16-8.14 (m, 1H), 7.98 (d, J=8.44 Hz, 1H), 7.89 (d, J=7.72 Hz, 1H), 7.66 (d, J=7.68 Hz, 1H), 7.51 (t, J=7.68 Hz, 1H), 7.46 (d, J=8.08 Hz, 2H), 7.19 (dd, J=9.68, 5.60 Hz, 1H), 7.08-6.99 (m, 2H), 5.43 (s, 2H), 4.91 (s, 2H), 3.83 (s, 3H), 2.27 (s, 3H).

Intermediate 10

2-[3-(4,4,5,5-Tetramethyl-[1,3,2]dioxaborolan-2-yl)-phenoxy]-ethanol

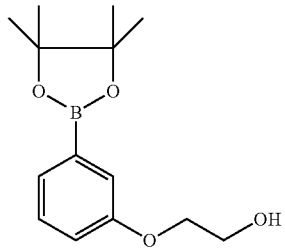 [SMILES: CC1(C)OB(c2cccc(OCCO)c2)OC1(C)C]

A mixture of 2-(3-Bromo-phenoxy)-ethanol (6 g, 27.64 mmol), 4 bis(pinacolato)diboron (7.7 g, 30.40 mmol) and potassium acetate (5.4 g, 55.2 mmol) in 1,4-dioxane (50 mL) was degassed with nitrogen for 20 min before the addition of 1,1'-Bis(diphenylphosphino)ferrocene]dichloropalladium (II).CH$_2$Cl$_2$ (1.01 g, 1.38 mmol). The reaction mixture was then heated at 100° C. for 14 h. It was filtered through a celite pad. The pad was extensively washed with dichloromethane/methanol and the filtrate was concentrated under reduced pressure. Purification by flash column chromatography on silica of the crude afforded the title compound as a brown solid (3.0 g, 42%). $^1$H NMR (400 MHz, DMSO-d6): δ 7.23 (t, J=8.08 Hz, 1H), 7.14-7.09 (m, 2H), 6.95 (dd, J=8.08, 2.28 Hz, 1H), 4.85-4.82 (m, 1H), 3.98-3.93 (m, 2H), 3.71-3.67 (m, 2H), 1.28 (s, 9H). LC/MS: (Method A) 265.3 (M+H), RT. 2.8 min, 72.0% (Max).

Intermediate 11

3-(6-Oxo-3-{3-[2-(toluene-4-sulfonyloxy)-ethoxy]-phenyl}-6H-pyridazin-1-ylmethyl)-benzoic acid methyl ester Step 1: Formation of 3-{3-[3-(2-Hydroxy-ethoxy)-phenyl]-6-oxo-6H-pyridazin-1-ylmethyl}-benzoic acid methyl ester

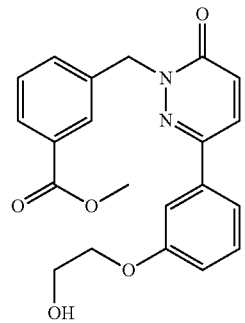 [SMILES: COC(=O)c1cccc(Cn2nc(-c3cccc(OCCO)c3)ccc2=O)c1]

A mixture of 3-(3-Chloro-6-oxo-6H-pyridazin-1-ylmethyl)-benzoic acid methyl ester (2 g, 7.91 mmol), 2-[3-(4, 4,5,5-Tetramethyl-[1,3,2]dioxaborolan-2-yl)-phenoxy]-ethanol (2.8 g, 10.79 mmol) and a solution of 2M Na$_2$CO$_3$ (10.5 mL, 21.57 mmol) in dimethylformamide/water (9:1; 30 mL) was degassed with nitrogen for 20 min before the addition of bis(triphenylphosphine)palladium(II) dichloride (0.25 g, 0.35 mmol). The reaction mixture was then heated at 100° C. for 4 h. It was filtered through a celite pad, the pad was extensively washed with dichloromethane/methanol and the filtrate was concentrated under reduced pressure. Purification by flash column chromatography on silica afforded the title compound as a yellow solid (2.0 g, 75%). LC/MS: (Method A) 381.2 (M+H), RT. 3.7 min, 64.9% (Max).

Step 2: Formation of 3-(6-Oxo-3-{3-[2-(toluene-4-sulfonyloxy)-ethoxy]-phenyl}-6H-pyridazin-1-ylmethyl)-benzoic acid methyl ester

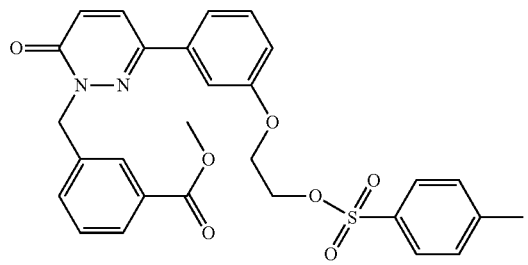 [SMILES: COC(=O)c1cccc(Cn2nc(-c3cccc(OCCOS(=O)(=O)c4ccc(C)cc4)c3)ccc2=O)c1]

The title compound was obtained following procedure described for intermediate 3, step 2 from 3-{3-[3-(2-Hydroxy-ethoxy)-phenyl]-6-oxo-6H-pyridazin-1-ylmethyl}-benzoic acid methyl ester as a brown gum (2.5 g, 89%). LC/MS: (Method A) 535.0 (M+H), RT. 5.2 min.

Intermediate 12

Methyl 3-((3-(5-(bromomethyl)-2-fluorophenyl)-6-oxopyridazin-1(6H)-yl)methyl)benzoate Step 1: Formation of Methyl 3-((3-(2-fluoro-5-(hydroxymethyl)phenyl)-6-oxopyridazin-1(6H)-yl)methyl)benzoate

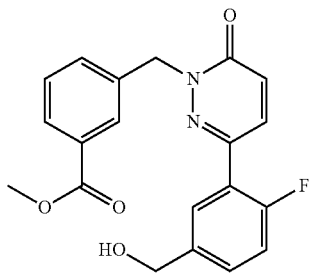 [SMILES: COC(=O)c1cccc(Cn2nc(-c3cc(CO)ccc3F)ccc2=O)c1]

The title compound was obtained following procedure described for intermediate 2, step 1 from 3-(3-chloro-6-oxo-6H-pyridazin-1-ylmethyl)-benzoic acid methyl ester and (4-fluoro-3-(4,4,5,5-tetramethyl-1,3,2-dioxaborolan-2-yl) phenyl)methanol as an off-white solid (2.21 g, 56%). $^1$H NMR (400 MHz, DMSO-d$_6$): δ 7.96 (s, 1H), 7.90-7.87 (m, 1H), 7.79 (dd, J=9.7, 2.5 Hz, 1H), 7.64-7.42 (m, 4H), 7.33-7.28 (m, 1H), 7.10 (d, J=9.7 Hz, 1H), 5.40 (s, 2H), 5.33 (t, J=5.8 Hz, 1H), 4.52 (d, J=4.0 Hz, 2H), 3.84 (s, 3H). LC/MS: (Method A) 369.2 (M+H), RT. 3.7 min, 65% (Max).

Step 2: Formation of Methyl 3-((3-(5-(bromomethyl)-2-fluorophenyl)-6-oxopyridazin-1(6H)-yl) methyl)benzoate

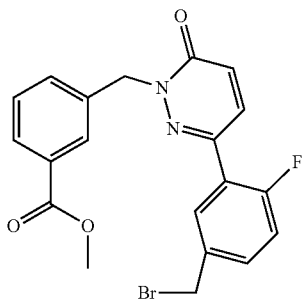 [SMILES: COC(=O)c1cccc(Cn2nc(-c3cc(CBr)ccc3F)ccc2=O)c1]

The title compound was obtained following procedure described for intermediate 2, step from Methyl 3-((3-(2-fluoro-5-(hydroxymethyl)phenyl)-6-oxopyridazin-1(6H)-yl)methyl)benzoate (2.21 g, 6 mmol) as an off-white solid (2.0 g, 78%). $^1$H NMR (400 MHz, DMSO-d$_6$): δ 7.96 (s, 1H), 7.90-7.87 (m, 1H), 7.79 (dd, J=9.7, 2.5 Hz, 1H), 7.64-7.42 (m, 4H), 7.33-7.28 (m, 1H), 7.10 (d, J=9.7 Hz, 1H), 5.75 (s, 2H), 4.77 (s, 2H), 3.84 (s, 3H). LC/MS: (Method A) 431.0 (M+H), RT. 4.9 min.

Intermediate 13

6-[3-(2-Hydroxy-ethyl)-phenyl]-5-methyl-2H-pyridazin-3-one

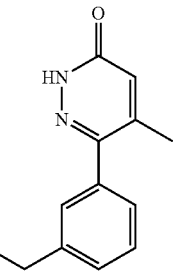

The title compound was obtained following procedure described for intermediate 11, step 1 from 6-Chloro-5-methyl-2H-pyridazin-3-one and 2-[3-(4,4,5,5-Tetramethyl-[1,3,2]dioxaborolan-2-yl)-phenyl]-ethanol as a white solid (800 mg, 50%). LC/MS: (Method A) 231.0 (M+H), RT. 2.1 min.

Intermediate 14

3-(4-Methyl-6-oxo-3-{3-[2-(toluene-4-sulfonyloxy)-ethyl]-phenyl}-6H-pyridazin-1-ylmethyl)-benzoic acid methyl ester

Step 1: Formation of 3-{3-[3-(2-Hydroxy-ethyl)-phenyl]-4-methyl-6-oxo-6H-pyridazin-1-ylmethyl}-benzoic acid methyl ester

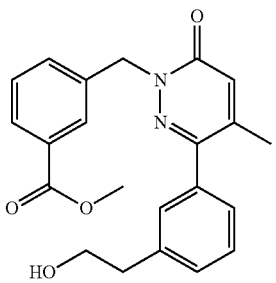 [SMILES: COC(=O)c1cccc(Cn2nc(-c3cccc(CCO)c3)c(C)cc2=O)c1]

A solution of 3-Bromomethyl-benzoic acid methyl ester (0.79 g, 3.47 mmol), 6-[3-(2-Hydroxy-ethyl)-phenyl]-5-methyl-2H-pyridazin-3-one (0.8 g, 3.47 mmol) and cesium carbonate (1.12, 3.47 mmol) in N-methyl pyrrolidine (10 mL) was stirred at RT for 14 h. After completion, reaction was quenched with ice cubes and extracted with dichloromethane. Combined organic phases were concentrated under reduced pressure and purified by flash chromatography on silica to afford the title compound as a white solid (2.4 g, 92%). LC/MS: (Method A) 379.0 (M+H), RT. 3.7 min, 67.6% (Max).

Step 2: Formation of 3-(4-Methyl-6-oxo-3-{3-[2-(toluene-4-sulfonyloxy)-ethyl]phenyl}-6H-pyridazin-1-ylmethyl)-benzoic acid methyl ester

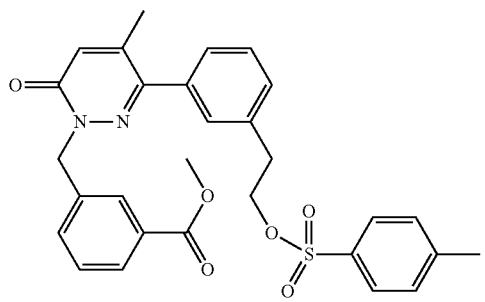 [SMILES: COC(=O)c1cccc(Cn2nc(-c3cccc(CCOS(=O)(=O)c4ccc(C)cc4)c3)c(C)cc2=O)c1]

The title compound was obtained following procedure described for intermediate 3, step from 3-{3-[3-(2-Hydroxy-ethyl)-phenyl]-4-methyl-6-oxo-6H-pyridazin-1-ylmethyl}-benzoic acid methyl ester as a brown gum (3.3 g, 99%). LC/MS: (Method A) 533.0 (M+H), RT. 5.2 min

Intermediate 15

[4-Methoxymethoxy-3-(4,4,5,5-tetramethyl-[1,3,2]dioxaborolan-2-yl)-phenyl]-methanol

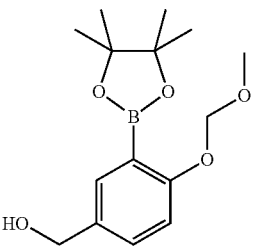 [SMILES: COCOc1ccc(CO)cc1B1OC(C)(C)C(C)(C)O1]

A mixture of (3-Bromo-4-methoxymethoxy-phenyl)-methanol (5 g, 20.2 mmol) and bis(pinacolato)diboron (5.6 g, 22.2 mmol) in 1,4-dioxane (50 mL) was degassed under $N_2$ atmosphere for 10 min, potassium acetate (3.9 g, 40.4 mmol) was added to the above followed by [1,1'-Bis(diphenylphosphino)ferrocene]dichloropalladium(II). $CH_2Cl_2$ (0.74 g, 1.01 mmol). Reaction mixture was then heated at 100° C. for 15 h. The solvent was removed under reduced pressure. The residue obtained was diluted with water and extracted in ethyl acetate (2×150 mL). Combined organic phases were washed with water, brine, dried over anhydrous $Na_2SO_4$, filtered and concentrated. Purification by the flash chromatography on silica (EtOAc:n-hexane, 70:30) afford the title compound as a brown liquid. (4 g, 67%). $^1$H NMR (400 MHz, DMSO-$d_6$): δ 7.52 (d, J=1.92 Hz, 1H), 7.31 (dd, J=8.48, 2.36 Hz, 1H), 7.01-6.95 (m, 1H), 5.15 (s, 2H), 5.07 (t, J=2.08 Hz, 1H), 4.40 (d, J=5.64 Hz, 2H), 3.93 (s, 3H), 1.16 (s, 12H).

Intermediate 16

3-{3-[2-Methoxymethoxy-5-(toluene-4-sulfonyloxymethyl)-phenyl]-6-oxo-6H-pyridazin-1-ylmethyl}-benzoic acid methyl ester

Step 1: Formation of 3-[3-(5-Hydroxymethyl-2-methoxymethoxy-phenyl)-6-oxo-6H-pyridazin-1-ylmethyl]-benzoic acid methyl ester

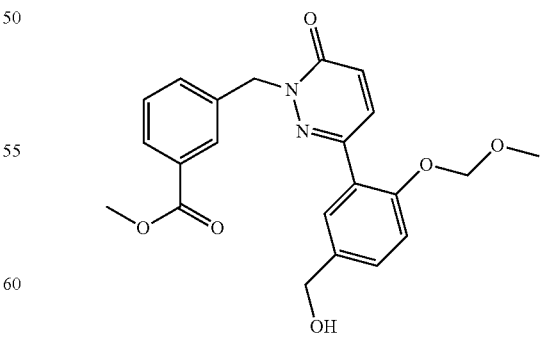

The title compound was obtained following procedure described for intermediate 11, step 1 from 3-(3-Chloro-6-oxo-6H-pyridazin-1-ylmethyl)-benzoic acid methyl ester and [4-Methoxymethoxy-3-(4,4,5,5-tetramethyl-[1,3,2]dioxaborolan-2-yl)-phenyl]-methanol as a yellow solid (2.5 g, 56%). LC/MS: (Method A) 411.2 (M+H), RT. 3.59 min.

Step 2: Formation of 3-{3-[2-Methoxymethoxy-5-(toluene-4-sulfonyloxymethyl)-phenyl]-6-oxo-6H-pyridazin-1-ylmethyl}-benzoic acid methyl ester

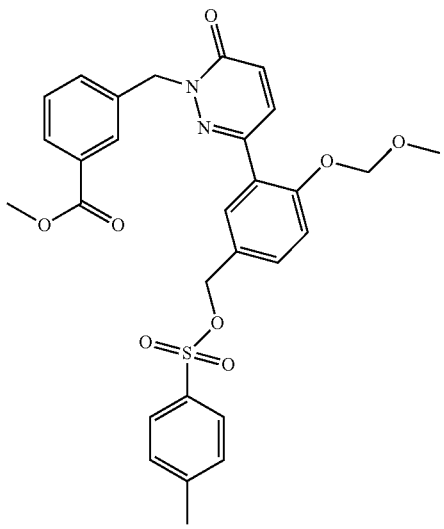

The title compound was obtained following procedure described for intermediate 3, step 2 from 3-[3-(5-Hydroxymethyl-2-methoxymethoxy-phenyl)-6-oxo-6H-pyridazin-1-ylmethyl]-benzoic acid methyl ester as a brown gum (2.5 g, 73%). LC/MS: (Method B) 564.0 (M−H), RT. 4.71 min Intermediate 17

3-[6-Oxo-3-(4,4,5,5-tetramethyl-[1,3,2]dioxaborolan-2-yl)-6H-pyridazin-1-ylmethyl]-benzoic acid methyl ester

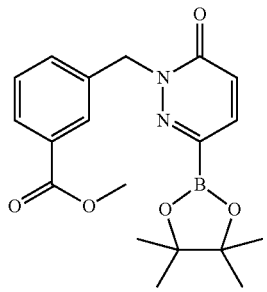 [SMILES: COC(=O)c1cccc(Cn2nc(B3OC(C)(C)C(C)(C)O3)ccc2=O)c1]

The title compound was obtained following procedure described for intermediate 10 (without flash chromatography) from 3-(3-Chloro-6-oxo-6H-pyridazin-1-ylmethyl)-benzoic acid methyl ester as a brown gum (2.0 g, 75%). LC/MS: (Method A) 289.0 (M-82), RT. 2.5 min, 75.5% (Max).

Intermediate 18

3-{3-[2-Chloro-5-(toluene-4-sulfonyloxymethyl)-phenyl]-6-oxo-6H-pyridazin-1-ylmethyl}-benzoic acid methyl ester Step 1: Formation of 3-[3-(2-Chloro-5-hydroxymethyl-phenyl)-6-oxo-6H-pyridazin-1-ylmethyl]-benzoic acid methyl ester

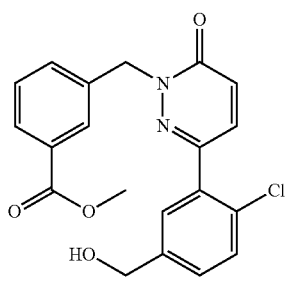 [SMILES: COC(=O)c1cccc(Cn2nc(-c3cc(CO)ccc3Cl)ccc2=O)c1]

A mixture of 3-[6-Oxo-3-(4,4,5,5-tetramethyl-[1,3,2]dioxaborolan-2-yl)-6H-pyridazin-1-ylmethyl]-benzoic acid methyl ester (2 g, 5.40 mmol), (3-Bromo-4-chloro-phenyl)-methanol (1.19 g, 5.40 mmol) and potassium carbonate (2.2 g, 16.2 mmol) in dimethylformamide/water (9:1) (50 mL) was degassed with nitrogen for 20 min. Tetrakis (triphenylphosphine) palladium (0) (0.31 g, 0.27 mmol) was added the reaction mixture was heated at 100° C. for 5 h. It was then filtered through celite, the celit5e pad was washed with dichloromethane/methanol and the filtrate concentrated under reduced pressure to afford the title compound as an off white solid (1.9 g, 915). LC/MS: (Method A) 385.0 (M+H), RT. 3.8 min, 67.0% (Max).

Step 2: Formation of 3-{3-[2-Chloro-5-(toluene-4-sulfonyloxymethyl)-phenyl]-6-oxo-6H-pyridazin-1-ylmethyl}-benzoic acid methyl ester

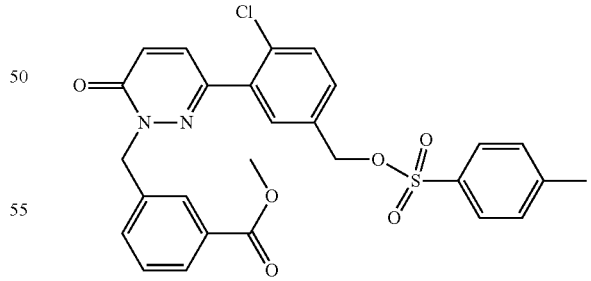

The title compound was obtained following procedure described for intermediate 3, step 2 from 3-[3-(2-Chloro-5-hydroxymethyl-phenyl)-6-oxo-6H-pyridazin-1-ylmethyl]-benzoic acid methyl ester as brown solid (2.5 g, 93%). $^1$H NMR (400 MHz, DMSO-$d_6$): δ 7.97 (s, 1H), 7.94-7.90 (m, 1H), 7.77-7.73 (m, 1H), 7.66-7.64 (m, 4H), 7.50-7.45 (m, 2H), 7.15 (d, J=1.68 Hz, 1H), 7.13-7.09 (m, 3H), 5.38 (s, 2H), 4.82 (s, 2H), 3.83 (s, 3H), 2.27 (s, 3H).

Intermediate 19

3-(6-Oxo-3-{1-[2-(toluene-4-sulfonyloxy)-ethyl]-1H-pyrazol-4-yl}-6H-pyridazin-1-ylmethyl)-benzoic acid methyl ester Step 1: Formation of 3-{3-[1-(2-Hydroxy-ethyl)-1H-pyrazol-4-yl]-6-oxo-6H-pyridazin-1-ylmethyl}-benzoic acid methyl ester

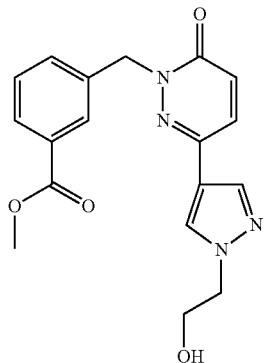 [SMILES: COC(=O)c1cccc(Cn2nc(-c3cnn(CCO)c3)ccc2=O)c1]

The title compound was obtained following procedure described for intermediate 11, step 1 from 3-(3-Chloro-6-oxo-6H-pyridazin-1-ylmethyl)-benzoic acid methyl ester and 2-[4-(4,4,5,5-Tetramethyl-[1,3,2]dioxaborolan-2-yl)-pyrazol-1-yl]-ethanol (purchased from Ark Pharma) as a pale yellow solid (2.5 g, 65%). $^1$H NMR (400 MHz, DMSO-$d_6$): δ 8.22 (s, 1H), 7.94-7.88 (m, 2H), 7.86-7.82 (m, 2H), 7.61 (d, J=7.76 Hz, 1H), 7.50 (t, J=7.68 Hz, 1H), 7.04 (d, J=9.64 Hz, 1H), 5.31 (s, 2H), 4.93 (s, 1H), 4.16 (t, J=5.52 Hz, 2H), 3.89 (s, 3H), 3.74-3.72 (m, 2H). LC/MS: (Method A) 355.2 (M+H), RT. 2.89 min, 69.8% (Max).

Step 2: Formation of 3-(6-Oxo-3-{1-[2-(toluene-4-sulfonyloxy)-ethyl]-1H-pyrazol-4-yl}-6H-pyridazin-1-ylmethyl)-benzoic acid methyl ester

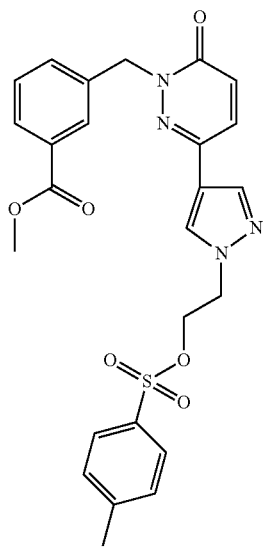 [SMILES: COC(=O)c1cccc(Cn2nc(-c3cnn(CCOS(=O)(=O)c4ccc(C)cc4)c3)ccc2=O)c1]

The title compound was obtained following procedure described for intermediate 3, step 2 from 3-{3-[1-(2-Hydroxy-ethyl)-1H-pyrazol-4-yl]-6-oxo-6H-pyridazin-1-ylmethyl}-benzoic acid methyl ester as a brown gum (3 g, 70%). LC/MS: (Method A) 509.2 (M+H), RT. 4.38 min.

Intermediate 20

[4-Methoxy-3-(4,4,5,5-tetramethyl-[1,3,2]dioxaborolan-2-yl)-phenyl]-methanol

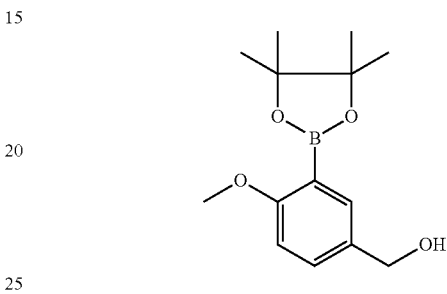

The title compound was obtained following procedure described for intermediate 10 (without flash chromatography) from (3-Bromo-4-methoxy-phenyl)-methanol as a brown gum (2.0 g, 35%). The compound was taken for next step without further purification.

Intermediate 21

3-[3-(5-Bromomethyl-2-methoxy-phenyl)-6-oxo-6H-pyridazin-1-ylmethyl]-benzoic acid methyl ester Step 1: 3-[3-(5-Hydroxymethyl-2-methoxy-phenyl)-6-oxo-6H-pyridazin-1-ylmethyl]-benzoic acid methyl ester

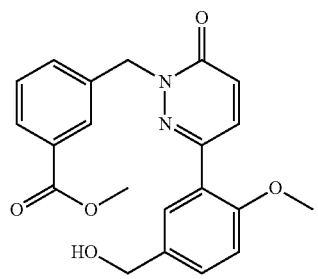

The title compound was obtained following procedure described for intermediate 11, step 1 from 3-(3-Chloro-6-oxo-6H-pyridazin-1-ylmethyl)-benzoic acid methyl ester (2.1 g, 7.57 mmol) and [4-Methoxy-3-(4,4,5,5-tetramethyl-[1,3,2]dioxaborolan-2-yl)-phenyl]-methanol as a yellow solid (2.6 g, 92%). LC/MS: (Method A) 381.0 (M+H), RT. 3.5 min, 73.8% (Max).

Step 2: 3-[3-(5-Bromomethyl-2-methoxy-phenyl)-6-oxo-6H-pyridazin-1-ylmethyl]-benzoic acid methyl ester

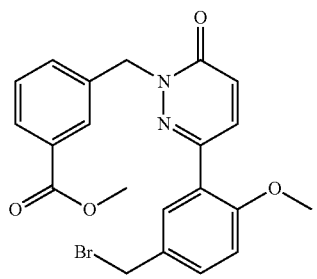 [SMILES: COC(=O)c1cccc(Cn2nc(-c3cc(CBr)ccc3OC)ccc2=O)c1]

The title compound was obtained following procedure described for intermediate 2, step from 3-[3-(5-Hydroxymethyl-2-methoxy-phenyl)-6-oxo-6H-pyridazin-1-ylmethyl]-benzoic acid methyl ester as a yellow solid (1.5 g, 51%). LC/MS: (Method A) 443.0 (M+H), RT. 4.9 min, 69.5% (Max).

Intermediate 22

3-[3-(2-Oxiranyl-ethoxy)-6-oxo-6H-pyridazin-1-ylmethyl]-benzoic acid methyl ester Step 1: 3-(3-But-3-enyloxy-6-oxo-6H-pyridazin-1-ylmethyl)-benzoic acid methyl ester

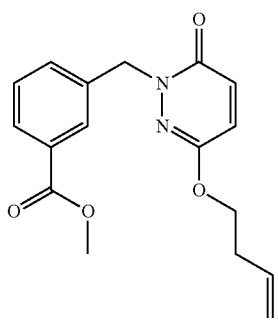 [SMILES: C=CCCOc1ccc(=O)n(Cc2cccc(C(=O)OC)c2)n1]

A solution of 3-(3-Chloro-6-oxo-6H-pyridazin-1-ylmethyl)-benzoic acid methyl ester (0.75 g, 2.69 mmol), But-3-en-1-ol (0.3 g, 4.04 mmol), palladium acetate (30 mg, 0.13 mmol) and cesium carbonate (1.3 g, 4.04 mmol) in toluene/acetonitrile (8:2, 10 mL) in a sealed tube was flushed with nitrogen for 20 min before the addition of racemic-2-di-t-butylphosphino-1,1'-binaphthyl, TrixiePhos (0.10 g, 0.26 mmol). The reaction mixture was heated at 100° C. for 10 h; cooled to RT and filtered through a celite pad. Celite was washed with dichloromethane/methanol and the filtrate was concentrated under reduced pressure. Purification by flash column chromatography on silica afforded the title compound as yellow oil (650 mg, 77%). $^1$H NMR (400 MHz, DMSO-d6): δ 7.91 (s, 1H), 7.88 (d, J=7.68 Hz, 1H), 7.58 (d, J=7.72 Hz, 1H), 7.50 (t, J=7.64 Hz, 1H), 7.19 (d, J=9.76 Hz, 1H), 6.99 (d, J=9.76 Hz, 1H), 5.84-5.77 (m, 1H), 5.16 (s, 2H), 5.11-5.02 (m, 2H), 4.12 (t, J=6.64 Hz, 2H), 3.83 (s, 3H), 2.44-2.39 (m, 2H). LC/MS: (Method A) 315 (M+H), RT. 4.4 min, 91.5% (Max), 91.7% (220 nm).

Step 2: 3-[3-(2-Oxiranyl-ethoxy)-6-oxo-6H-pyridazin-1-ylmethyl]-benzoic acid methyl ester

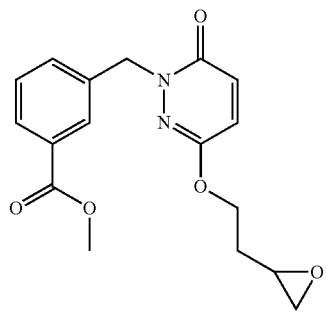 [SMILES: COC(=O)c1cccc(Cn2nc(OCCC3CO3)ccc2=O)c1]

3-Chloroperoxybenzoic acid (892 mg, 3.10 mmol) was added to a of solution 3-(3-But-3-enyloxy-6-oxo-6H-pyridazin-1-ylmethyl)-benzoic acid methyl ester (650 mg, 2.06 mmol) in dry DCM (10 mL) maintained at 0° C. The reaction mixture was warm up to RT and stirred for 14 h. It was diluted and washed with 10% sodium bicarbonate (2×10 mL), water (2×10 mL) and brine solution (2×10 mL). Combined organic layers were dried over anhydrous Na$_2$SO$_4$, filtered and concentrated. Purification by flash column chromatography on silica afforded the title compound as beige oil (550 mg, 80%). $^1$H NMR (400 MHz, DMSO-d6): δ 7.91 (s, 1H), 7.89-7.87 (m, 1H), 7.58 (d, J=7.72 Hz, 1H), 7.50 (t, J=7.60 Hz, 1H), 7.21 (d, J=9.76 Hz, 1H), 7.00 (d, J=9.72 Hz, 1H), 5.16 (s, 2H), 4.18 (t, J=6.24 Hz, 2H), 3.82 (s, 3H), 3.01-2.98 (m, 1H), 2.69-2.66 (m, 1H), 2.47-2.45 (m, 1H), 1.94-1.93 (m, 1H), 1.92-1.91 (m, 1H). LC/MS: (Method A) 331.0 (M+H), RT. 4.7 min, 71.2% (Max).

Intermediate 23

(2-methoxy-5-(4,4,5,5-tetramethyl-1,3,2-dioxaborolan-2-yl)phenyl)methanol

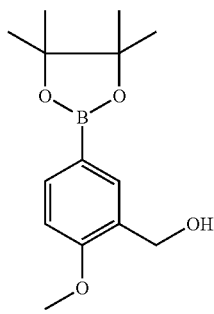 [SMILES: COc1ccc(B2OC(C)(C)C(C)(C)O2)cc1CO]

The title compound was obtained following procedure described for intermediate 10 from (5-Bromo-2-methoxyphenyl)-methanol as a brown liquid (5 g, 81%). $^1$H NMR (400 MHz, DMSO-d$_6$): δ 7.72 (s, 1H), 7.54 (dd, J=8.1, 1.5 Hz, 1H), 6.93 (d, J=8.2 Hz, 1H), 5.01 (t, J=5.5 Hz, 1H), 4.46 (d, J=4.7 Hz, 2H), 3.78 (s, 3H), 1.27 (s, 12H).

Intermediate 24

3-{3-[4-Methoxy-3-(toluene-4-sulfonyloxymethyl)-phenyl]-6-oxo-6H-pyridazin-1-ylmethyl}-benzoic acid methyl ester Step 1: 3-[3-(3-Hydroxymethyl-4-methoxy-phenyl)-6-oxo-6H-pyridazin-1-ylmethyl]-benzoic acid methyl ester

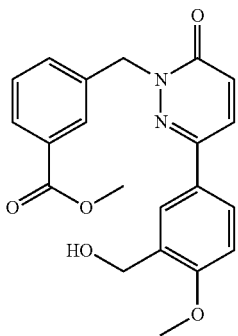 [SMILES: COC(=O)c1cccc(Cn2nc(-c3ccc(OC)c(CO)c3)ccc2=O)c1]

The title compound was obtained following procedure described for intermediate 2, step 1 from 3-(3-chloro-6-oxo-6H-pyridazin-1-ylmethyl)-benzoic acid methyl ester and (2-methoxy-5-(4,4,5,5-tetramethyl-1,3,2-dioxaborolan-2-yl)phenyl)methanol as a beige solid (1.5 g, 37%). $^1$H NMR (400 MHz, DMSO-d$_6$): δ 8.02 (d, J=9.8 Hz, 1H), 7.95 (s, 1H), 7.91-7.87 (m, 2H), 7.75 (dd, J=5.4, 2.4 Hz, 1H), 7.62 (d, J=7.7 Hz, 1H), 7.51 (t, J=7.7 Hz, 1H), 7.09-7.03 (m, 2H), 5.38 (s, 2H), 5.11 (t, J=5.7 Hz, 1H), 4.51 (d, J=5.6 Hz, 2H), 3.83 (s, 6H). LC/MS: (Method A) 381.0 (M+H), RT. 3.7 min, 92.1% (Max), 96.8% (254 nm).

Step 2: 3-{3-[4-Methoxy-3-(toluene-4-sulfonyloxymethyl)-phenyl]-6-oxo-6H-pyridazin-1-ylmethyl}-benzoic acid methyl ester

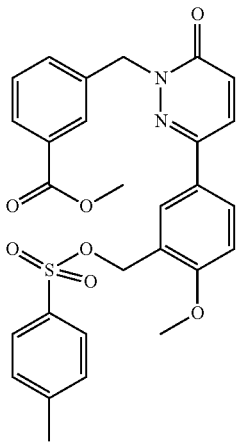 [SMILES: COC(=O)c1cccc(Cn2nc(-c3ccc(OC)c(COS(=O)(=O)c4ccc(C)cc4)c3)ccc2=O)c1]

The title compound was obtained following procedure described for intermediate 3, step from 3-[3-(3-Hydroxymethyl-4-methoxy-phenyl)-6-oxo-6H-pyridazin-1-ylmethyl]-benzoic acid methyl ester as a brown solid (1.5 g, 75%). $^1$H NMR (400 MHz, DMSO-d$_6$): δ 8.09-8.01 (m, 2H), 7.96-7.90 (m, 2H), 7.88 (d, J=10.3 Hz, 1H), 7.66 (d, J=10.3 Hz, 1H), 7.52 (d, J=10.3 Hz, 1H), 7.48-7.44 (m, 2H), 7.28 (d, J=11.8 Hz, 1H), 7.14-7.07 (m, 3H), 5.38 (s, 2H), 4.45 (s, 2H), 3.90 (s, 3H), 3.83 (s, 3H), 2.26 (s, 3H).

Intermediate 25

6-(3-Hydroxymethyl-piperidin-1-yl)-2H-pyridazin-3-one

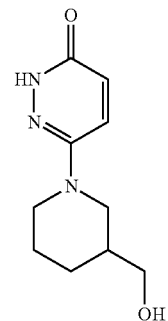 [SMILES: O=c1ccc(N2CCCC(CO)C2)n[nH]1]

A mixture of [1-(6-Chloro-pyridazin-3-yl)-piperidin-3-yl]methanol (purchased from Activate Scientific; 25 g; 0.11 mol; 1.00 eq.) and potassium acetate (33 g; 0.33 mol; 3.00 eq.) in acetic acid (75 mL) were heated in microwave for 10 min at 200° C. (Note: 3 g×10 batches). After the completion of the reaction, solvent was removed under reduced pressure. The Residue obtained was diluted with water (500 ml) and extracted with dichloromethane (10×200 mL). Combined extracts were washed with water (200 mL), brine solution (200 mL) and dried over anhydrous Na$_2$SO$_4$, filtered and concentrated to afford the intermediate 6-(3-(hydroxymethyl)piperidin-1-yl)pyridazin-3-yl acetate. It was dissolved in THF (75 mL), MeOH (50.00 mL) and Water (25.00 mL), sodium hydroxide (13.2 g; 0.33 mol; 3.00 eq.) was added and the reaction mixture was heated at 70° C. for 1 h. Solvent was removed under reduced pressure and the residue was diluted with water (200 mL), acidified with Citric acid (10% solution) to pH=2-3 and extracted in dichloromethane (5×200 mL). Combined organic phases were washed with brine solution (200 mL), dried over anhydrous Na$_2$SO$_4$, filtered and concentrated to afford the title compound as a brown gum (20 g, 87%). LC/MS: (Method A) 210.2 (M+H), RT. 2.5 min, 79.3% (Max).

Intermediate 26

3-[3-(3-Oxiranyl-piperidin-1-yl)-6-oxo-6H-pyridazin-1-ylmethyl]-benzoic acid methyl ester Step 1: 3-[3-(3-Hydroxymethyl-piperidin-1-yl)-6-oxo-6H-pyridazin-1-ylmethyl]-benzoic acid methyl ester

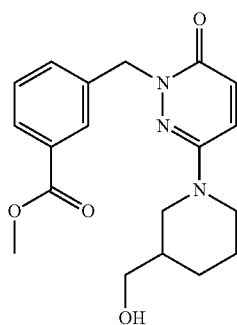 [SMILES: COC(=O)c1cccc(Cn2nc(N3CCCC(CO)C3)ccc2=O)c1]

A solution of 6-(3-Hydroxymethyl-piperidin-1-yl)-2H-pyridazin-3-one (20 g; 95.58 mmol; 1.00 eq.), Cesium carbonate (31.5 g; 95.6 mmol; 1.00 eq.) and 3-bromomethyl-benzoic acid methyl ester (21.9 g; 95.6 mmol; 1.00 eq.) in 1-Methyl-pyrrolidin-2-one (100 mL) was stirred at RT for 16 h. The reaction mixture was then treated with ice cold water (500 mL) and extracted with ethyl acetate (4×250 mL). Combined organic phases were washed with water (3×200 mL), brine solution (2×100 mL), dried over anhydrous $Na_2SO_4$, filtered and concentrated. Purification by flash chromatography on silica (EtOAc:MeOH, 99:1) afforded the title compound as yellow gum (16 g, 41%). $^1$H NMR (400 MHz, DMSO-$d_6$): δ 7.90 (s, 1H), 7.86 (dd, J=10.5, Hz, 1H), 7.57 (d, J=7.8 Hz, 1H), 7.49-6.50 (m, 2H), 5.13 (s, 2H), 4.30 (s, 1H), 3.80-3.77 (m, 4H), 3.73-3.54 (m, 1H), 3.29-3.16 (m, 2H), 2.69-2.40 (m, 1H), 2.16 (t, J=8.12 Hz, 1H), 1.94-1.82 (m, 1H), 1.70-1.62 (m, 3H), 1.55-1.40 (m, 1H), 1.18-1.09 (m, 1H). LC/MS: (Method A) 358.3 (M+H), RT. 3.4 min, 88.2% (Max). 88.6% (254 nm).

Step 2: 3-[3-(3-Formyl-piperidin-1-yl)-6-oxo-6H-pyridazin-1-ylmethyl]-benzoic acid methyl ester

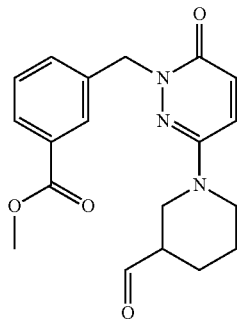 [SMILES: COC(=O)c1cccc(Cn2nc(N3CCCC(C=O)C3)ccc2=O)c1]

To a stirred solution of 33-(3-Hydroxymethyl-piperidin-1-yl)-6-oxo-6H-pyridazin-1-ylmethyl]-benzoic acid methyl ester (16 g; 39.39 mmol; 1.00 eq.) in DCM (320 mL) was added slowly, 1,1,1-Tris(acetyloxy)-1,1-dihydro-1,2-benziodoxol-3-(1H)-one (25.8 g; 59.1 mmol; 1.50 eq.), The reaction mixture was then stirred for 2 h at RT and quenched with sat. sodium thiosulphate solution (100 mL). Aqueous phase was extracted with DCM (3×250 mL). Combined organic phases were washed with water (2×200 mL), brine solution (2×100 mL), dried over anhydrous $Na_2SO_4$, filtered and concentrated. Purification by flash chromatography on silica (DCM:MeOH, 99:1) afforded the title compound as an yellow oil (16 g, 36%). LC/MS: (Method A) 356.0 (M+H), RT. 3.5 min, 71.9% (Max), 80.2% (254 nm).

Step 3: 3-[3-(3-Oxiranyl-piperidin-1-yl)-6-oxo-6H-pyridazin-1-ylmethyl]-benzoic acid methyl ester

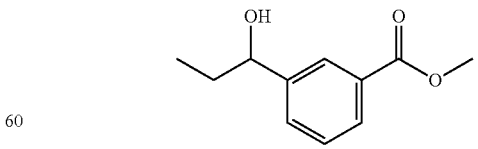

Trimethylsulfoxonium iodide (5.05 g; 22.4754 mmol; 1.50 eq.) was added to a suspension of Sodium hydride (0.90 g; 22.48 mmol; 1.50 eq.) in DMSO (112.5 mL) at 0° C. The reaction mixture was stirred for 1 h before the addition of a solution of 3-[3-(3-Formyl-piperidin-1-yl)-6-oxo-6H-pyridazin-1-ylmethyl]-benzoic acid methyl ester (7.50 g; 15 mmol; 1.00 eq.) in DMSO (37.5 mL). The resulting mixture was stirred at RT for 4 h and quenched with cold water (250 mL). It was then extracted with Ethyl acetate (5×250 mL). Combined organic phases were washed with water (3×200 mL), brine solution (2×100 mL), dried over anhydrous $Na_2SO_4$, filtered and concentrated. Purification by flash chromatography on silica (DCM:MeOH, 99:1) afforded the title compound as brown gum (2 g, 13%). LC/MS: (Method A) 370.0 (M+H), RT. 5.2 min, 36.0% (Max).

Intermediate 27

3-[1-(3-Chloro-6-oxo-6H-pyridazin-1-yl)-propyl]-benzoic acid methyl ester

Step 1: 3-(1-Hydroxy-propyl)-benzoic acid methyl ester

Sodium borohydride (1.49 g; 38.5 mmol; 1.30 eq.) was added to a stirred solution of 3-Propionyl-benzoic acid methyl ester (5.70 g; 29.65 mmol; 1.00 eq.) in dry Methanol (114 mL) at 0° C., The reaction mixture was brought back to RT and stirred for 16 h. It was quenched with water (50 mL), Methanol was removed under reduced pressure and the residue was dissolved in dichloromethane (100 mL). Organic phase was washed with water (3×50 mL), brine (2×50 mL), dried over anhydrous Na$_2$SO$_4$, filtered and concentrated. Purification by flash chromatography on silica (EtOAc:Pet.Ether, 20:80) afforded the title compound as a yellow oil (3.0 g, 52%). $^1$H NMR: (400 MHz, DMSO-d6): δ 7.93 (s, 1H), 7.82-7.80 (m, 1H), 7.57 (d, J=7.7 Hz, 1H), 7.45 (t, J=7.6 Hz, 1H), 5.28 (d, J=4.4 Hz, 1H), 4.52 (q, J=6.2 Hz, 1H), 3.84 (s, 3H), 1.64-1.57 (m, 2H), 0.80 (t, J=7.3 Hz, 3H).

Step 2: 3-(1-Bromo-propyl)-benzoic acid methyl ester

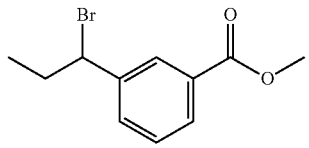

Phosphorous tribromide (1.32 mL; 13.9 mmol; 0.90 eq.) was added to a stirred solution of 3-(1-hydroxy-propyl)-benzoic acid methyl ester (3.0 g; 15.44 mmol; 1.00 eq.) in dry DCM (30 mL) at 0° C. under N$_2$ atmosphere. Reaction mixture was stirred at RT for 2 h, then poured into a cold solution NaHCO$_3$ sat. (100 mL), warmed to RT and extracted with DCM (3×50 mL). Combined organic layers were washed with brine (2×50 mL), dried over anhyd. Na$_2$SO$_4$, filtered and concentrated under reduced pressure to give the title compound as brown oil (2.62 g, 66%). 1H NMR (400 MHz, DMSO-d6): δ 8.02 (s, 1H), 7.90-7.88 (m, 1H), 7.76 (dd, J1=7.8, J2=1.2 Hz, 1H), 7.53 (t, J=7.8 Hz, 1H), 5.32 (t, J=6.8 Hz, 1H), 3.86 (s, 3H), 2.25-2.20 (m, 1H), 2.16-2.09 (m, 1H), 0.92 (t, J=7.2 Hz, 3H).

Step 3: 3-[1-(3-Chloro-6-oxo-6H-pyridazin-1-yl)-propyl]-benzoic acid methyl ester

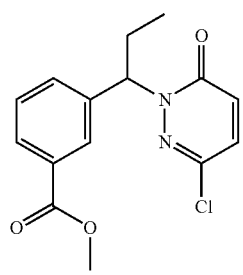 [SMILES: CCC(c1cccc(C(=O)OC)c1)n1nc(Cl)ccc1=O]

The title compound was obtained following procedure described for intermediate 26, step 1 from 6Chloro-pyridazin-3-ol (1.34 g; 10.19 mmol; 1.00 eq.) and 3-(1-Bromo-propyl)-benzoic acid methyl ester (2.62 g; 10.2 mmol; 1.00 eq.) as a brown gum. (2.50 g, 77%). 1H NMR (400 MHz, DMSO-d6): δ 7.93 (s, 1H), 7.90-7.87 (m, 1H), 7.63 (d, J=7.8 Hz, 1H), 7.56-7.50 (m, 2H), 7.06 (d, J=9.7 Hz, 1H), 5.95-5.91 (m, 1H), 3.84 (s, 3H), 2.23-2.17 (m, 1H), 2.11-2.04 (m, 1H), 0.81 (t, J=7.2 Hz, 3H). LC/MS: (Method A) 307.0 (M+H), RT. 4.5 min, 97.0% (Max), 98.0% (254 nm).

Intermediate 28

3-{1-[3-(3-Bromomethyl-phenyl)-6-oxo-6H-pyridazin-1-yl]-propyl}-benzoic acid methyl ester Step 1: 3-{1-[3-(3-Hydroxymethyl-phenyl)-6-oxo-6H-pyridazin-1-yl]-propyl}-benzoic acid methyl ester

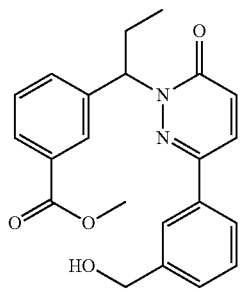 [SMILES: CCC(c1cccc(C(=O)OC)c1)n1nc(-c2cccc(CO)c2)ccc1=O]

To a briefly degassed solution of 3-[1-(3-Chloro-6-oxo-6H-pyridazin-1-yl)-propyl]-benzoic acid methyl ester (2.50 g; 7.91 mmol; 1.00 eq.) in a mixture of 1,2-Dimethoxyethane (25 mL) and Water (5 mL) was added 3-(Hydroxymethyl)phenylboronic acid (1.44 g; 9.49 mmol; 1.20 eq.), Sodium carbonate (2.57 g; 23.7 mmol; 3.00 eq.) and Bis(triphenylphosphine)palladium(II) dichloride (2.83 g; 3.95 mmol; 0.50 eq.). Reaction mixture was then heated at 110° C. for 5 h in a sealed tube. It was then cooled to RT and filtered through a celite pad. Celite was washed with MeOH/CHCl3 (1:1, 50 mL). The filtrate was concentrated under reduced pressure, diluted with DCM (100 mL), washed with water (3×50 mL) and (2×50 mL) of brine solution, dried over anhydrous Na$_2$SO$_4$, filtered and concentrated to afford the title compound as a brown gum (3.2 g, 82%). LC/MS: (Method A) 379.0 (M+H), RT. 4.1 min, 77.0% (Max), 88.0% (254 nm).

Step 2: 3-{1-[3-(3-Bromomethyl-phenyl)-6-oxo-6H-pyridazin-1-yl]-propyl}-benzoic acid methyl ester

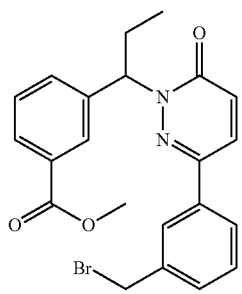 [SMILES: CCC(c1cccc(C(=O)OC)c1)n1nc(-c2cccc(CBr)c2)ccc1=O]

The title compound was obtained following procedure described for intermediate 27, step 2 from 3-{1-[3-(3-Hydroxymethyl-phenyl)-6-oxo-6H-pyridazin-1-yl]-propyl}-benzoic acid methyl ester (3.20 g; 6.5 mmol; 1.00 eq) as an off white solid (1.90 g, 64%). 1H NMR (400 MHz, DMSO-d6): δ 8.10 (s, 1H), 8.04 (t, J=9.7 Hz, 2H), 7.89 (d, J=7.7 Hz, 2H), 7.75 (d, J=7.8 Hz, 1H), 7.57-7.51 (m, 3H), 7.08 (d, J=9.8 Hz, 1H), 6.10 (t, J=6.7 Hz, 1H), 4.80 (s, 2H), 3.85 (s, 3H), 2.42-2.33 (m, 1H), 2.23-2.16 (m, 1H), 0.86 (t, J=7.20 Hz, 3H). LC/MS: (Method A) 441.0 (M+H), RT. 5.3 min, 97.0% (Max), 98.0% (254 nm).

Example 1

8,15,17,25,29-pentaazahexacyclo[23.3.1.1$^{2,6}$1$^{19,23}$0$^{8,16}$0$^{9,14}$]hentriaconta-1(29),2(31),3,5,9(14),10,12,15,19(30),20,22,27-dodecaene-18,26-dione Step 1: Methyl 3-((3-(3-((2-amino-1H-benzo[d]imidazol-1-yl)methyl)phenyl)-6-oxopyridazin-1(6H)-yl)methyl)benzoate

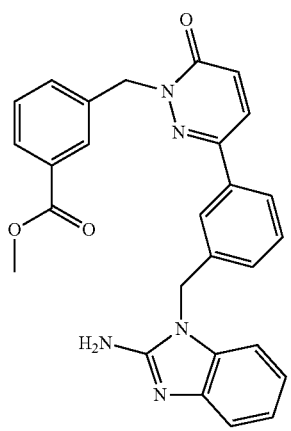 [SMILES: COC(=O)c1cccc(Cn2nc(-c3cccc(Cn4c(N)nc5ccccc54)c3)ccc2=O)c1]

A solution of methyl 3-((3-(3-(bromomethyl)phenyl)-6-oxopyridazin-1(6H)-yl)methyl)benzoate (0.5 g, 1.2 mmol), potassium carbonate (0.5 g, 3.6 mmol) and 2-amino-benzimidazole (0.05 g, 0.3 mmol) in DMF (10 mL) was heated at 75° C. for 12 h. The solvent was removed under reduced pressure and the residue was treated with water. The aqueous phase was extracted with ethyl acetate (3×15 mL) and combined organic phases were dried over anhydrous Na$_2$SO$_4$, filtered and concentrated. Purification by flash chromatography on silica of the resulting solid afforded the title compound as a brown solid (200 mg, 35%). $^1$H NMR (400 MHz, DMSO-d$_6$): δ 8.00 (d, J=9.76 Hz, 1H), 7.97 (s, 1H), 7.89 (td, J=7.64, 1.52 Hz, 1H), 7.84 (s, 1H), 7.75 (d, J=8.08 Hz, 1H), 7.60-7.58 (m, 1H), 7.53 (t, J=7.68 Hz, 1H), 7.42 (t, J=7.76 Hz, 1H), 7.19-7.07 (m, 4H), 6.92 (dt, J=7.66, 1.08 Hz, 1H), 6.84-6.80 (m, 1H), 6.62 (br s, 2H), 5.40 (s, 2H), 5.32 (s, 2H), 3.83 (s, 3H). LC/MS: (Method A) 466.2 (M+H), RT. 3.6 min, 88.0% (Max).

Step 2: Lithium 3-((3-(3-((2-amino-1H-benzo[d]imidazol-1-yl)methyl)phenyl)-6-oxopyridazin-1(6H)-yl)methyl)benzoate

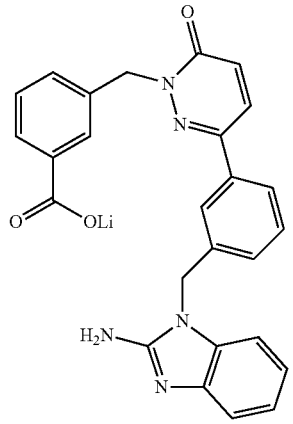

A solution of Methyl 3-((3-(3-((2-amino-1H-benzo[d]imidazol-1-yl)methyl)phenyl)-6-oxopyridazin-1(6H)-yl)methyl)benzoate (195 mg, 0.4 mmol) and Lithium hydroxide monohydrate (34 mg, 0.8 mmol) in THF:water (10 mL, 1:2) was stirred at RT for 12 h. The solvents was removed under reduced pressure and the residue was azeotroped with toluene to afford the title compound as an off-white solid (150 mg, 78%). $^1$H NMR (400 MHz, DMSO-d$_6$): δ 7.99-7.92 (m, 3H), 7.74 (t, J=8.36 Hz, 2H), 7.40 (t, J=7.80 Hz, 1H), 7.27-7.18 (m, 3H), 7.14-7.06 (m, 2H), 6.91 (t, J=7.12 Hz, 1H), 6.81 (t, J=7.60 Hz, 1H), 6.73 (s, 1H), 6.63 (br s, 2H), 5.33 (s, 2H), 5.26 (s, 2H). LC/MS: (Method A) 452.2 (M+H), RT. 3.1 min, 85.6% (Max).

Step 3: Formation of 8,15,17,25,29-pentaazahexacyclo[23.3.1.1$^{2,6}$1$^{19,23}$0$^{8,16}$0$^{9,14}$]hentriaconta-1(29),2(31),3,5,9(14),10,12,15,19(30),20,22,27-dodecaene-18,26-dione

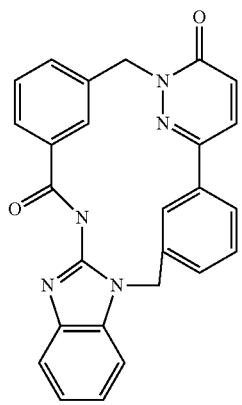 [SMILES: O=C1Nc2nc3ccccc3n2Cc2cccc(c2)-c2ccc(=O)n(n2)Cc2cccc1c2]

N-methyl morpholine (0.34 mL, 13.4 mmol) was added to a solution of Lithium 3-((3-(3-((2-amino-1H-benzo[d]imidazol-1-yl)methyl)phenyl)-6-oxopyridazin-1(6H)-yl)methyl)benzoate (150 mg, 0.33 mmol) in DMF (33 mL) maintained at 0° C. 1-hydroxy benzotriazole (49 mg, 0.36 mmol) and HBTU (144 mg, 0.38 mmol) were then added and the reaction mixture was stirred at room temperature for 15 h. It was quenched with water and the solvent were removed under reduced pressure. The resulting solid was filtrated, washed with water and purified by column chromatography on silica to give the title compound as an off-white solid (22 mg, 26%). $^1$H NMR (400 MHz, DMSO-$d_6$): δ 12.65 (br s, 1H), 9.44 (s, 2H), 8.01-7.85 (m, 3H), 7.84 (d, J=7.2 Hz, 1H), 7.66 (d, J=6.8 Hz, 1H), 7.57 (d, J=7.1 Hz, 1H), 7.49-7.42 (m, 3H), 7.31 (t, J=7.9 Hz, 1H), 7.21 (t, J=7.8 Hz, 1H), 6.99 (d, J=9.6 Hz, 1H), 5.41 (s, 4H). LC/MS: (Method A) 434.2 (M+H), RT. 4.1 min, 95.7% (Max), 95.7% (254 nm). HPLC: (Method A) RT 4.3 min, 94.8% (Max), 95.7% (254 nm).

Example 2

6,14,16,23,32-pentaazahexacyclo[24.3.1.1$^{2,6}$.1$^{8,12}$.0$^{15,23}$.0$^{17,22}$]dotriaconta-1(30),2(32),3,8,10,12(31),15,17(22),18,20,26,28-dodecaene-5,13-dione Step 1: 3-(3-{3-[2-(2-Amino-benzoimidazol-1-yl)-ethyl]-phenyl}-6-oxo-6H-pyridazin-1-ylmethyl)-benzoic acid methyl ester 2-Amino benzimidazole (0.385 g, 2.89 mmol) was added over a suspension of sodium hydride (60% dispersion in mineral oil, 138 mg, 3.47 mmol) in DMF (10 mL). The reaction mixture was heated at 60° C. for 30 min. A solution of 3-(6-Oxo-3-{3-[2-(toluene-4-sulfonyloxy)-ethyl]-phenyl}-6H-pyridazin-1-ylmethyl)-benzoic acid methyl ester (1.5 g, 2.89 mmol) in DMF (10 mL) was added drop wise while and the reaction mixture was heated at 100° C. for 12 h. DMF was removed under reduced pressure, the residue obtained was treated with water and extracted with ethyl acetate (3×15 mL). Combined organic phases were dried over anhydrous Na$_2$SO$_4$, filtered and concentrated. Purification of this crude by flash chromatography on silica afforded the title compound as a yellow solid (1.5 g, 41%). LC/MS: (Method A) 480.3 (M+H), RT. 3.75 min.

Step 2: Formation of Lithium 3-(3-{3-[2-(2-Amino-benzoimidazol-1-yl)-ethyl]-phenyl}-6-oxo-6H-pyridazin-1-ylmethyl)-benzoate

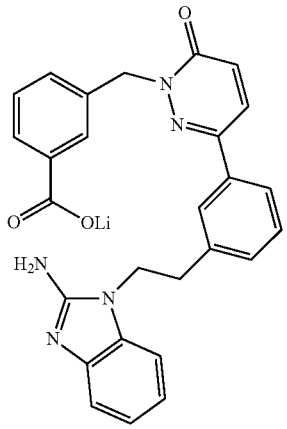

The title compound was obtained following procedure described for example 1, step 2 as a yellow solid (1.4 g, 98%). LC/MS: (Method A) 466.2 (M+H), RT. 3.28 min.

Step 3: Formation of 6,14,16,23,32-pentaaza-hexacyclo[24.3.1.1$^{2,6}$.1$^{8,12}$.0$^{18,23}$.0$^{17,22}$]dotriaconta-1(30),2(32),3,8,10,12(31),15,17(22),18,20,26,28-dodecaene-5,13-dione

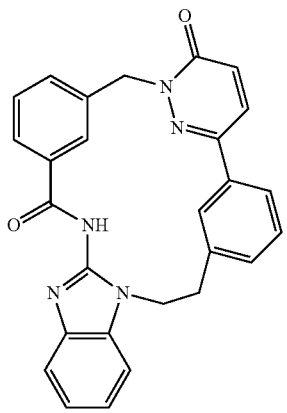 [SMILES: O=C1Nc2nc3ccccc3n2CCc2cccc(c2)-c2ccc(=O)n(n2)Cc2cccc1c2]

The title compound was obtained following procedure described for example 1, step 3 as an off-white solid (300 mg, 33%). $^1$H NMR (400 MHz, DMSO-$d_6$): δ 12.78 (s, 1H), 9.10 (s, 1H), 8.46 (s, 1H), 8.04 (d, J=8.1 Hz, 1H), 7.95 (d, J=9.6 Hz, 1H), 7.71 (t, J=7.6 Hz, 2H), 7.56 (d, J=7.9 Hz, 2H), 7.47-7.36 (m, 3H), 7.32-7.25 (m, 2H), 7.05 (d, J=9.8 Hz, 1H), 5.38 (s, 2H), 4.68 (d, J=6.9 Hz, 2H) 3.04 (s, 2H). LC/MS: (Method A) 448.2 (M+H), RT. 4.52 min, 95.94% (Max), 93.93% (254 nm). HPLC: (Method A) RT. 4.53 min, 94.06% (Max), 94.0% (254 nm).

Example 3a and 3b

2-{18,26-dioxo-8,15,17,25,29-pentaazahexacyclo[23.3.1.1$^{2,6}$.1$^{19,23}$.0$^{8,16}$.0$^{9,14}$]hentriaconta-1(29),2(31),3,5,9(14),10,12,15,19(30),20,22,27-dodecaen-11-yl}-N,N-dimethylacetamide and 2-{18,26-dioxo-8,15,17,25,29-pentaazahexacyclo[23.3.1.1$^{2,6}$.1$^{19,23}$.0$^{8,16}$.0$^{9,14}$]hentriaconta-1(29),2(31),3,5,9(14),10,12,15,19(30),20,22,27-dodecaen-12-yl}-N,N-dimethylacetamide

Step 1: Formation of 3-{3-[3-(2-Amino-6-dimethylcarbamoylmethyl-benzoimidazol-1-ylmethyl)-phenyl]-6-oxo 6H-pyridazin-1-ylmethyl}-benzoic acid methyl ester and 3-{3-[3-(2-Amino-5-dimethylcarbamoylmethyl-benzoimidazol-1-ylmethyl)-phenyl]-6-oxo-6H-pyridazin-1-ylmethyl}-benzoic acid methyl ester

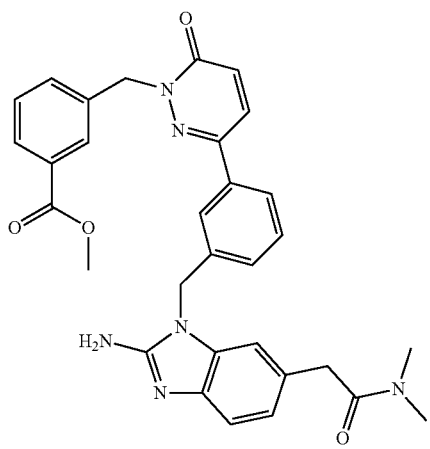 [SMILES: COC(=O)c1cccc(Cn2nc(-c3cccc(Cn4c(N)nc5ccc(CC(=O)N(C)C)cc54)c3)ccc2=O)c1]

The title compounds were obtained from methyl 3-((3-(3-(bromomethyl)phenyl)-6-oxopyridazin-1(6H)-yl)methyl)benzoate and 2-(2-amino-1H-benzo[d]imidazol-5-yl)-N,N-dimethylacetamide as a mixture of regioisomers following procedure described for example 1, step 1 as a brown solid (500 mg, 34%). LC/MS: (Method A) 551.2 (M+H), RT. 3.31, 3.39 min.

Step 2: Formation of Lithium 3-{3-[3-(2-Amino-6-dimethylcarbamoylmethyl-benzoimidazol-1-ylmethyl)-phenyl]-6-oxo-6H-pyridazin-1-ylmethyl}-benzoate and Lithium 3-{3-[3-(2-Amino-5-dimethylcarbamoylmethyl-benzoimidazol-1-ylmethyl)-phenyl]-6-oxo-6H-pyridazin-1-ylmethyl}-benzoate

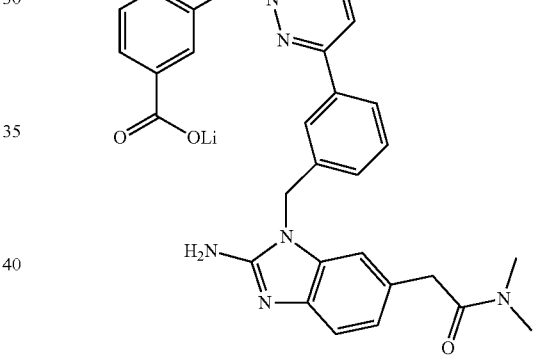

The title compounds were obtained from the mixture of 3-{3-[3-(2-Amino-6-dimethylcarbamoylmethyl-benzoimidazol-1-ylmethyl)-phenyl]-6-oxo 6H-pyridazin-1-ylmethyl}-benzoic acid methyl ester and 3-{3-[3-(2-Amino-5-dimethylcarbamoylmethyl-benzoimidazol-1-ylmethyl)-phenyl]-6-oxo-6H-pyridazin-1-ylmethyl}-benzoic acid methyl ester as a mixture of regioisomers following procedure described for example 1, step 2 as a yellow solid (500 mg, 98%). LC/MS: (Method A) 537.3 (M+H), RT. 2.81, 2.90 min.

Step 3: Formation of 2-{18,26-dioxo-8,15,17,25,29-pentaazahexacyclo[23.3.1.1$^{2,6}$.1$^{19,23}$.0$^{8,16}$.0$^{9,14}$]hentriaconta-1(29),2(31),3,5,9(14),10,12,15,19(30),20,22,27-dodecaen-11-yl}-N,N-dimethylacetamide and 2-{18,26-dioxo-8,15,17,25,29-pentaazahexacyclo[23.3.1.1$^{2,6}$.1$^{19,23}$.0$^{8,16}$.0$^{9,14}$]hentriaconta-1(29),2(31),3,5,9(14),10,12,15,19(30),20,22,27-dodecaen-12-yl}-N, N-dimethylacetamide

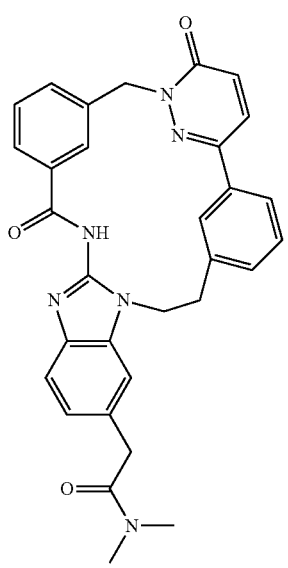

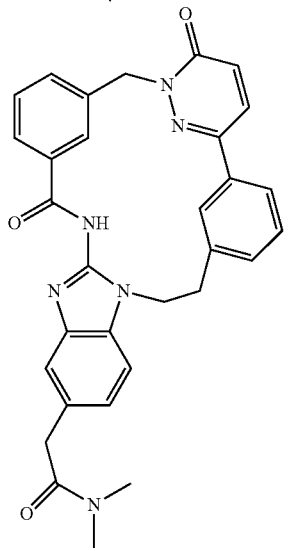

The title compounds were obtained from the mixture of Lithium 3-{3-[3-(2-Amino-6-dimethylcarbamoylmethyl-benzoimidazol-1-ylmethyl)-phenyl]-6-oxo-6H-pyridazin-1-ylmethyl}-benzoate and Lithium 3-{3-[3-(2-Amino-5-dimethylcarbamoylmethyl-benzoimidazol-1-ylmethyl)-phenyl]-6-oxo-6H-pyridazin-1-ylmethyl}-benzoate as a mixture of regioisomers following procedure described for example 1, step 3 as an off-white solid (57 mg, 15%). $^1$H NMR (400 MHz, DMSO-d$_6$): 400 MHz, DMSO-d6: δ 12.59 (s, 1H), 9.42 (s, 2H), 8.04-8.00 (m, 2H), 7.91-7.82 (m, 2H), 7.66-7.55 (m, 2H), 7.45-7.32 (m, 3H), 7.10 (m, 1H), 6.99 (d, J=9.72 Hz, 1H), 5.42-5.38 (m, 4H), 3.84 (s, 2H), 3.08 (s, 3H), 2.87 (s, 3H). LC/MS: (Method A) 519.2 (M+H), RT. 3.56, 3.62 min, HPLC: (Method A) RT. 3.54, 3.60 min, 51.8, 46.3% (Max), 53.5, 44.6% % (254 nm). The two isomers were separated by PREP HPLC using a Chiralpak column (250×20 mm; 5 u) with MeOH:THF:DEA 80:20:0.1 as eluent. First eluting compound: 14.37 min (ex. 3a); second eluting compound: 17.49 min (ex.3b).

Example 4

28-Methyl-8,15,17,25,29-pentaazahexacyclo[23.3.1.1$^{2,6}$1$^{19,233}$0$^{8,16}$0$^{9,14}$]hentriaconta-1(29),2(31),3,5,9(14),10,12,15,19(30),20,22,27-dodecaene-18,26-dione Step 1: 3-{3-[3-(2-Amino-benzoimidazol-1-ylmethyl)-phenyl]-4-methyl-6-oxo-6H-pyridazin-1-ylmethyl}-benzoic acid methyl ester

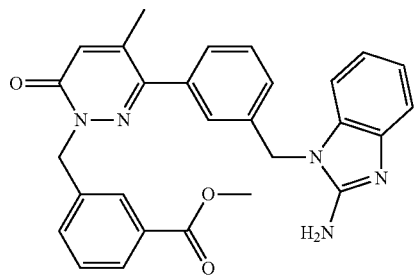 [SMILES: COC(=O)c1cccc(Cn2nc(-c3cccc(Cn4c(N)nc5ccccc54)c3)c(C)cc2=O)c1]

The title compound was obtained following procedure described for example 1, step 1 from 3-[3-(3-Bromomethyl-phenyl)-4-methyl-6-oxo-6H-pyridazin-1-ylmethyl]-benzoic acid methyl ester and 2-Amino benzimidazole as a brown solid (300 mg, 27%). $^1$H NMR (400 MHz, DMSO-d$_6$): δ 7.93 (s, 1H), 7.88 (d, J=1.60 Hz, 1H), 7.55-7.52 (m, 2H), 7.44-7.40 (m, 1H), 7.36 (d, J=7.72 Hz, 1H), 7.30 (s, 1H), 7.26 (d, J=7.60 Hz, 1H), 7.15 (d, J=7.72 Hz, 1H), 7.11 (d, J=7.60 Hz, 1H), 6.96-6.92 (m, 2H), 6.84 (t, J=6.76 Hz, 1H), 6.69 (br s, 2H), 5.32 (s, 2H), 5.28 (s, 2H), 3.83 (s, 3H), 2.02 (s, 3H). LC/MS: (Method A) 480.2 (M+H), RT. 3.62 min, 90.12% (Max).

Step 2: Formation of Lithium 3-{3-[3-(2-Amino-benzoimidazol-1-ylmethyl)-phenyl]-4-methyl-6-oxo-6H-pyridazin-1-ylmethyl}-benzoate

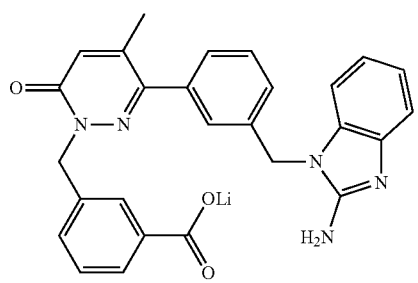

The title compound was obtained following procedure described for example 1, step 2 as a yellow solid (300 mg, 98%). LC/MS: (Method A) 466.2 (M+H), RT. 3.24 min.

Step 3: Formation of 28-Methyl-8,15,17,25,29-pentaazahexacyclo[23.3.1.1²,⁶1¹⁹,²³0⁸,¹⁶0⁹,¹⁴]hentriaconta-1(29),2(31),3,5,9(14),10,12,15,19(30),20,22,27-dodecaene-18,26-dione

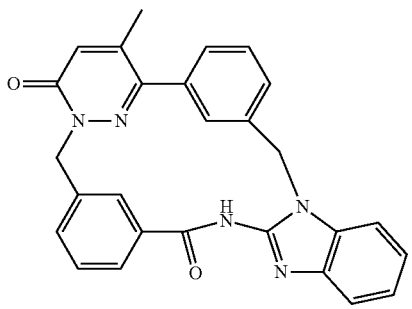 [SMILES: Cc1cc(=O)n2nc1-c1cccc(c1)Cn1c(nc3ccccc31)NC(=O)c1cccc(c1)C2]

The title compound was obtained following procedure described for example 2, step 3 from Lithium 3-{3-[3-(2-Amino-benzoimidazol-1-ylmethyl)-phenyl]-4-methyl-6-oxo-6H-pyridazin-1-ylmethyl}-benzoate as a brown solid (79 mg, 29%). $^1$H NMR (400 MHz, DMSO-$d_6$): δ 12.54 (s, 1H), 9.30 (s, 1H), 9.18 (s, 1H), 8.00 (d, J=7.76 Hz, 1H), 7.83-7.80 (m, 2H), 7.73 (d, J=7.96 Hz, 1H), 7.56 (d, J=7.36 Hz, 1H), 7.47-7.43 (m, 3H), 7.26 (t, J=7.52 Hz, 1H), 7.19 (t, J=7.44 Hz, 1H), 6.78 (s, 1H), 5.36 (s, 4H), 2.24 (s, 3H). LC/MS: (Method A) 448.2 (M+H), RT. 3.94 min, 94.78% (Max), 95.53% (254 nm). HPLC: (Method A) RT. 4.15 min, 98.18% (Max), 98.47% (254 nm).

Example 5

11,12-dimethoxy-8,15,17,25,29-pentaazahexacyclo[23.3.1.1²,⁶.1¹⁹,²³.0⁸,¹⁶.0⁹,¹⁴]hentriaconta-1(29),2(31),3,5,9(14),10,12,15,19(30),20,22,27-dodecaene-18,26-dione Step 1: Formation of 3-{3-[3-(2-Amino-5,6-dimethoxy-benzoimidazol-1-ylmethyl)-phenyl]-6-oxo-6H-pyridazin-1-ylmethyl}-benzoic acid methyl ester

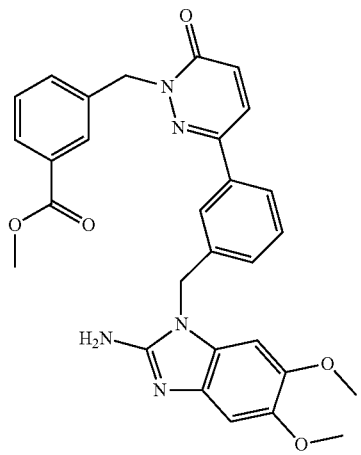 [SMILES: COC(=O)c1cccc(Cn2nc(-c3cccc(Cn4c(N)nc5cc(OC)c(OC)cc54)c3)ccc2=O)c1]

The title compound was obtained following procedure described for example 1, step 1 from Methyl 3-((3-(3-(bromomethyl)phenyl)-6-oxopyridazin-1(6H)-yl)methyl) benzoate and 5,6-dimethoxy-1H-benzimidazol-2-amine as a brown solid (500 mg, 44%). LC/MS: (Method A) 526.2 (M+H), RT. 3.54 min.

Step 2: Formation of Lithium 3-{3-[3-(2-Amino-5,6-dimethoxy-benzoimidazol-1-ylmethyl)-phenyl]-6-oxo-6H-pyridazin-1-ylmethyl}-benzoate

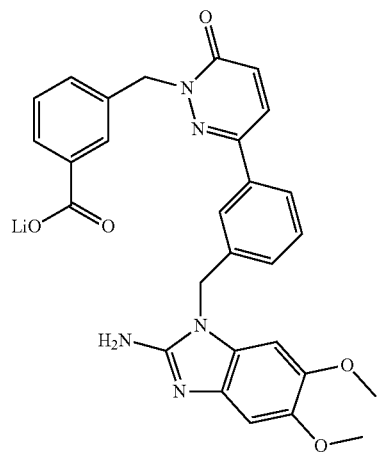

The title compound was obtained following procedure described for example 1, step 2 from 3-{3-[3-(2-Amino-5,6-dimethoxy-benzoimidazol-1-ylmethyl)-phenyl]-6-oxo-6H-pyridazin-1-ylmethyl}-benzoic acid methyl ester as a brown solid (500 mg, 98%). LC/MS: (Method A) 512.3 (M+H), RT. 3.05 min.

Step 3: Formation of 11,12-dimethoxy-8,15,17,25,29-pentaazahexacyclo[23.3.1.1²,⁶.1¹⁹,²³.0⁸,¹⁶.0⁹,¹⁴]hentriaconta-1(29),2(31),3,5,9(14),10,12,15,19(30),20,22,27-dodecaene-18,26-dione

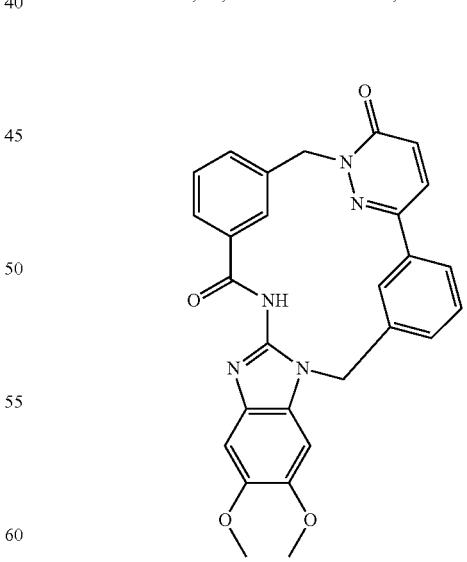

The title compound was obtained following procedure described for example 1, step 3 from Lithium 3-{3-[3-(2-Amino-5,6-dimethoxy-benzoimidazol-1-ylmethyl)-phenyl]-6-oxo-6H-pyridazin-1-ylmethyl}-benzoate as a yellow solid (33 mg, 13%). $^1$H NMR (400 MHz, DMSO-$d_6$): δ 12.54 (s, 1H), 9.41 (s, 2H), 8.04-7.98 (m, 2H), 7.83 (d, J=7.5 Hz, 1H), 7.69 (d, J=5.9 Hz, 2H), 7.54 (d, J=7.3 Hz, 1H), 7.44-7.37 (m, 2H), 7.14 (s, 1H), 6.99 (d, J=9.7 Hz, 1H), 5.40 (s, 4H), 3.93 (s, 3H), 3.74 (s, 3H). LC/MS: (Method A) 494.0 (M+H), RT. 3.63 min, 95.04% (Max), 95.74% (254 nm). HPLC: (Method A) RT. 3.61 min, 94.62% (Max), 95.67% (254 nm).

Example 6

11,12-difluoro-8,15,17,25,29-pentaazahexacyclo[23.3.1.1$^{2,6}$.1$^{19,23}$.0$^{8,16}$.0$^{9,14}$]hentriaconta-1(29),2(31),3,5,9(14),10,12,15,19(30),20,22,27-dodecaene-18,26-dione Step 1: 3-{3-[3-(2-Amino-5,6-difluoro-benzoimidazol-1-ylmethyl)-phenyl]-6-oxo-6H-pyridazin-1-ylmethyl}-benzoic acid methyl ester

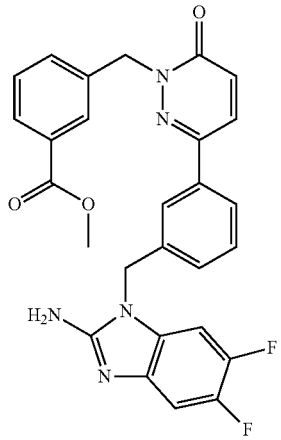 [SMILES: COC(=O)c1cccc(Cn2nc(-c3cccc(Cn4c(N)nc5cc(F)c(F)cc54)c3)ccc2=O)c1]

The title compound was obtained following procedure described for example 1, step 1 from Methyl 3-((3-(3-(bromomethyl)phenyl)-6-oxopyridazin-1(6H)-yl)methyl) benzoate as a brown solid (400 mg, 24%). LC/MS: (Method A) 502.3 (M+H), RT. 4.13 min.

Step 2: Formation of Lithium 3-{3-[3-(2-Amino-5,6-difluoro-benzoimidazol-1-ylmethyl)-phenyl]-6-oxo-6H-pyridazin-1-ylmethyl}-benzoate

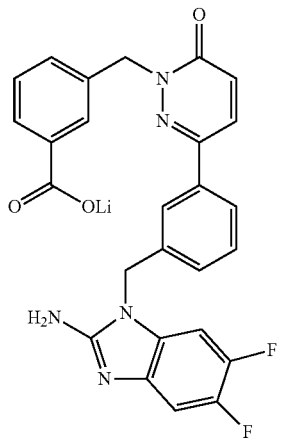

The title compound was obtained following procedure described for example 1, step 2 from 3-{3-[3-(2-Amino-5,6-difluoro-benzoimidazol-1-ylmethyl)-phenyl]-6-oxo-6H-pyridazin-1-ylmethyl}-benzoic acid methyl ester (400 mg, 98%). LC/MS: (Method A) 488.3 (M+H), RT. 3.40 min.

Step 3: Formation of 11,12-difluoro-8,15,17,25,29-pentaazahexacyclo[23.3.1.1$^{2,6}$.1$^{19,23}$.0$^{8,16}$.0$^{9,14}$]hentriaconta-1(29),2(31),3,5,9(14),10,12,15,19(30),20,22,27-dodecaene-18,26-dione

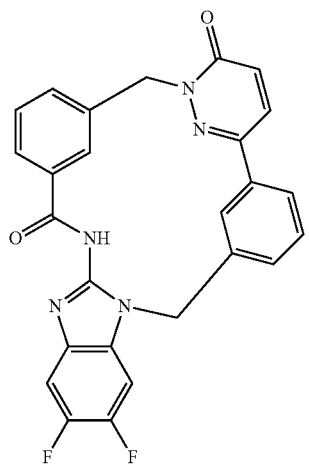 [SMILES: O=C1Nc2nc3cc(F)c(F)cc3n2Cc2cccc(c2)-c2ccc(=O)n(n2)Cc2cccc1c2]

The title compound was obtained following procedure described for example 1, step 3 from Lithium 3-{3-[3-(2-Amino-5,6-difluoro-benzoimidazol-1-ylmethyl)-phenyl]-6-oxo-6H-pyridazin-1-ylmethyl}-benzoate as an off-white solid (65 mg, 24%). $^1$H NMR (400 MHz, DMSO-d$_6$): δ 12.75 (s, 1H), 9.41 (d, J=4.5 Hz, 2H), 8.32 (m, 1H), 8.04-7.99 (m, 2H), 7.85 (d, J=7.7 Hz, 1H), 7.72 (d, J=7.5 Hz, 1H), 7.58 (d, J=7.5 Hz, 1H), 7.46-7.40 (m, 3H), 7.00 (d, J=9.6 Hz, 1H), 5.37 (s, 4H). LC/MS: (Method A) 470.0 (M+H), RT. 4.61 min, 93.16% (Max), 91.23% (254 nm). HPLC: (Method A) RT. 4.53 min, 93.7% (Max), 93.2% (254 nm).

Example 7

4,8,15,17,25,29-hexaazahexacyclo[23.3.1.1$^{2,6}$.1$^{19,23}$.0$^{8,16}$.0$^{9,14}$]hentriaconta-1(29),2(31),3,5,9(14),10,12,15,19(30),20,22,27-dodecaene-18,26-dione

Step 1: 3-{3-[5-(2-Amino-benzoimidazol-1-ylmethyl)-pyridin-3-yl]-6-oxo-6H-pyridazin-1ylmethyl}-benzoic acid methyl ester

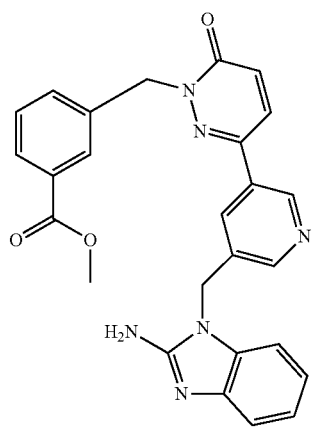 [SMILES: COC(=O)c1cccc(Cn2nc(-c3cncc(Cn4c(N)nc5ccccc54)c3)ccc2=O)c1]

The title compound was obtained following procedure described for example 2, step 1 from 2-amino benzimidazole and 3-{6-Oxo-3-[5-(toluene-4-sulfonyloxymethyl)-pyridin-3-yl]-6H-pyridazin-1-ylmethyl}-benzoic acid methyl ester as a beige solid (400 mg, 30%). $^1$H NMR (400 MHz, DMSO-d$_6$): δ 8.97 (d, J=2.08 Hz, 1H), 8.49 (d, J=1.96 Hz, 1H), 8.13 (d, J=2.04 Hz, 1H), 8.07 (d, J=9.80 Hz, 1H), 7.96 (s, 1H), 7.89 (d, J=7.60 Hz, 1H), 7.56-7.54 (m, 1H), 7.52-7.50 (m, 1H), 7.21-7.15 (m, 3H), 7.13 (s, 1H), 7.01-6.97 (m, 1H), 6.90-6.86 (m, 2H), 5.39 (s, 2H), 5.34 (s, 2H), 3.83 (s, 3H). LC/MS: (Method A) 467.2 (M+H), RT. 3.03 min, 80.03% (Max), 84.1% (254 nm).

Step 2: Formation of Lithium 3-{3-[5-(2-Amino-benzoimidazol-1-ylmethyl)-pyridin-3-yl]-6-oxo-6H-pyridazin-1ylmethyl}-benzoate

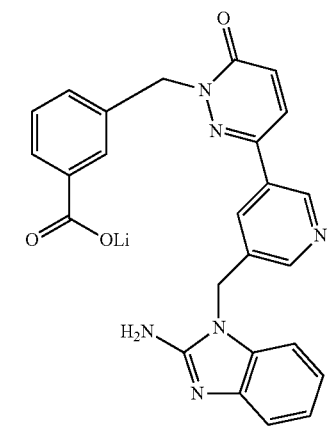

The title compound was obtained following procedure described for example 1, step 2 from 3-{3-[5-(2-Amino-benzoimidazol-1-ylmethyl)-pyridin-3-yl]-6-oxo-6H-pyridazin-1ylmethyl}-benzoic acid methyl ester as a beige solid (400 mg, 98%). LC/MS: (Method A) 453.3 (M+H), RT. 2.63 min, 83.32% (Max), 69.3% (254 nm).

Step 3: Formation of 4,8,15,17,25,29-hexaazahexacyclo[23.3.1.1$^{2,6}$.1$^{19,23}$.0$^{8,16}$.0$^{9,14}$]hentriaconta-1(29),2(31),3,5,9(14),10,12,15,19(30),20,22,27-dodecaene-18,26-dione

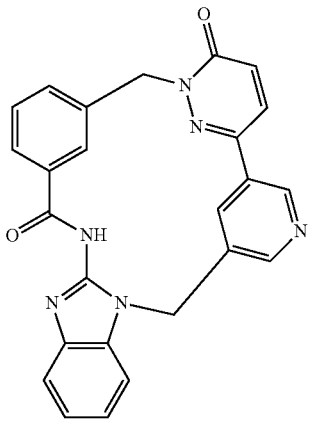 [SMILES: O=C1Nc2nc3ccccc3n2Cc2cncc(c2)-c2ccc(=O)n(n2)Cc2cccc1c2]

The title compound was obtained following procedure described for example 1, step 3 from lithium 3-{3-[5-(2-Amino-benzoimidazol-1-ylmethyl)-pyridin-3-yl]-6-oxo-6H-pyridazin-1ylmethyl}benzoate as an off-white solid (129 mg, 25%). $^1$H NMR (400 MHz, DMSO-d$_6$): δ 12.69 (s, 1H), 9.78 (s, 1H), 9.33 (s, 1H), 9.07 (d, J=1.76 Hz, 1H), 8.87 (s, 1H), 8.14 (d, J=9.72 Hz, 1H), 8.05-8.00 (m, 2H), 7.57 (d, J=7.24 Hz, 1H), 7.48 (d, J=7.80 Hz, 1H), 7.42 (t, J=7.48 Hz, 1H), 7.33 (t, J=7.84 Hz, 1H), 7.22 (t, J=7.68 Hz, 1H), 7.04 (d, J=9.68 Hz, 1H), 5.47 (s, 4H). LC/MS: (Method A) 435.0 (M+H), RT. 4.48 min, 98.26% (Max), 98.94% (254 nm). HPLC: (Method A) RT. 3.00 min, 97.8% (Max), 97.8% (254 nm).

Example 8

3-Methyl-8,15,17,25,29-pentaazahexacyclo[23.3.1.1$^{2,6}$1$^{19,23}$0$^{8,16}$0$^{9,14}$]hentriaconta-1(29),2(31),3,5,9(14),10,12,15,19(30),20,22,27-dodecaene-18,26-dione

Step 1: Formation of 3-{3-[5-(2-Amino-benzoimidazol-1-ylmethyl)-2-methyl-phenyl]-6-oxo-6H-pyridazin-1-ylmethyl}-benzoic acid methyl ester

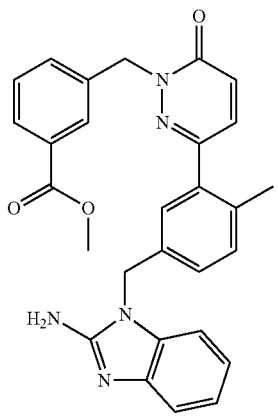 [SMILES: COC(=O)c1cccc(Cn2nc(-c3cc(Cn4c(N)nc5ccccc54)ccc3C)ccc2=O)c1]

The title compound was obtained following procedure described for example 1, step 1 from -[3-(5-Bromomethyl-2-methyl-phenyl)-6-oxo-6H-pyridazin-1-ylmethyl]-benzoic acid methyl ester and 2-amino-benzimidazole as a yellow solid (1.0 g, 47%). LC/MS: (Method A) 480.2 (M+H), RT. 3.79 min.

Step 2: Formation of Lithium 3-{3-[5-(2-Amino-benzoimidazol-1-ylmethyl)-2-methyl-phenyl]-6-oxo-6H-pyridazin-1-ylmethyl}-benzoate

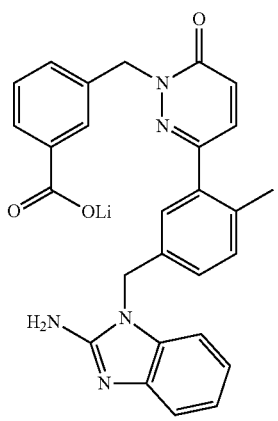

The title compound was obtained following procedure described for example 1, step 2 from 3-{3-[5-(2-Amino-benzoimidazol-1-ylmethyl)-2-methyl-phenyl]-6-oxo-6H-pyridazin-1-ylmethyl}-benzoic acid methyl ester as a yellow solid (100 mg, 98%). LC/MS: (Method A) 466.3 (M+H), RT. 3.32 min.

Step 3: Formation of 3-Methyl-8,15,17,25,29-pentaazahexacyclo[23.3.1.1$^{2,6}$1$^{19,23}$0$^{8,16}$0$^{9,14}$]hentriaconta-1(29),2(31),3,5,9(14),10,12,15,19(30),20,22,27-dodecaene-18,26-dione

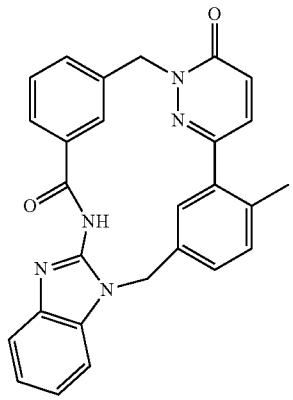 [SMILES: Cc1ccc2cc1-c1ccc(=O)n(n1)Cc1cccc(c1)C(=O)Nc1nc3ccccc3n1C2]

The title compound was obtained following procedure described for example 1, step 3 from Lithium 3-{3-[5-(2-Amino-benzoimidazol-1-ylmethyl)-2-methyl-phenyl]-6-oxo-6H-pyridazin-1-ylmethyl}-benzoate as an off-white solid (19 mg, 13%). $^1$H NMR (400 MHz, DMSO-d$_6$): δ 12.52 (s, 1H), 9.20 (s, 1H), 9.09 (s, 1H), 7.98 (d, J=7.84 Hz, 1H), 7.80 (d, J=7.76 Hz, 1H), 7.74 (d, J=9.60 Hz, 2H), 7.59 (d, J=7.32 Hz, 1H), 7.47-7.42 (m, 2H), 7.31-7.23 (m, 2H), 7.18 (t, J=7.48 Hz, 1H), 6.91 (d, J=9.68 Hz, 1H), 5.38 (s, 4H), 2.42 (s, 3H). LC/MS: (Method A) 448.0 (M+H), RT. 4.19 min, 94.2% (Max), 95.2% (254 nm).

Example 9

26-oxa-6,14,16,23,33-pentaazahexacyclo[25.3.1.1$^{2,6}$.1$^{8,12}$]0$^{15,23}$.0$^{17,22}$]tritriaconta-1(31),2(33),3,8,10,12(32),15,17,19,21,27,29-dodecaene-5,13-dione

Step 1: Formation of 3-(3-{3-[2-(2-Amino-benzoimidazol-1-yl)-ethoxy]-phenyl}-6-oxo-6H-pyridazin-1-ylmethyl)-benzoic acid methyl ester

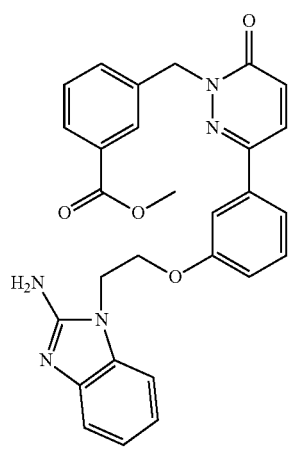 [SMILES: COC(=O)c1cccc(Cn2nc(-c3cccc(OCCn4c(N)nc5ccccc54)c3)ccc2=O)c1]

The title compound was obtained following procedure described for example 2, step 1 from 2-amino benzimidazole and 3-(6-Oxo-3-{3-[2-(toluene-4-sulfonyloxy)-ethoxy]-phenyl}-6H-pyridazin-1-ylmethyl)-benzoic acid methyl ester as a brown solid (1 g, 40%). LC/MS: (Method A) 496.2 (M+H), RT. 3.8 min.

Step 2: Formation of Lithium3-(3-{3-[2-(2-Amino-benzoimidazol-1-yl)-ethoxy]phenyl}-6-oxo-6H-pyridazin-1-ylmethyl)-benzoate

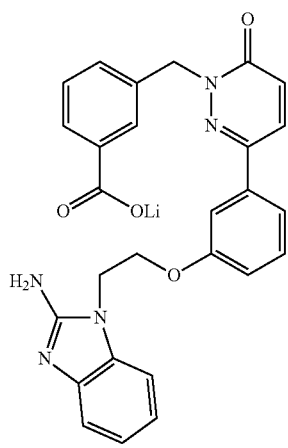

The title compound was obtained following procedure described for example 1, step 2 from 3-(3-{3-[2-(2-Amino-benzoimidazol-1-yl)-ethoxy]-phenyl}-6-oxo-6H-pyridazin-1-ylmethyl)-benzoic acid methyl ester as a brown solid (450 mg, 94/). LC/MS: (Method A) 482.2 (M+H), RT. 3.3 min.

Step 3: Formation of 26-oxa-6,14,16,23,33-pentaazahexacyclo[25.3.1.1$^{2,6}$.1$^{8,12}$]0$^{15,23}$.0$^{17,22}$]tritriaconta-1(31),2(33),3,8,10,12(32),15,17,19,21,27,29-dodecaene-5,13-dione

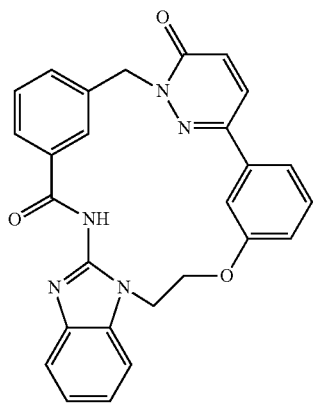 [SMILES: O=C1Nc2nc3ccccc3n2CCOc2cccc(c2)-c2ccc(=O)n(n2)Cc2cccc1c2]

The title compound was obtained following procedure described for example 1, step 3 from Lithium 3-(3-{3-[2-(2-Amino-benzoimidazol-1-yl)-ethoxy]-phenyl}-6-oxo-6H-pyridazin-1-ylmethyl)-benzoate as an off-white solid (46 mg, 20%). $^1$H NMR (400 MHz, DMSO-d6): δ 12.89 (s, 1H), 8.89 (s, 1H), 8.05 (d, J=7.76 Hz, 1H), 7.95 (d, J=9.72 Hz, 1H), 7.80 (s, 1H), 7.66-7.63 (m, 2H), 7.56 (d, J=6.72 Hz, 1H), 7.50-7.42 (m, 3H), 7.32-7.24 (m, 2H), 7.11-7.04 (m, 2H), 5.35 (s, 2H), 4.64-4.60 (m, 2H), 4.46-4.42 (m, 2H). LC/MS: (Method A) 464.0 (M+H), RT. 4.4 min, 95.4% (Max), 96.8% (254 nm). HPLC: (Method A) RT 4.4 min, 96.5% (Max), 96.6% (254 nm).

Example 10

3-Fluoro-8,15,17,25,29-pentaazahexacyclo[23.3.1.1$^{2,6}$1$^{19,23}$0$^{8,16}$0$^{9,14}$]hentriaconta-1(29),2(31),3,5,9(14),10,12,15,19(30),20,22,27-dodecaene-18,26-dione Step 1: Formation of Methyl 3-((3-(5-((2-amino-1H-benzo[d]imidazol-1-yl)methyl)-2-fluorophenyl)-6-oxopyridazin-1(6H)-yl)methyl)benzoate

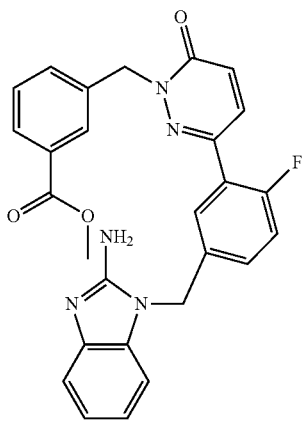 [SMILES: COC(=O)c1cccc(Cn2nc(-c3cc(Cn4c(N)nc5ccccc54)ccc3F)ccc2=O)c1]

A solution of methyl 3-((3-(5-(bromomethyl)-2-fluorophenyl)-6-oxopyridazin-1(6H)-yl)methyl)benzoate (2 g, 4.65 mmol), cesium carbonate (1.16 g, 3.6 mmol) and 3-amino-benzimidazole (475 mg, 3.6 mmol) in DMF (15 mL) was heated at 120° C. for 1 h. DMF was removed under reduced pressure and the reaction mixture was treated with water. The aqueous phase was extracted with ethyl acetate (3×15 mL), combined organic phases were dried over anhydrous Na$_2$SO$_4$, filtered and concentrated. Purification by flash chromatography on silica of the crude obtained afforded the title compound as an off-white solid (600 mg, 27%). LC/MS: (Method A) 484.0 (M+H), RT. 3.7 min.

Step 2: Formation of Lithium 3-{3-[5-(2-Amino-benzoimidazol-1-ylmethyl)-2-fluoro-phenyl]-6-oxo-6-pyridazin-1-ylmethyl}-benzoate

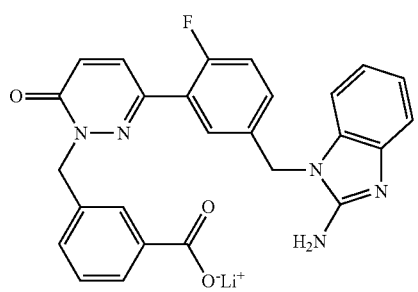

The title compound was obtained following procedure described for example 1, step 2 from Methyl 3-((3-(5-((2-amino-1H-benzo[d]imidazol-1-yl)methyl)-2-fluorophenyl)-6-oxopyridazin-1(6H)-yl)methyl)benzoate as an off-white solid (600 mg, quantitative). LC/MS: (Method A) 470.0 (M+H), RT. 3.2 min.

Step 3: Formation of 3-Fluoro-8,15,17,25,29-pentaazahexacyclo[23.3.1.1$^{2,6}$1$^{19,23}$0$^{8,16}$0$^{9,14}$]hentriaconta-1(29),2(31),3,5,9(14),10,12,15,19(30),20,22,27-dodecaene-18,26-dione

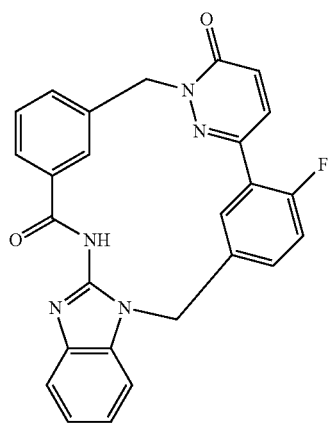 [SMILES: O=C1Nc2nc3ccccc3n2Cc2ccc(F)c(c2)-c2ccc(=O)n(n2)Cc2cccc1c2]

The title compound was obtained following procedure described for example 1, step 3 from Lithium 3-{3-[5-(2-Amino-benzoimidazol-1-ylmethyl)-2-fluoro-phenyl]-6-oxo-6-pyridazin-1-ylmethyl}-benzoate as an off-white solid (38 mg, 10%). $^1$H NMR (400 MHz, DMSO-d$_6$): δ 12.63 (s, 1H), 9.42 (d, J=7.1 Hz, 1H), 9.31 (s, 1H), 8.01 (d, J=7.7 Hz, 1H), 7.95 (d, J=7.9 Hz, 1H), 7.79-7.77 (m, 2H), 7.58 (d, J=7.6 Hz, 1H), 7.47-7.42 (m, 2H), 7.34-7.27 (m, 2H), 7.22-7.19 (m, 1H), 6.98 (d, J=9.7 Hz, 1H) 5.39 (s, 4H). LC/MS: (Method A) 452.2 (M+H), RT. 4.4 min, 97.5% (Max), 97.6% (254 nm). HPLC: (Method A) RT 4.4 min, 98.1% (Max), 97.9% (254 nm).

Example 11

3-methyl-6,14,16,23,32-pentaazahexacyclo [24.3.1.1$^{2,6}$.1$^{8,12}$.0$^{15,23}$.0$^{17,22}$]dotriaconta-1(30),2(32),3,8,10,12(31),15,17,19,21,26,28-dodecaene-5,13-dione Step 1: Formation of 3-(3-{3-[2-(2-Amino-benzoimidazol-1-yl)-ethyl]-phenyl}-4-methyl-6-oxo-6H-pyridazin-1-ylmethyl)-benzoic acid methyl ester

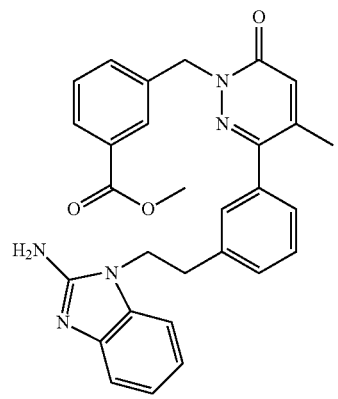 [SMILES: COC(=O)c1cccc(Cn2nc(-c3cccc(CCn4c(N)nc5ccccc54)c3)c(C)cc2=O)c1]

The title compound was obtained following procedure described for example 2, step 1 from 2-amino benzimidazole and 3-(4-Methyl-6-oxo-3-{3-[2-(toluene-4-sulfonyloxy)-ethyl]-phenyl}-6H-pyridazin-1-ylmethyl)-benzoic acid methyl ester as a brown gum (600 mg, 60%). LC/MS: (Method A) 494.0 (M+H), RT. 3.7 min, 68.0% (Max).

Step 2: Formation of Lithium 3-(3-{3-[2-(2-Amino-benzoimidazol-1-yl)-ethyl]-phenyl}-4-methyl-6-oxo-6H-pyridazin-1-ylmethyl)-benzoate

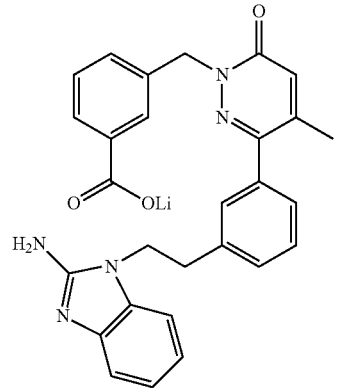

The title compound was obtained following procedure described for example 1, step 2 from 3-(3-{3-[2-(2-Amino-benzoimidazol-1-yl)-ethyl]-phenyl}-4-methyl-6-oxo-6H-pyridazin-1-ylmethyl)-benzoic acid methyl ester as a brown solid (300 mg, 50%). LC/MS: (Method A) 480.0 (M+H), RT. 3.3 min.

Step 3: Formation of 3-methyl-6,14,16,23,32-pentaazahexacyclo[24.3.1.1²,⁶.1⁸,¹².0⁵,²³.0¹⁷,²²]dotriaconta-1(30),2(32),3,8,10,12(31),15,17,19,21,26,28-dodecaene-5,13-dione

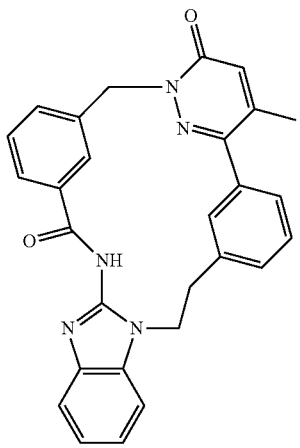 [SMILES: Cc1cc(=O)n2nc1-c1cccc(c1)CCn1c(nc3ccccc31)NC(=O)c1cccc(c1)C2]

The title compound was obtained following procedure described for example 1, step 3 from lithium 3-(3-{3-[2-(2-Amino-benzoimidazol-1-yl)-ethyl]-phenyl}-4-methyl-6-oxo-6H-pyridazin-1-ylmethyl)-benzoate as an off-white solid (51 mg, 21%). ¹H NMR (400 MHz, DMSO-d6): δ 12.83 (s, 1H), 9.00 (s, 1H), 8.07 (d, J=7.84 Hz, 1H), 7.88 (s, 1H), 7.72 (d, J=7.76 Hz, 1H), 7.62-7.55 (m, 3H), 7.48-7.41 (m, 3H), 7.33-7.23 (m, 2H), 6.86 (d, J=1.16 Hz, 1H), 5.33 (s, 2H), 4.61-4.57 (m, 2H), 3.03-2.99 (m, 2H), 2.21 (s, 3H). LC/MS: (Method C) 462.3 (M+H), RT. 9.3 min, 97.6% (Max), 95.9% (254 nm). HPLC: (Method C) RT 9.1 min, 97.5% (Max), 96.2% (254 nm).

Example 12

3-hydroxy-8,15,17,25,29-pentaazahexacyclo[23.3.1.1²,⁶.1¹⁹,²³.0⁸,²⁶.0⁹,¹⁴]hentriaconta-1(29),2(31),3,5,9(14),10,12,15,19(30),20,22,27-dodecaene-18,26-dione Step 1: Formation of 3-{3-[5-(2-Amino-benzoimidazol-1-ylmethyl)-2-methoxymethoxy-phenyl]-6-oxo-6H-pyridazin-1-ylmethyl}-benzoic acid methyl ester

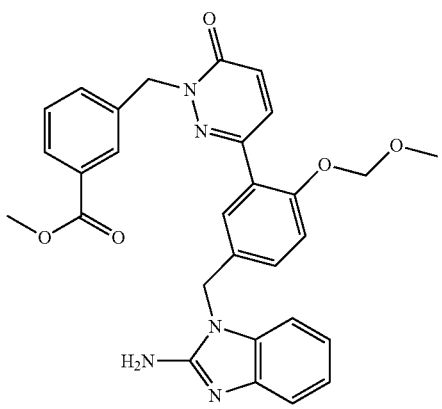

The title compound was obtained following procedure described for example 2, step 1 from 2-amino benzimidazole and 3-{3-[2-Methoxymethoxy-5-(toluene-4-sulfonyloxymethyl)-phenyl]-6-oxo-6H-pyridazin-1-ylmethyl}-benzoic acid methyl ester as a brown gum (500 mg, 27%). LC/MS: (Method A) 526.0 (M+H), RT. 3.68 min.

Step 2: Formation of Lithium 3-{3-[5-(2-Amino-benzoimidazol-1-ylmethyl)-2-methoxymethoxy-phenyl]-6-oxo-6H-pyridazin-1-ylmethyl}-benzoate

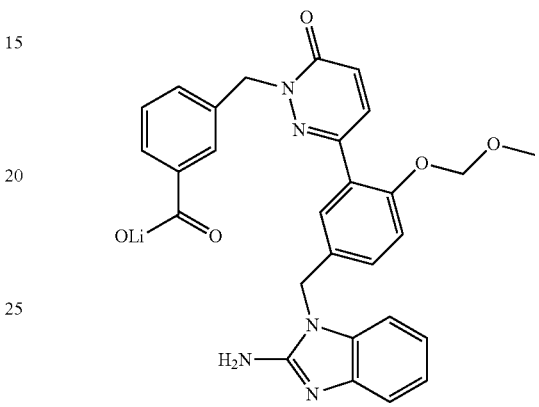

The title compound was obtained following procedure described for example 1, step 2 from 3-{3-[5-(2-Amino-benzoimidazol-1-ylmethyl)-2-methoxymethoxy-phenyl]-6-oxo-6H-pyridazin-1-ylmethyl}-benzoic acid methyl ester as a yellow solid (400 mg, 83%). LC/MS: (Method A) 512.0 (M+H), RT. 3.24 min.

Step 3: Formation of 3-(methoxymethoxy)-8,15,17,25,29-pentaazahexacyclo[23.3.1.1²,⁶.1¹⁹,²³.0⁸,¹⁶.0⁹,¹⁴]hentriaconta-1(29),2(31),3,5,9(14),10,12,15,19(30),20,22,27-dodecaene-18,26-dione

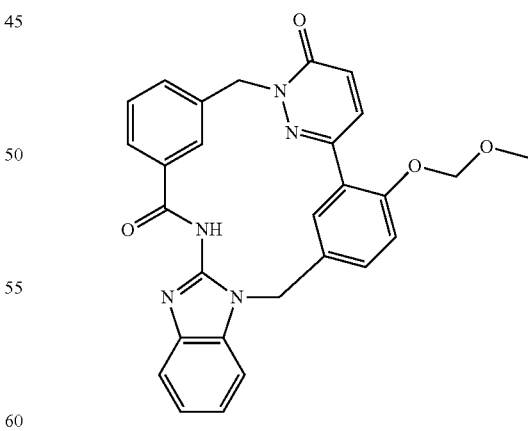

The title compound was obtained following procedure described for example 1, step 3 from lithium 3-{3-[5-(2-Amino-benzoimidazol-1-ylmethyl)-2-methoxymethoxy-phenyl]-6-oxo-6H-pyridazin-1-ylmethyl}benzoate as an off-white solid (50 mg, 13%). LC/MS: (Method A) 494.0 (M+H), RT. 4.23 min, 85.5% (Max).

Step 4: Formation of 3-hydroxy-8,15,17,25,29-pentaazahexacyclo[23.3.1.1^{2,6}.1^{19,23}.0^{8,16}.0^{9,14}]hentriaconta-1(29),2(31),3,5,9(14),10,12,15,19(30),20,22,27-dodecaene-18,26-dione

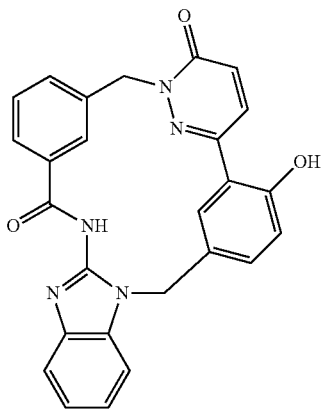 [SMILES: O=C1Nc2nc3ccccc3n2Cc2ccc(O)c(c2)-c2ccc(=O)n(n2)Cc2cccc1c2]

Concentrated sulphuric acid (5 mL) was added slowly to a solution of 3-(methoxymethoxy)-8,15,17,25,29-pentaazahexacyclo[23.3.1.12,6.119,23.08,16.09,14]hentriaconta-1(29),2(31),3,5,9(14),10,12,15,19(30),20,22,27-dodecaene-18,26-dione (50 mg) in THF (7 mL) maintained at 0° C. The reaction mixture was then allowed to warm to RT and stirred for 1 h. Water was added, dioxane was removed under reduced pressure and resulting phase was extracted with DCM (3×25 mL). Combined organic phaseswere dried over anhydrous Na$_2$SO$_4$, filtered and concentrated. Purification by flash chromatography on silica afforded the title compound as beige solid (6 mg, 8%). $^1$H NMR (400 MHz, DMSO-d$_6$): δ 12.59 (s, 1H), 10.39 (s, 1H), 9.32 (s, 1H), 9.23 (s, 1H), 8.06-7.99 (m, 2H), 7.87 (d, J=6.72 Hz, 1H), 7.56 (s, 2H), 7.43 (d, J=10.8 Hz, 2H), 7.24 (m, 2H), 6.89 (d, J=8.8 Hz, 2H), 5.94 (s, 4H). LC/MS: (Method A) 450.0 (M+H), RT. 3.65 min, 92.87% (Max), 93.11% (254 nm). HPLC: (Method A) RT. 3.65 min, 93.4% (Max), 94.5% (254 nm).

Example 13

3-chloro-8,15,17,25,29-pentaazahexacyclo[23.3.1.1^{2,6}.1^{19,23}.0^{8,16}.0^{9,14}]hentriaconta-1(29),2(31),3,5,9(14),10,12,15,19(30),20,22,27-dodecaene-18,26-dione Step 1: Formation of 3-{3-[5-(2-Amino-benzoimidazol-1-ylmethyl)-2-chloro-phenyl]-6-oxo-6H-pyridazin-1-ylmethyl}-benzoic acid methyl ester

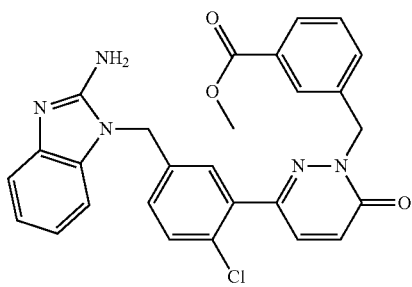 [SMILES: COC(=O)c1cccc(Cn2nc(-c3cc(Cn4c(N)nc5ccccc54)ccc3Cl)ccc2=O)c1]

The title compound was obtained following procedure described for example 2, step 1 from 3-{3-[2-Chloro-5-(toluene-4-sulfonyloxymethyl)-phenyl]-6-oxo-6H-pyridazin-1-ylmethyl}-benzoic acid methyl ester as a brown gum (1.3 g, 56%). LC/MS: (Method A) 500.0 (M+H), RT. 3.8 min, 22.0% (Max).

Step 2: Formation of Lithium 3-{3-[5-(2-Amino-benzoimidazol-1-ylmethyl)-2-chloro-phenyl]-6-oxo-6H-pyridazin-1-ylmethyl}-benzoate

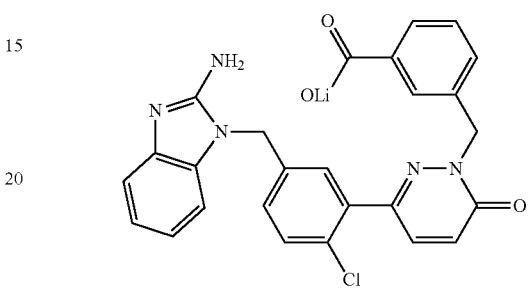

The title compound was obtained following procedure described for example 1, step 2 from 3-{3-[5-(2-Amino-benzoimidazol-1-ylmethyl)-2-chloro-phenyl]-6-oxo-6H-pyridazin-1-ylmethyl}-benzoic acid methyl ester as a beige solid (1.0 g, 79%). LC/MS: (Method A) 486.0 (M+H), RT. 3.8 min.

Step 3: Formation of 3-chloro-8,15,17,25,29-pentaazahexacyclo[23.3.1.1^{2,6}.1^{19,23}.0^{8,16}.0^{9,14}]hentriaconta-1(29),2(31),3,5,9(14),10,12,15,19(30),20,22,27-dodecaene-18,26-dione

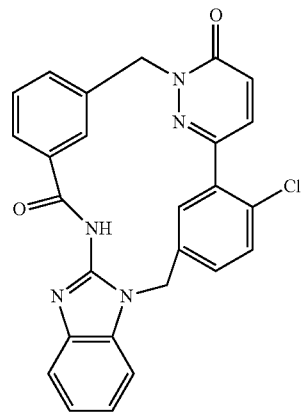 [SMILES: O=C1Nc2nc3ccccc3n2Cc2ccc(Cl)c(c2)-c2ccc(=O)n(n2)Cc2cccc1c2]

The title compound was obtained following procedure described for example 1, step 3 from Lithium 3-{3-[5-(2-Amino-benzoimidazol-1-ylmethyl)-2-chloro-phenyl]-6-oxo-6H-pyridazin-1-ylmethyl}-benzoate as an off-white solid (38 mg, 24%). $^1$H NMR (400 MHz, DMSO-d6): δ 12.55 (s, 1H), 9.27 (d, J=2.08 Hz, 1H), 9.15 (s, 1H), 7.99 (d, J=7.84 Hz, 1H), 7.91-7.83 (m, 3H), 7.59 (d, J=8.12 Hz, 2H), 7.48-7.42 (m, 2H), 7.28-7.17 (m, 2H), 6.95 (d, J=9.68 Hz, 1H), 5.60-5.21 (m, 4H). LC/MS: (Method A) 468.0 (M+H), RT. 4.4 min, 96.8% (Max), 97.6% (254 nm). HPLC: (Method A) RT 4.31 min, 92.6% (Max), 94.5% (254 nm).

Example 14

4,5,8,15,17,25,29-heptaazahexacyclo[23.3.1.1$^{2,5}$.1$^{19,23}$.0$^{8,16}$.0$^{9,14}$]hentriaconta-1(29),2(31),3,9(14),10,12,15,19(30),20,22,27-undecaene-18,26-dione Step 1: Formation of 3-(3-{1-[2-(2-Amino-benzoimidazol-1-yl)-ethyl]-1H-pyrazol-4-yl}-6-oxo-6H-pyridazin-1-ylmethyl)-benzoic acid methyl ester

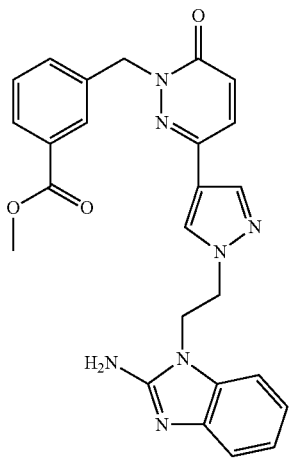 [SMILES: COC(=O)c1cccc(Cn2nc(-c3cnn(CCn4c(N)nc5ccccc54)c3)ccc2=O)c1]

The title compound was obtained following procedure described for example 2, step 1 from 3-(6-Oxo-3-{1-[2-(toluene-4-sulfonyloxy)-ethyl]-1H-pyrazol-4-yl}-6H-pyridazin-1-ylmethyl)-benzoic acid methyl ester as a brown solid (0.95 g, 37%). LC/MS: (Method A) 470.2 (M+H), RT. 3.17 min.

Step 2 Formation of Lithium 3-(3-{1-[2-(2-Amino-benzoimidazol-1-yl)-ethyl]H-pyrazol-4-yl}-6-oxo-6H-pyridazin-1-ylmethyl)benzoate

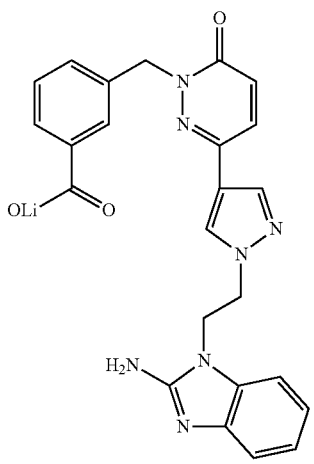

The title compound was obtained following procedure described for example 1, step 2 from 3-(3-{1-[2-(2-Amino-benzoimidazol-1-yl)-ethyl]-1H-pyrazol-4-yl}-6-oxo-6H-pyridazin-1-ylmethyl)-benzoic acid methyl ester as a brown solid (0.4 g, 83%). LC/MS: (Method A) 456.2 (M+H), RT. 2.75 min.

Step 3: Formation of 4,5,8,15,17,25,29-heptaazahexacyclo[23.3.1.1$^{2,5}$.1$^{19,23}$.0$^{8,16}$.0$^{9,14}$]hentriaconta-1(29),2(31),3,9(14),10,12,15,19(30),20,22,27-undecaene-18,26-dione

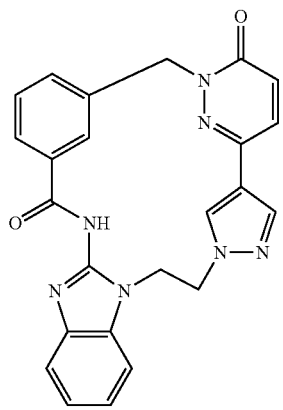 [SMILES: O=C1Nc2nc3ccccc3n2CCn2cc(cn2)-c2ccc(=O)n(n2)Cc2cccc1c2]

The title compound was obtained following procedure described for example 1, step 3 from of lithium 3-(3-{1-[2-(2-Amino-benzoimidazol-1-yl)-ethyl]-1H-pyrazol-4-yl}-6-oxo-6H-pyridazin-1-ylmethyl)benzoate as off white solid. (7.8 mg, 8%). $^1$H NMR (400 MHz, DMSO-d$_6$): δ 12.75 (s, 1H), 9.28 (s, 1H), 9.00 (s, 1H), 8.00 (d, J=7.76 Hz, 1H), 7.84 (s, 1H), 7.71 (d, J=9.20 Hz, 2H), 7.51 (dd, J=10.72, 7.28 Hz, 2H), 7.41 (t, J=7.60 Hz, 1H), 7.31-7.23 (m, 2H), 6.91 (d, J=9.52 Hz, 1H), 5.33 (s, 2H), 4.97 (s, 2H), 4.71 (s, 2H). LC/MS: (Method A) 438.0 (M+H), RT. 3.22 min, 95.83% (Max), 95.99% (254 nm). HPLC: (Method A) RT. 3.29 min, 96.2% (Max), 95.7% (254 nm).

Example 15

3-methoxy-8,15,17,25,29-pentaazahexacyclo[23.3.1.1$^{2,6}$.1$^{19,23}$.0$^{8,16}$.0$^{9,14}$]hentriaconta-1(29),2(31),3,5,9(14),10,12,15,19(30),20,22,27-dodecaene-18,26-dione Step 1: Formation of 3-{3-[5-(2-Amino-benzoimidazol-1-ylmethyl)-2-methoxy-phenyl]-6-oxo-6H-pyridazin-1-ylmethyl}-benzoic acid methyl ester

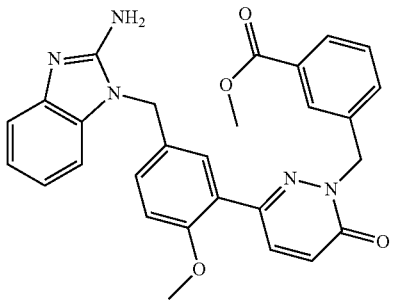 [SMILES: COC(=O)c1cccc(Cn2nc(-c3cc(Cn4c(N)nc5ccccc54)ccc3OC)ccc2=O)c1]

The title compound was obtained following procedure described for example 10, step 1 from 3-[3-(5-Bromomethyl-2-methoxy-phenyl)-6-oxo-6H-pyridazin-1-ylmethyl]-benzoic acid methyl ester as a brown solid (1.0 g, 59%). LC/MS: (Method A) 496.2 (M+H), RT. 3.7 min.

Step 2: Formation of Lithium 3-{3-[5-(2-Amino-benzoimidazol-1-ylmethyl)-2-methoxy-phenyl]-6-oxo-6H-pyridazin-1-ylmethyl}-benzoate

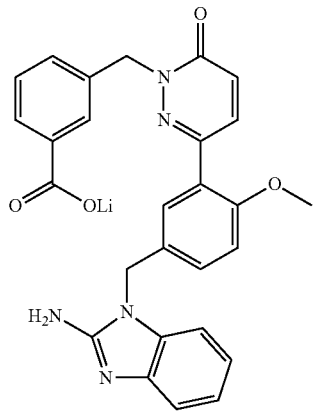

The title compound was obtained following procedure described for example 1, step 2 from 3-{3-[5-(2-Amino-benzoimidazol-1-ylmethyl)-2-methoxy-phenyl]-6-oxo-6H-pyridazin-1-ylmethyl}-benzoic acid methyl ester as an off-white solid (400 mg, 40%). LC/MS: (Method A) 482.0 (M+H), RT. 3.2 min.

Step 3: Formation of 3-methoxy-8,15,17,25,29-pentaazahexacyclo[23.3.1.1$^{2,6}$.1$^{19,23}$.0$^{8,16}$.0$^{9,14}$]hentriaconta-1(29),2(31),3,5,9(14),10,12,15,19(30),20,22,27-dodecaene-18,26-dione

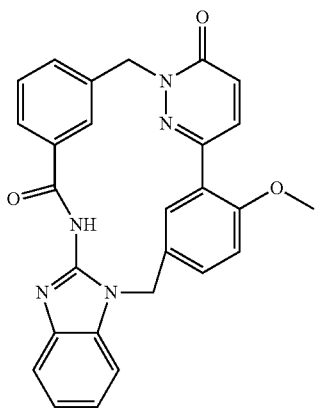 [SMILES: COc1ccc2cc1-c1ccc(=O)n(n1)Cc1cccc(c1)C(=O)Nc1nc3ccccc3n1C2]

The title compound was obtained following procedure described for example 1, step 3 from lithium 3-{3-[5-(2-Amino-benzoimidazol-1-ylmethyl)-2-methoxy-phenyl]-6-oxo-6H-pyridazin-1-ylmethyl}-benzoate as an off-white solid (37 mg, 23%). $^1$H NMR (400 MHz, DMSO-d6): δ 12.57 (s, 1H), 9.28 (d, J=7.08 Hz, 2H), 8.00 (d, J=7.76 Hz, 1H), 7.91-7.88 (m, 2H), 7.78 (d, J=8.44 Hz, 1H), 7.58 (d, J=7.24 Hz, 1H), 7.46-7.42 (m, 2H), 7.29-7.26 (m, 1H), 7.21-7.17 (m, 1H), 7.11 (d, J=8.48 Hz, 1H), 6.89 (d, J=9.72 Hz, 1H), 5.70-5.10 (m, 4H), 3.86 (s, 3H). LC/MS: (Method A) 464.0 (M+H), RT. 4.1 min, 98.8% (Max), 99.2% (254 nm). HPLC: (Method A) RT 4.2 min, 97.1% (Max), 97.3% (254 nm).

Example 18

20-hydroxy-23-oxa-1,9,11,18,28-pentaazapentacyclo[22.3.1.1$^{3,7}$.0$^{10,18}$.0$^{12,17}$]nonacosa-3,5,7(29),10,12(17),13,15,24(28),25-nonaene-8,27-dione Step 1: Formation of Potassium 3-{3-[4-(2-Amino-benzoimidazol-1-yl)-3-hydroxy-butoxy]-6-oxo-6H-pyridazin-1-ylmethyl}-benzoic acetate

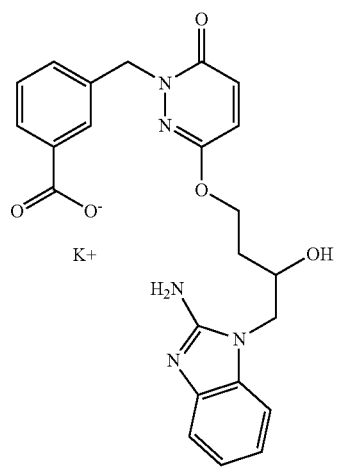 [SMILES: Nc1nc2ccccc2n1CC(O)CCOc1ccc(=O)n(Cc2cccc(C(=O)[O-])c2)n1 ; [K+]]

Potassium hydroxide pellets were added to a stirred solution of 3-[3-(2-Oxiranyl-ethoxy)-6-oxo-6H-pyridazin-1-ylmethyl]-benzoic acid methyl ester (0.45 g, 1.36 mmol) and 2-aminobenzimidazole (0.18 g, 1.36 mmol) in methanol/water (7:3, 10 mL). The reaction mixture was heated in MW at 100° C. for 1 h and concentrated under reduced pressure. Residual water was removed by co-distillation with toluene from resulting solid. The title compound was obtained as beige solid (600 mg, 98%). LC/MS: (Method A) 450.0 (M+H).

Step 2: Formation of 20-hydroxy-23-oxa-1,9,11,18, 28-pentaazapentacyclo[22.3.1.1$^{3,7}$.0$^{10,18}$.0$^{12,17}$]nona-cosa-3,5,7(29),10,12(17),13,15,24(28),25-nonaene-8,27-dione

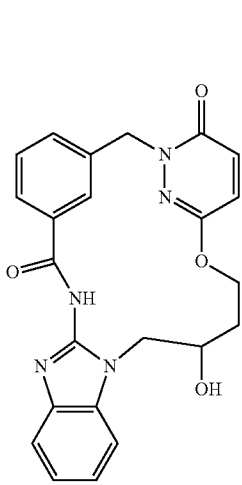 [SMILES: O=C1Nc2nc3ccccc3n2CC(O)CCOc2ccc(=O)n(n2)Cc2cccc1c2]

A solution of potassium 3-{3-[4-(2-Amino-benzoimidazol-1-yl)-3-hydroxy-butoxy]-6-oxo-6H-pyridazin-1-ylmethyl}-benzoic acetate (200 mg, 0.44 mmol) in DMF (20 mL) was added slowly to a solution of HATU (0.51 g, 1.33 mmol), 1-Hydroxy-7-azabenzotriazole (0.18 g, 1.33 mmol), 4-dimethylaminopyridine (0.05 g, 0.44 mmol) and N,N-diisopropylethylamine (0.6 mL, 3.5 mmol) in dry DMF (160 mL). The reaction mixture was stirred at RT for 14 h, concentrated under reduced pressure and extracted with dichloromethane. Combined organic layers were washed with aqueous citric acid solution (10% w/v), followed by NaHCO$_3$, water and brine, concentrated, filtered and concentrated. Purification by flash column chromatography on silica afforded the title compound as pale yellow solid (13 mg, 7%) $^1$H NMR (400 MHz, DMSO-d6): δ 12.71 (s, 1H), 8.70 (s, 1H), 7.94 (d, J=7.72 Hz, 1H), 7.55 (d, J=7.44 Hz, 1H), 7.52-7.48 (m, 2H), 7.41 (t, J=7.52 Hz, 1H), 7.24-7.16 (m, 3H), 6.92 (d, J=9.76 Hz, 1H), 5.31 (d, J=13.96 Hz, 1H), 5.25 (d, J=4.92 Hz, 1H), 4.97 (d, J=13.92 Hz, 1H), 4.70-4.64 (m, 1H), 4.43-4.33 (m, 2H), 3.99-3.95 (m, 2H), 2.32-2.27 (m, 1H), 1.96-1.92 (m, 1H). LC/MS: (Method A) 432.0 (M+H), RT. 2.9 min, 94.7% (Max), 94.8% (254 nm). HPLC: (Method A) RT 3.1 min, 96.8% (Max), 96.5% (254 nm).

Example 19

5-methoxy-8,15,17,25,29-pentaazahexacyclo [23.3.1.1$^{2,6}$.1$^{19,23}$.0$^{8,16}$.0$^{9,14}$]hentriaconta-1(29),2 (31),3,5,9(14),10,12,15,19(30),20,22,27-dodecaene-18,26-dione Step 1: Formation of 3-{3-[3-(2-Amino-benzoimidazol-1-ylmethyl)-4-methoxy-phenyl]-6-oxo-6H-pyridazin-1-ylmethyl}-benzoic acid methyl ester

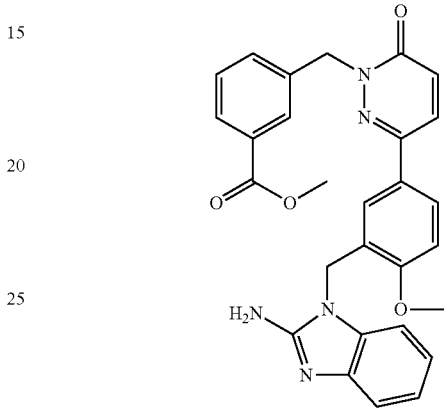

The title compound was obtained following procedure described for example 1, step 1 as a brown solid (1 g, 76%). $^1$H NMR (400 MHz, DMSO-d$_6$): δ 7.92-7.92 (m, 1H), 7.88-7.81 (m, 2H), 7.76 (dd, J=8.6, 2.2 Hz, 1H), 7.53 (t, J=7.7 Hz, 1H), 7.44-7.40 (m, 1H), 7.32-7.31 (m, 1H), 7.18-7.13 (m, 2H), 7.02-6.80 (m, 3H), 6.79 (t, J=6.6 Hz, 1H), 6.58 (br s, 2H), 5.22 (s, 2H), 5.19 (s, 2H), 3.91 (s, 3H), 3.83 (s, 3H). LC/MS: (Method A) 496.0 (M+H), RT. 3.7 min.

Step 2: Formation of Lithium 3-{3-[3-(2-Amino-benzoimidazol-1-ylmethyl)-4-methoxy-phenyl]-6-oxo-6H-pyridazin-1-ylmethyl}-benzoate

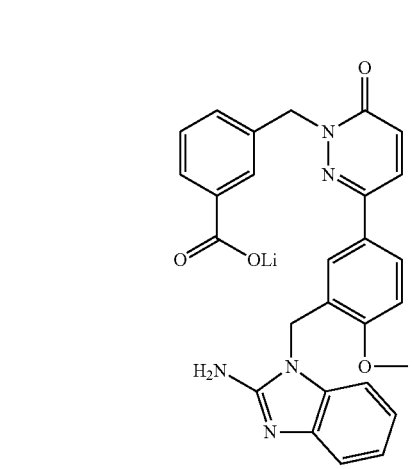

The title compound was obtained following procedure described for example 2, step 2 as a pale brown solid (800 mg). $^1$H NMR (400 MHz, DMSO-d$_6$): δ 8.51 (s, 1H), 7.91 (s, 1H), 7.84 (d, J=9.8 Hz, 1H), 7.78-7.72 (m, 2H), 7.47-7.47

(m, 1H), 7.25-7.17 (m, 2H), 7.12 (d, J=8.7 Hz, 1H), 7.00-6.96 (m, 2H), 6.93-6.89 (m, 1H), 6.85-6.80 (m, 1H), 6.75 (brs, 2H), 5.23 (s, 2H), 5.11 (s, 2H), 3.91 (s, 3H). LC/MS: (Method A) 482.0 (M+H).

Step 3: Formation of 5-methoxy-8,15,17,25,29-pentaazahexacyclo[23.3.1.1$^{2,6}$.1$^{19,23}$.0$^{8,16}$.0$^{9,14}$]hentriaconta-1(29),2(31),3,5,9(14),10,12,15,19(30),20,22,27-dodecaene-18,26-dione

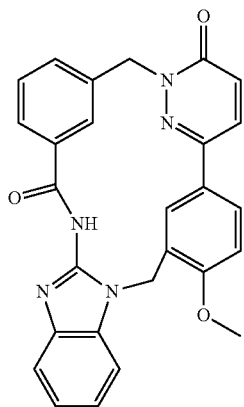 [SMILES: COc1ccc2cc1Cn1c(nc3ccccc31)NC(=O)c1cccc(c1)Cn1nc-2ccc1=O]

The title compound was obtained following procedure described for example 1, step 3 as an off-white solid (200 mg, 28%). 1HNMR (400 MHz, DMSO-d6): 12.75 (s, 1H), 9.38 (m, 2H), 8.00 (m, 2H), 7.82 (dd, J=6.24, 2.36 Hz, 1H), 7.77 (d, J=8.04 Hz, 1H), 7.54 (d, J=7.68 Hz, 1H), 7.49 (d, J=7.68 Hz, 1H), 7.40 (t, J=7.56 Hz, 1H), 7.32 (t, J=8.20 Hz, 1H), 7.20 (t, J=7.52 Hz, 1H), 6.99 (d, J=8.48 Hz, 1H), 6.95 (d, J=9.56 Hz, 1H), 5.87 (m, 1H), 5.38 (m, 2H), 4.87 (m, 1H), 3.83 (s, 3H). HPLC (max plot) 96.87%; (254 nm) 96.29%; Rt (min) 4.48; MS: (ESI+) 464.2.

Example 20

5-hydroxy-8,15,17,25,29-pentaazahexacyclo[23.3.1.1$^{2,6}$.1$^{19,23}$.0$^{8,16}$.0$^{9,14}$]hentriaconta-1(29),2(31),3,5,9(14),10,12,15,19(30),20,22,27-dodecaene-18,26-dione

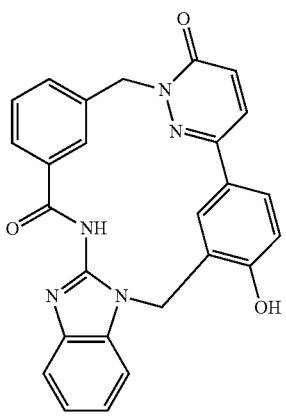 [SMILES: O=C1Nc2nc3ccccc3n2Cc2cc(ccc2O)-c2ccc(=O)n(n2)Cc2cccc1c2]

To a stirred solution of 5-methoxy-8,15,17,25,29-pentaazahexacyclo[23.3.1.1$^{2,6}$.1$^{19,23}$.0$^{8,16}$.0$^{9,14}$]hentriaconta-1(29),2(31),3,5,9(14),10,12,15,19(30),20,22,27-dodecaene-18,26-dione (0.1 g, 0.21 mmol) in dry dichloromethane (30 mL) was added, Borontribromide (0.64 mL, 0.64 mmol) at 0° C. The reaction mixture was stirred at room temperature for 48 h. It was then quenched with saturated ammonium chloride solution. The solid obtained was filtered off and purified by flash chromatography on silica to afford the title compound as a white solid (20 mg, 22%). $^1$H NMR (400 MHz, DMSO-d$_6$): δ 12.74 (s, 1H), 10.42 (s, 1H), 9.42-9.38 (m, 2H), 8.01-7.86 (m, 3H), 7.65-7.20 (m, 6H), 6.94-6.83 (m, 2H), 6.01-5.93 (m, 1H), 5.48-5.31 (m, 2H), 5.01-4.96 (m, 1H). LC/MS: (Method A) 450.2 (M+H), RT. 3.8 min, 93.3% (Max), 93.3% (254 nm). HPLC: (Method A) RT. 3.7 min, 94.1% (Max), 93.0% (254 nm).

Example 32a and 32b

Cis and trans 25-hydroxy-1,6,14,16,23,32-hexaazahexacyclo[24.3.1.1$^{2,6}$.1$^{8,12}$.0$^{15,23}$.0$^{17,22}$]dotriaconta-2(32),3,8(31),9,11,15,17(22),18,20-nonaene-5,13-dione Step 1: Formation of Potassium 3-(3-{3-[2-(2-Amino-benzoimidazol-1-yl)-1-hydroxy-ethyl]-piperidin-1-yl}-6-oxo-6H-pyridazin-1-ylmethyl)-benzate

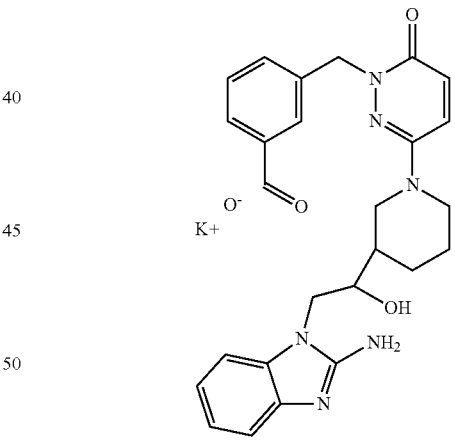

The title compound was obtained following procedure described for example 18, step 1 from 3-[3-(3-Oxiranyl-piperidin-1-yl)-6-oxo-6H-pyridazin-1-ylmethyl]-benzoic acid methyl ester (2.00 g; 1.95 mmol; 1.00 eq.) and 1H-Benzoimidazol-2-ylamine (259 mg; 1.95 mmol; 1.00 eq.) as a brown solid. (1.2 g, 78%). LC/MS: (Method A) 489.2 (M+H), RT. 2.8+3.0 min, 25.9+37.4% (Max), 29.0+41.0% (254 nm).

Step 2: Formation of Cis and trans Cis and trans 25-hydroxy-1,6,14,16,23,32-hexaazahexacyclo [24.3.1.1$^{2,6}$.1$^{8,12}$.0$^{15,23}$.0$^{17,22}$]dotriaconta-2(32),3,8(31),9,11,15,17(22),18,20-nonaene-5,13-dione

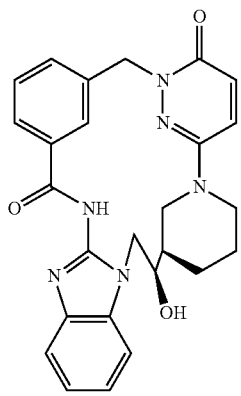

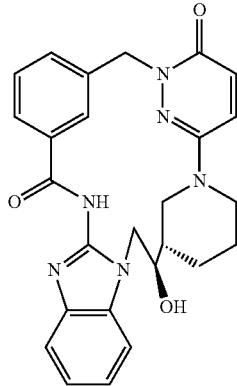

A solution of Potassium 3-(3-{3-[2-(2-Amino-benzoimidazol-1-yl)-1-hydroxy-ethyl]-piperidin-1-yl}-6-oxo-6H-pyridazin-1-ylmethyl)-benzate MF (60 mL) was added drop wise over a period of 5 h to a stirred solution of 1-Hydroxy-7-azabenzotriazole (1.06 g; 7.61 mmol; 5.00 eq.), HATU (2.90 g; 7.61 mmol; 5.00 eq.), N,N-diisopropylethylamine (2.69 mL; 15.2 mmol; 10.00 eq.) and DMAP (0.19 g; 1.52 mmol; 1.00 eq.), in DMF (1140 mL). The reaction mixture was then stirred for 16 h at RT and concentrated under reduced pressure. The solid residue was washed with water (3×50 mL) and filtered off. Purification by flash chromatography on silica (MeOH:DCM, gradient from 2 to 4%) afforded the title compound as an off white solid. (180 mg, 16%, mixture of cis and trans isomers). LC/MS: (Method A) 471.0 (M+H), RT. 3.2+3.4 min, 27.0+38.0% (Max), 31.0+40.0% (254 nm). The two isomers were then separated by prep HPLC (Method: Kromosil c18 (19×250)mm, 10 micron Mobile phase: 0.1% TFA in water B: Methanol Flow: 12 mL/min):

First eluting isomer: brown gum, (8 mg, 6%)$^1$H NMR (400 MHz, DMSO-d$_6$): δ 12.69 (s, 1H), 8.85 (brs, 1H), 7.92 (d, J=7.6 Hz, 1H), 7.51-7.46 (m, 2H), 7.45-7.43 (m, 2H), 7.38 (t, J=7.6 Hz, 1H), 7.26-7.19 (m, 2H), 6.71 (d, J=10.0 Hz, 1H), 5.52-5.30 (m, 1H), 5.27 (d, J=4.9 Hz, 1H), 4.74-4.48 (m, 2H), 4.38 (s, 1H), 4.11 (t, J=5.2 Hz, 1H), 3.88-3.83 (m, 1H), 3.63 (s, 1H), 3.06 (s, 1H), 2.77 (s, 1H), 1.79-1.72 (m, 1H), 1.70-1.52 (m, 3H), 1.50-1.38 (m, 1H). LC/MS: (Method A) 471.0 (M+H), RT. 4.8 min, 93.3% (Max), 93.5% (254 nm). HPLC: (Method A) RT. 4.7 min, 92.7% (Max), 93.9% (254 nm). Second eluting isomer: white solid, (16 mg, 12%). $^1$H NMR (400 MHz, DMSO-d$_6$): δ 12.70 (s, 1H), 7.93 (d, J=7.6 Hz, 1H), 7.60 (d, J=7.4 Hz, 1H), 7.52-7.46 (m, 3H), 7.39 (t, J=7.5 Hz, 1H), 7.24-7.16 (m, 2H), 6.79 (d, J=10.0 Hz, 1H), 5.49-5.21 (m, 1H), 5.15-5.01 (m, 1H), 4.72-4.68 (m, 1H), 4.64-4.21 (m, 1H), 4.03 (d, J=10.3 Hz, 1H), 3.95-3.89 (m, 1H), 3.61-3.57 (m, 1H), 3.54-3.44 (m, 1H), 2.97-2.89 (m, 2H), 1.81-1.81 (m, 2H), 1.77-1.72 (m, 2H), 1.60-1.42 (m, 1H), 1.41-1.25 (m, 1H). LC/MS: (Method A) 471.0 (M+H), RT. 4.8 min, 91.8% (Max), 91.8% (254 nm). HPLC: (Method A) RT. 4.7 min, 91.0% (Max), 91.8% (254 nm).

Example 36a and 36b

R and S 24-ethyl-8,15,17,25,29-pentaazahexacyclo [23.3.1.1$^{2,6}$.1$^{19,23}$.0$^{8,16}$.0$^{9,14}$]hentriaconta-1(29),2(31),3,5,9(14),10,12,15,19,21,23(30),27-dodecaene-18,26-dione Step 1: Formation of 3-(1-{3-[3-(2-Amino-benzoimidazol-1-ylmethyl)-phenyl]-6-oxo-6H—

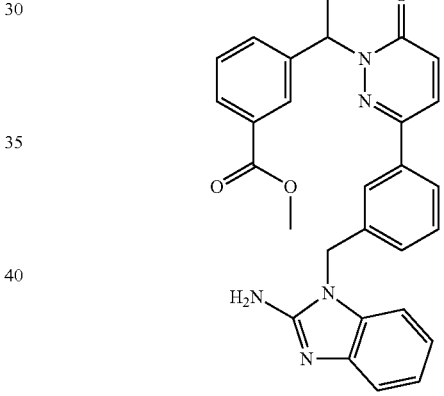

A solution of 3-{1-[3-(3-Bromomethyl-phenyl)-6-oxo-6H-pyridazin-1-yl]-propyl}-benzoic acid methyl ester (1.90 g; 4.1761 mmol; 1.00 eq.), Cesium carbonate (4.12 g; 12.5284 mmol; 3.00 eq.) and 1H-Benzoimidazol-2-ylamine (0.56 g; 4.1761 mmol; 1.00 eq.) in DMF (13.3 mL) was heated in MW at 120° C. for 1 h. Reaction mass was evaporated to dryness and the residue was dissolved in ethyl acetate (100 mL), washed with water (2×50 mL), dried over anhydrous Na$_2$SO$_4$, filtered and concentrated. Purification by flash chromatography on silica (MeOH:DCM, 5:95) afforded the title compound as an off white foam. (600 mg, 27%). 1H NMR (400 MHz, DMSO-d6): δ 8.15-7.92 (m, 2H), 7.85 (t, J=1.4 Hz, 1H), 7.77 (d, J=2.0 Hz, 2H), 7.58-7.50 (m, 2H), 7.46 (t, J=7.8 Hz, 1H), 7.30 (d, J=7.8 Hz, 1H), 7.15 (t, J=7.7 Hz, 2H), 7.03 (d, J=9.7 Hz, 1H), 6.94-6.90 (m, 1H), 6.85-6.81 (m, 1H), 6.63 (s, 2H), 6.02 (t, J=6.68 Hz, 1H), 5.36 (s, 2H), 3.83 (s, 3H), 2.22-2.15 (m, 1H), 2.06-1.98 (m, 1H), 0.8 (t, J=7.2 Hz, 3H). LC/MS: (Method A) 494.2 (M+H), RT. 4.0 min, 94.2% (Max), 94.5% (254 nm).

Step 2: Formation of lithium 3-(1-{3-[3-(2-Amino-benzoimidazol-1-ylmethyl)-phenyl]-6-oxo-6H-pyridazin-1-yl}-propyl)-benzoate

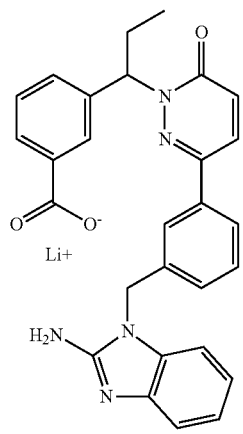 [SMILES: CCC(c1cccc(C(=O)[O-])c1)n1nc(-c2cccc(Cn3c(N)nc4ccccc43)c2)ccc1=O ; [Li+]]

The title compound was obtained following procedure described for example 3, step 2 from 3-(1-{3-[3-(2-Amino-benzoimidazol-1-ylmethyl)-phenyl]-6-oxo-6H-pyridazin-1-yl}-propyl)-benzoic acid methyl ester (600 mg; 1.15 mmol; 1.00 eq.) as a white solid (500 mg, 84%). 1H NMR (400 MHz, DMSO-d6): δ 8.14 (s, 1H), 7.99-7.93 (m, 2H), 7.77-7.73 (m, 2H), 7.73-7.39 (m, 1H), 7.31-7.26 (m, 2H), 7.24-7.19 (m, 2H), 7.12 (d, J=7.2 Hz, 1H), 6.99 (d, J=9.7 Hz, 1H), 6.91-6.88 (m, 1H), 6.83-6.81 (m, 1H), 5.98 (t, J=8.56 Hz, 1H), 5.45-5.32 (m, 2H), 2.26-2.19 (m, 1H), 2.09-2.02 (m, 1H), 0.77 (t, J=7.20 Hz, 3H). LC/MS: (Method A) 480.2 (M+H), RT. 3.5 min, 93.7% (Max), 92.6% (254 nm).

Step 3: Formation of 24-ethyl-8,15,17,25,29-pentaazahexacyclo[23.3.1.1$^{2,6}$.1$^{19,23}$.0$^{8,16}$.0$^{9,14}$]hentriaconta-1(29),2(31),3,5,9(14),10,12,15,19,21,23(30),27-dodecaene-18,26-dione

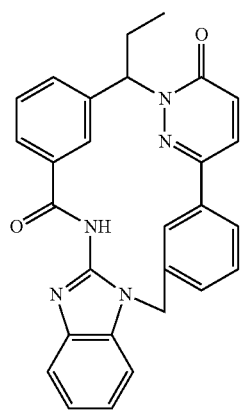 [SMILES: CCC1c2cccc(c2)C(=O)Nc2nc3ccccc3n2Cc2cccc(c2)-c2ccc(=O)n1n2]

The title compound was obtained following procedure described for example 32, step 2 from lithium 3-(1-{3-[3-(2-Amino-benzoimidazol-1-ylmethyl)-phenyl]-6-oxo-6H-pyridazin-1-yl}-propyl)-benzoate (0.50 g; 0.97 mmol; 1.00 eq.) as an off-white solid (150 mg; 33%). off-white solid. 1H NMR: (400 MHz, DMSO-d6): δ 12.66 (s, 1H), 9.45 (d, J=13.6 Hz, 2H), 8.07-7.99 (m, 3H), 7.83 (d, J=8.4 Hz, 1H), 7.62 (d, J=8.0 Hz, 1H), 7.54 (d, J=7.6 Hz, 1H), 7.48 (d, J=7.6 Hz, 1H), 7.44-7.38 (m, 2H), 7.33-7.29 (m, 1H), 7.21 (t, J=8.3 Hz, 1H), 6.99 (d, J=9.68 Hz, 1H), 6.17 (t, J=6.96 Hz, 1H), 5.50-5.38 (m, 2H), 2.39-2.31 (m, 1H), 2.23-2.16 (m, 1H), 0.9 (t, J=7.2 Hz, 3H). LC/MS: (Method A) 462.3 (M+H), RT. 4.6 min, 95.6% (Max), 97.7% (254 nm). HPLC: (Method A) RT 4.5 min, 98.5% (Max), 98.2% (254 nm).

Step 4: Chiral separation of 24-ethyl-8,15,17,25,29-pentaazahexacyclo[23.3.1.1$^{2,6}$.1$^{19,23}$.0$^{8,16}$.0$^{9,14}$]hentriaconta-1(29),2(31),3,5,9(14),10,12,15,19,21,23(30),27-dodecaene-18,26-dione

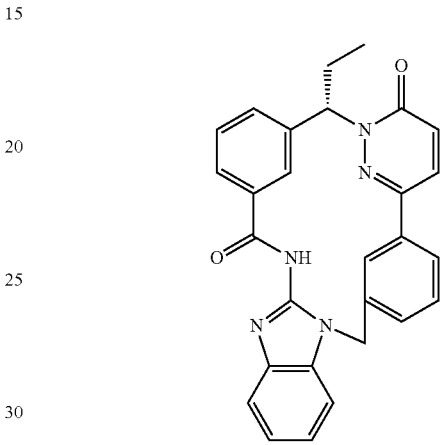

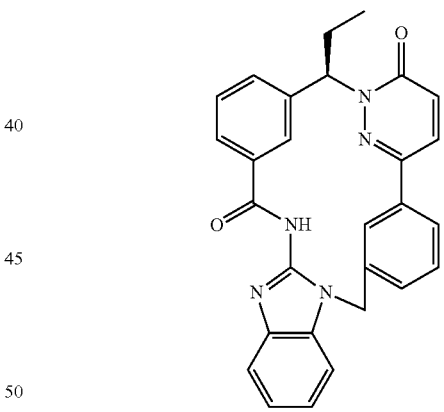

The two enantiomers of were separated by Chiral prep. HPLC (Method: Mobile Phase: 0.1% DEA in hexane:ethanol: 60:40; column Chiralpak IC (250×4.6)mm, 5 μm. FLOW: 1 mL\min):

First eluting enantiomer: off white solid (8 mg, 16%). LC/MS: (Method A) 462.0 (M+H), RT. 4.6 min, 99.8% (Max), 99.7% (254 nm). HPLC: (Method A) RT 4.5 min, 99.4% (Max), 99.6% (254 nm).

Second eluting enantiomer: off white solid (8 mg, 16%). LC/MS: (Method A) 462.0 (M+H), RT. 4.6 min, 99.4% (Max), 99.6% (254 nm). HPLC: (Method A) RT 4.5 min, 99.2% (Max), 99.8% (254 nm).

Examples described in table 1 are prepared following similar protocols.

TABLE 1 analytical description

| Example compound | Description |
|---|---|
| 16 | Off white solid: 1HNMR (400 MHz, DMSO-d6): 12.66 (s, 1H), 9.35, 9.27 (s, 1H), 8.60 (d, J = 5.12 Hz, 1H), 8.13 (d, J = 9.76 Hz, 1H), 8.01 (d, J = 7.76 Hz, 1H), 7.82 (m, 2H), 7.57 (d, J = 7.64 Hz, 1H), 7.48 (d, J = 7.60 Hz, 1H), 7.41 (t, J = 7.76 Hz, 1H), 7.31 (t, J = 7.48 Hz, 1H), 7.21 (t, J = 7.32 Hz, 1H), 7.07 (d, J = 9.68 Hz, 1H), 5.47 (m, 4H). HPLC (max plot) 95.09%; (254 nm) 94.5%; Rt (min) 3.1; MS: (ESI+) 435.2. |
| 17 | Off white solid: 1HNMR (400 MHz, DMSO-d6): 12.84 (s, 1H), 9.02 (s, 1H), 1.03 (s, 1H), 8.03 (d, J = 7.5 Hz, 1H), 7.95 (d, J = 9.6 Hz, 1H), 7.73 (d, J = 7.4 Hz, 1H), 7.66 (d, J = 7.9 Hz, 2H), 7.54 (m, 2H), 7.46 (t, J = 7.4 Hz, 1H), 7.26 (m, 2H), 7.06 (d, J = 9.6 Hz, 1H), 6.53 (s, 1H), 5.80 (m, 2H), 4.92 (m, 2H), 4.83 (m, 1H), 4.21 (m, 1H). HPLC (max plot) 95.15%; Rt (min) 5.39; MS: (ESI+) 464. |
| 21 | Brown solid: 1HNMR (400 MHz, DMSO-d6): 12.84 (m, 2H), 9.42 (m, 2H), 8.47 (s, 0.5H), 8.04 (m, 3.5H), 7.92 (d, J = 7.00 Hz, 0.5H), 7.84 (m, 2H), 7.67 (d, J = 7.80 Hz, 0.5H), 7.59 (m, 2H), 7.52 (d, J = 8.28 Hz, 1H), 7.42 (m, 2H), (7.00, 6.98) (s, 1H), 5.46 (m, 4H). HPLC (max plot) 92.13%; (254 nm) 94.31%; Rt (min) 3.64; MS: (ESI+) 478. |
| 22 | Yellow solid: 1HNMR (400 MHz, DMSO-d6): 12.69 (s, 1H), 9.29 (s, 1H), 8.97 (s, 1H), 7.99 (d, J = 7.84 Hz, 1H), 7.85 (s, 1H), 7.71 (d, J = 9.60 Hz, 1H), 7.50 (d, J = 7.56 Hz, 1H), 7.38 (t, J = 8.56 Hz, 1H), 7.17 (s, 1H), 6.91 (d, J = 9.53 Hz, 1H), 5.46 (m, 2H), 4.92 (m, 2H), 4.68 (m, 2H), 3.89 (s, 3H), 3.75 (s, 3H). HPLC (max plot) 98.02%; (254 nm) 97.22%; Rt (min) 3.06; MS: (ESI+) 498.2. |
| 23 | Off white solid: 1HNMR (400 MHz, DMSO-d6): 12.66 (s, 1H), 9.42 (s, 2H), 7.99 (M, 6H), 7.83 (d, J = 7.72 Hz, 1H), 7.70 (d, J = 7.68 Hz, 0.5H), 7.64 (d, J = 7.40 Hz, 0.5H), 7.56 (d, J = 6.92 Hz, 1H), 7.43 (m, 3H), 7.21 (d, J = 8.20, 0.5 H), 7.11 (d, J = 8.16 Hz, 0.5 H), 6.99 (d, J = 9.64 Hz, 1H), 5.40 (m, 4H), 3.15 (m, 1H), 3.05 (m, 2H), 2.94 (m, 1H). HPLC (max plot) 99.8%; (254 nm) 99.64%; Rt (min) 2.96; MS: (ESI+) 477.2. |
| 24 | Off white solid: 1HNMR (400 MHz, DMSO-d6): 12.66 (s, 1H), 9.49 (s, 1H), 9.44 (s, 1H), 8.03 (m, 3H), 7.82 (d, J = 8.08 Hz, 1H), 7.61 (d, J = 7.60 Hz, 1H), 7.54 (d, J = 7.44 Hz, 1H), 7.46 (d, J = 7.76 Hz, 1H), 7.40 (m, 2H), 7.31 (t, J = 7.96 Hz, 1H), 7.21 (t, J = 7.96 Hz, 1H), 6.98 (d, J = 9.68 Hz, 1H), 6.42 (m, 1H), 5.45 (m, 2H), 1.83 (d, J = 6.92 Hz, 3H). HPLC (max plot) 98.66%; (254 nm) 98.43%; Rt (min) 4.29; MS: (ESI+) 448. |
| 25 | Off white solid: 1HNMR (400 MHz, DMSO-d6): 12.59 (s, 1H), 9.42 (s, 2H), 7.99 (m, 5H), 7.68, 7.64 (d, J = 7.0, 7.6 Hz, 1H), 7.55 (d, J = 7.28 Hz, 1H), 7.41 (, 3H), 7.15, 7.12 (d, J = 8.20, 7.04 Hz, 1H), 6.98 (d, J = 9.92 Hz, 1H), 5.38 (s, 2H), 3.22 (m, 1H), 3.06 (m, 3H), 2.86 (t, J = 7.24 Hz, 1H), 2.74 (t, J = 7.52 Hz, 1H), 1.81, 1.77 (s, 3H). HPLC (max plot) 95.8%; (254 nm) 96.47%; Rt (min) 3.44; MS: (ESI+) 519. |
| 26 | Off white solid: 1HNMR (400 MHz, DMSO-d6): 12.61(s, 1H), 9.22 (s, 1H), 9.03 (s, 1H), 8.01 (d, J = 7.84 Hz, 1H), 7.77 (s, 1H), 7.71 (d, J = 7.48 Hz, 1H), 7.52 (d, J = 7.36 Hz, 2H), 7.41 (t, J = 7.52 Hz, 1H), 7.26 (m, 2H), 6.74 (s, 1H), 5.27 (m, 2H), 4.90 (m, 2H), 4.73 (m, 2H), 2.28 (s, 3H). HPLC (max plot) 98.66%; (254 nm) 98.83%; Rt (min) 3.47; MS: (ESI+) 452. |
| 27 | Brown solid: 1HNMR (400 MHz, DMSO-d6): 12.63 (s, 1H), 9.42 (s, 2H), 8.04 (s, 1H), 8.01 (d, J = 7.76 Hz, 1H), 7.92 (d, J = 8.20 Hz, 1H), 7.88 (s, 1H), 7.83 (d, J = 7.48 Hz, 1H), 7.63 (t, J = 8.52 Hz, 1H), 7.56 (d, J = 7.84 Hz, 1H), 7.44 (m, 3H), 7.24 (d, J = 8.44 Hz, 0.5H), 7.17 (d, J = 7.64 Hz, 0.5H), 6.99 (d, J = 9.72 Hz, 1H), 5.40 (s, 2H), 3.62 (s, 2H), 3.60 (m, 2H), 3.50 (m, 2H), 2.95 (m, 2H), 2.41 (m, 2H), 2.32 (m, 1H). HPLC (max plot) 90.47%; (254 nm) 90.32%; Rt (min) 3.11; MS: (ESI+) 533.3. |
| 28 | Off white solid:1HNMR (400 MHz, DMSO-d6): 12.61 (s, 1H), 8.82 (s, 1H), 7.94 (d, J = 7.52 Hz, 1H), 7.68 (d, J = 7.76 Hz, 1H), 7.57 (d, J = 9.64 Hz, 1H), 7.49 (t, J = 6.64 Hz, 2H), 7.35 (t, J = 7.36 Hz, 1H), 7.26 (m, 2H), 6.89 (d, J = 9.52 Hz, 1H), 5.69 (m, 1H), 4.96 (m, 1H), 4.87 (m, 1H), 4.69 (m, 2H), 4.15 (m, 1H), 2.74 (s, 3H), 1.97 (s, 3H). HPLC (max plot) 99.2%; (254 nm) 98.64%; Rt (min) 3.14; MS: (ESI+) 466 |
| 29 | Off white solid: 1HNMR (400 MHz, DMSO-d6): 12.55 (br s, 1H), 9.41 (s, 2H), 8.01 (t, J = 8.40 Hz, 2H), 7.88 (d, J = 8.80 Hz, 0.5H), 7.82 (d, J = 7.48 Hz, 1H), 7.68 (d, J = 7.52 Hz, 0.5H), 7.62 (m, 1H), 7.55 (d, J = 7.24 Hz, 0.5H), 7.41 (m, 2H), 7.55 (d, J = 7.24 Hz, 0.5H), 7.34 (m, 0.5H), 7.08 (m, 0.5 H), 6.98 (d, J = 9.68 Hz, 1H), 6.91 (d, J = 8.60 Hz, 0.5H), 6.81 (d, J = 8.60 Hz, 0.5H), 5.37 (m, 4H), (3.88, 3.75) (s, 3H). HPLC (max plot) 97.82%; (254 nm) 97.91%; Rt (min) 4.64; MS: (ESI+) 464. |
| 30 | Off white solid: 1HNMR (400 MHz, DMSO-d6): 12.66 (s, 1H), 8.68 (s, 1H), 7.92 (d, J = 7.72 Hz, 1H), 7.55 (d, J = 8.12 Hz, 1H), 7.49 (d, J = 7.44 Hz, 2H), 7.40 (t, J = 7.56 Hz, 1H), 7.20 (m, 2H), 6.77 (s, 1H), 5.25 (m, 2H), |

TABLE 1-continued analytical description

| Example compound | Description |
|---|---|
| | 4.96 (m, 1H), 4.65 (m, 1H), 4.44 (m, 1H), 4.34 (m, 1H), 3.99 (m, 2H), 3.32 (m, 1H), 2.06 (s, 3H), 1.95 (m, 1H). HPLC (max plot) 97.89%; (254 nm) 97.45%; Rt (min) 3.2; MS: (HI+) 446. |
| 31 | Brown gum: 1HNMR (400 MHz, DMSO-d6): 12.46 (s, 1H), 9.48 (s, 1H), 9.41 (m, 2H), 8.03 (d, J = 9.80 Hz, 1H), 7.99 (d, J = 7.80 Hz, 1H), 7.83 (d, J = 7.52 Hz, 1H), 7.57 (m, 2H), 7.41 (m, 2H), 7.31 (m, 1H), 7.23 (m, 1H), 7.00 (s, 0.5H), 6.98 (s, 0.5H), 6.68 (s, 0.5H), 6.66 (s, 0.5H), 5.32 (m, 4H). HPLC (max plot) 93.45%; (254 nm) 93.00%; Rt (min) 3.39; MS: (ESI+) 450.2 |
| 33 | Off white solid: 1HNMR (400 MHz, DMSO-d6): 12.68 (s, 1H), 9.27 (d, J = 6.08 Hz, 1H), 8.98 (d, J = 7.28 Hz, 1H), 7.98 (dd, J1 = 7.78 Hz, J2 = 1.20 Hz, 1H), 7.84 (s, 1H), 7.71 (d, J = 9.60 Hz, 1H), 7.53 (m, 3H), 7.33 (s, 0.5H), 7.10 (s, 0.5H), 6.90 (m, 2H), 5.31 (m, 2H), 4.90 (m, 2H), 4.69 (m, 2H), (3.86, 3.77) (s, 3H). HPLC (max plot) 99.28%; (254 nm) 99.39%; Rt (min) 3.31; MS: (ESI+) 468. |
| 34 | Off white solid: 1HNMR (400 MHz, DMSO-d6): 8.96 (s, 1H), 8.18 (d, J = 7.63 Hz, 1H), 7.67 (d, J = 7.40 Hz, 1H), 7.56 (m, 2H), 7.50 (m, 1H), 721 (m, 3H), 6.94 (d, J = 9.76 Hz, 1H), 5.83 (d, J = 13.5 Hz, 1H), 5.26 (m, 2H), 4.81 (dd, J = 10.88, 4.12 Hz, 1H), 4.62 (d, J = 13.44 Hz, 1H), 4.24 (m, 1H), 4.02 (m, 1H). HPLC (max plot) 97.16%; (254 nm) 97.59%; Rt (min) 2.79; MS: (ESI+) 414.2. |
| 35 | Yellow solid: 1HNMR (400 MHz, DMSO-d6): 12.55 (s, 1H), 8.69 (s, 1H), 7.93 (dd, J1 = 7.76 Hz, J2 = 1.32 Hz, 1H), 7.43 (m, 3H), 7.17 (m, 2H), 6.92 (d, J = 9.72 Hz, 1H), 6.85 (d, J = 8.80 Hz, 0.5H), 6.79 (d, J = 8.68 Hz, 0.5H), 5.31 (m, 1H), 5.23 (m, 1H), 4.96 (m, 1H), 4.66 (m, 1H), 4.39 (m, 2H), 3.93 (m, 2H), (3.79, 3.76) (s, 3H), 2.28 (m, 1H), 1.95 (m, 1H). HPLC (max plot) 94.18%; (254 nm) 92.08%; Rt (min) 2.99; MS: (ESI+) 462. |
| 37 | Off white solid: 1HNMR (400 MHz, DMSO-d6): 12.79 (s, 1H), 9.10 (s, 1H), 8.44 (s, 1H), 8.02 (d, J = 7.72 Hz, 1H), (7.93, 7.90) (s, 1H), 7.68 (dd, J1 = 8.54 Hz, J2 = 2.20 Hz, 1H), 7.60 (d, J = 7.84 Hz, 1H), 7.54 (m, 2H), 7.45 (t, J = 7.56 Hz, 1H), 7.32 (t, J = 7.68 Hz, 1H), 7.25 (t, J = 7.64 Hz, 1H), 7.07 (t, J = 8.60 Hz, 1H), 7.01 (t, J = 9.68 Hz, 1H), 5.36 (s, 2H), 4.62 (t, J = 7.88 Hz, 2H), 3.85 (s, 3H), 3.04 (t, J = 7.80 Hz, 2H). HPLC (max plot) 96.83%; (254 nm) 96.59%; Rt (min) 4.49; MS: (ESI+) 477.8. |
| 38 | Brown solid: 1HNMR (400 MHz, DMSO-d6): 12.79 (s, 1H), 9.91 (s, 1H), 9.08 (s, 1H), 8.37 (s, 1H), 8.01 (m, 1H), 7.85, 7.83 (s, 1H), 7.63 (d, J = 7.76 Hz, 1H), 7.54 (t, J = 6.20 Hz, 2H), 7.49 (dd, J1 = 8.44 Hz, J2 = 2.24 Hz, 1H), 7.44 (t, J = 7.52 Hz, 1H), 7.31 (m, 1H), 7.26(m, 1H), 6.99, 6.97 (s, 1H), 6.89 (d, J = 9.36 Hz, 1H), 5.35 (s, 2H), 4.60 (t, J = 8.08 Hz, 2H), 3.01 (t, J = 7.84 Hz, 2H). HPLC (max plot) 97.8%; (254 nm) 98.67%; Rt (min) 3.79; MS: (ESI+) 464. |
| 39 | Off white solid: 1HNMR (400 MHz, DMSO-d6): 12.71 (s, 1H), 7.98 (m, 3H), 7.80 (d, J = 7.84 Hz, 1H), 7.64 (d, J = 7.76 Hz, 1H), 7.55 (d, J = 7.52 Hz, 1H), 7.47 (d, J = 7.60 Hz, 1H), 7.41 (m, 2H), 7.29 (t, J = 8.64 Hz, 1H), 7.19 (t, J = 8.12 Hz, 1H), 5.39 (s, 4H), 2.11 (s, 3H). HPLC (max plot) 98.97%; (254 nm) 98.97%; Rt (min) 4.37; MS: (ESI+) 448. |
| 40 | Off white solid: 1HNMR (400 MHz, DMSO-d6): 12.53 (s, 1H), 8.69 (s, 1H), 7.92 (d, J = 7.80 Hz, 1H), 7.48 (d, J = 7.72 Hz, 1H), 7.38 (d, J = 7.68 Hz, 1H), 7.24(s, 1H), 7.20 (d, J = 9.76 Hz, 1H), 7.15 (s, 1H), 6.91 (d, J = 9.72 Hz, 1H), 5.31 (d, J = 13.8 Hz, 1H), 5.24 (d, J = 5.32 Hz, 1H), 4.95 (d, J = 13.96 Hz, 1H), 4.67 (m, 1H), 4.40 (m, 2H), 3.93 (d, J = 9.76 Hz, 2H), 3.80 (s, 3H), 3.75 (s, 3H), 2.26 (m, 1H), 1.95 (m, 1H). HPLC (max plot) 99.37%; (254 nm) 98.94%; Rt (min) 2.71; MS: (ESI+) 492. |
| 41 | Off white solid: 1HNMR (400 MHz, DMSO-d6): 12.62 (s, 1H), 9.54 (s, 1H), 9.46 (s, 1H), 8.18 (d, J = 8.20 Hz, 1H), 8.01 (d, J = 7.76 Hz, 1H), 7.93 (d, J = 9.72 Hz, 1H), 7.81 (dd, J1 = 8.34 Hz, J2 = 2.16 Hz, 1H), 7.57 (d, J = 7.88 Hz, 1H), 7.43 (m, 2H), 7.38 (d, J = 8.24 Hz, 1H), 7.31 (t, J = 7.20 Hz, 1H), 7.20 (t, J = 7.04 Hz, 1H), (6.97, 6.95) (s, 1H), 5.41 (s, 2H), 3.90 (s, 4H), 3.31 (m, 4H), 3.05 (m, 2H). HPLC (max plot) 97.84%; (254 nm) 97.94%; Rt (min) 4.11; MS: (ES1+) 519. |

Example 43

IRAK1 and IRAK4 Enzymatic Assays

IRAK1 Enzymatic Assay:

IRAK1 is a human purified recombinant enzyme (His-TEV-IRAK1 (194-712)) In this assay, IRAK-1 hydrolyses ATP and autophosphorylates.

Measurement of IRAK-1 inhibition is performed in streptavidin coated 384 well FlashPlate (PerkinElmer #SMP410A).

His-TEV-IRAK-1 (15 ng/well), ATP (1 μM, [$^{33}$P]ATP 0.25 μCi/well) and compounds in DMSO (range of concentrations from 20 μM to 1 nM) or controls (2% DMSO) are incubated for 3 hours at 30° C. in assay buffer: Hepes pH7.0 50 mM, Fatty acid-free BSA 0.1%, Dithiothreitol DTT 2 mM, MgCl2 10 mM, EGTA 0.5 mM, Triton-X-100 0.01%. Kinase reaction is stopped by addition of EDTA. Supernatant is discarded, plates are washed three times with 150 mM NaCl and radioactivity is then measured in a Microbeta Trilux reader.

IRAK4 Enzymatic Assay:

IRAK4 is a human purified recombinant enzyme (His-TEV-IRAK1 (194-712) IRAK4 hydrolyses ATP, autophosphorylates and phosphorylates a Serine/Threonine generic peptidic substrate (STK: 61ST1BLC from CisBio International based in Bagnols/Cèze FR).

Measurement of IRAK-4 inhibition is performed in streptavidin coated 384 well FlashPlate (PerkinElmer #SMP410A). His-TEV-IRAK4 (20 ng/well), ATP (2 μM, [$^{33}$P]ATP 0.25 μCi/well), STK1-biotin peptide (300 nM) and compounds in DMSO (range of concentrations from 20 μM to 1 nM) or controls (2% DMSO) are incubated for 3 hours at 30° C. in assay buffer: Hepes pH7.0 50 mM, Fatty acid-free BSA 0.1%, Dithiothreitol DTT 2 mM, MgCl2 10 mM, EGTA 0.5 mM, Tween-20 0.01%, MnCl2 5 mM.

Kinase reaction is stopped by addition of EDTA. Supernatant is discarded, plates are washed three times with 150 mM NaCl and radioactivity is then measured in a Microbeta Trilux reader.

The results are displayed on p. 10ff.

Example 44

Cellular Assay

TLR7 Induced IL-6 in Human PBMC's

Human PBMC assay is used as one of the functional assay to monitor the activity of IRAK1 and IRAK4 small molecule inhibitors on TLR7 induced IL-6 secretion in human mononuclear cells (PBMC's). Human PBMCs are prepared from buffy coats (whole blood enriched with leukocytes and platelets) obtained from healthy volunteers used either fresh or frozen are plated in assay media (RPMI+2% P/S/L-glu+10% HI-FBS) and pre-treated with compounds in DMSO/media (range of concentrations from 25 uM to 0.4 nM) or controls (0.25% DMSO) for 30 minutes at 37° C. in assay media. Following pre-treatment with IRAK1 and IRAK4 inhibitors, PBMC's are stimulated with TLR7 specific ligand (2 uM) overnight (16-18 hrs) at 37° C. After incubation supernatant is transferred to 384 well PE AlphaPlate-384 (6005350) and IL-6 is quantified using Perkin Elmer IL-6 Alpha LISA kit (AL223C). Plates are read on an Envision® plate reader with Alpha Technology®.

Following results are obtained:

| Compound No. | Structure | IC$_{50}$ PBMC |
|---|---|---|
| 1 | 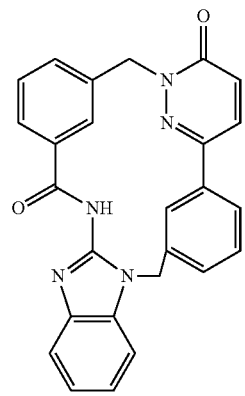 [SMILES: O=C1Nc2nc3ccccc3n2Cc2cccc(c2)-c2ccc(=O)n(n2)Cc2cccc1c2] | ** |
| 2 | 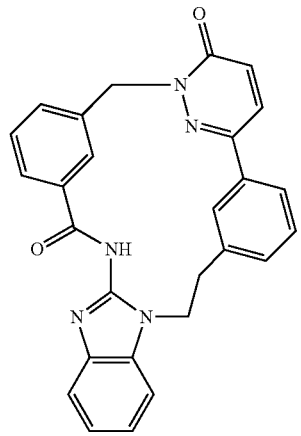 [SMILES: O=C1Nc2nc3ccccc3n2CCc2cccc(c2)-c2ccc(=O)n(n2)Cc2cccc1c2] | ** |
| 5 | 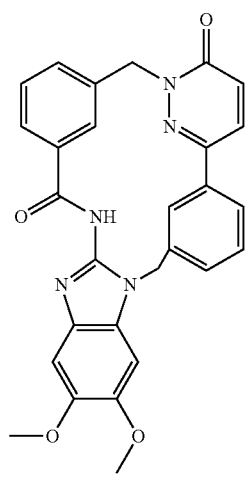 [SMILES: COc1cc2nc3n(c2cc1OC)Cc1cccc(c1)-c1ccc(=O)n(n1)Cc1cccc(c1)C(=O)N3] | *** |
| 7 | 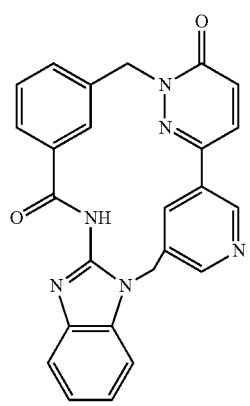 [SMILES: O=C1Nc2nc3ccccc3n2Cc2cncc(c2)-c2ccc(=O)n(n2)Cc2cccc1c2] | *** |

| Compound No. | Structure | IC$_{50}$ PBMC |
|---|---|---|
| 8 | 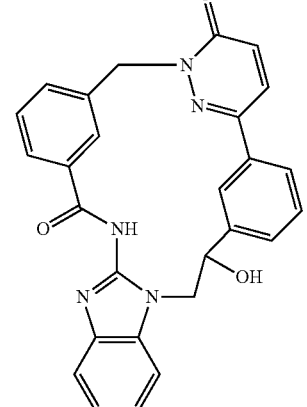 | ** |
| 12 | | * |
| 14 | | ** |
| 16 | | *** |
| Compound No. | Structure | IC$_{50}$ PBMC |
|---|---|---|
| 17 | 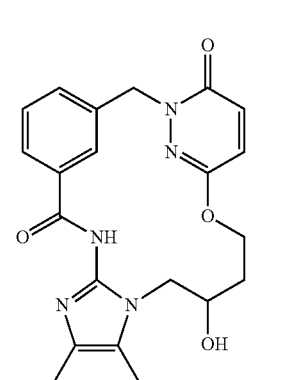 | *** |
| 18 | | ** |
| 20 | | *** |

-continued

| Compound No. | Structure | IC$_{50}$ PBMC |
|---|---|---|
| 21 | 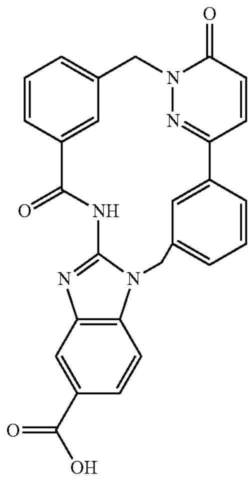 [SMILES: O=C(O)c1ccc2c(c1)nc1n2Cc2cccc(c2)-c2ccc(=O)n(n2)Cc2cccc(c2)C(=O)N1] | ** |
| 25 | 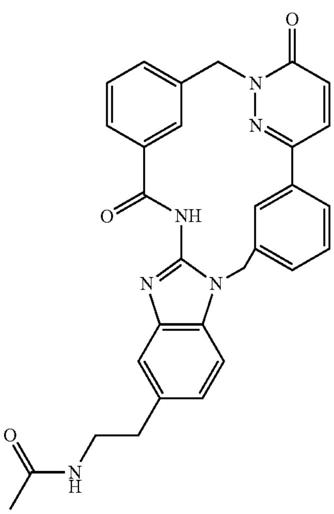 [SMILES: CC(=O)NCCc1ccc2c(c1)nc1n2Cc2cccc(c2)-c2ccc(=O)n(n2)Cc2cccc(c2)C(=O)N1] | *** |
| 32a | 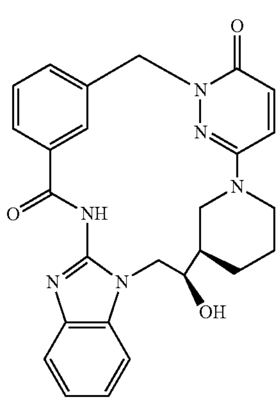 [SMILES: O=C1Nc2nc3ccccc3n2C[C@H](O)[C@@H]2CCCN(C2)c2ccc(=O)n(n2)Cc2cccc1c2] | ** |

-continued

| Compound No. | Structure | IC$_{50}$ PBMC |
|---|---|---|
| 32b | 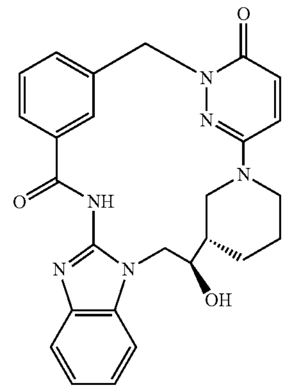 [SMILES: O=C1Nc2nc3ccccc3n2C[C@H](O)[C@H]2CCCN(C2)c2ccc(=O)n(n2)Cc2cccc1c2] | ** |

Example 45

Preparation of a Pharmaceutical Formulation

Formulation 1—Tablets

A compound of formula (I) is admixed as a dry powder with a dry gelatin binder in an approximate 1:2 weight ratio. A minor amount of magnesium stearate is added as a lubricant. The mixture is formed into 240-270 mg tablets (80-90 mg of active compound according to the invention per tablet) in a tablet press.

Formulation 2—Capsules

A compound of formula (I) is admixed as a dry powder with a starch diluent in an approximate 1:1 weight ratio. The mixture is filled into 250 mg capsules (125 mg of active compound according to the invention per capsule).

Formulation 3—Liquid

A compound of formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of formula (I) is admixed as a dry powder with a dry gelatin binder in an approximate 1:2 weight ratio. A minor amount of magnesium stearate is added as a lubricant. The mixture is formed into 450-900 mg tablets (150-300 mg of active compound according to the invention) in a tablet press.

Formulation 5—Injection

A compound of formula (I) is dissolved in a buffered sterile saline injectable aqueous medium to a concentration of approximately 5 mg/mL.

The invention claimed is:

1. A compound of formula (I):

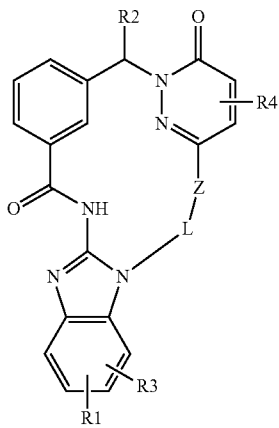

wherein
R1, R3 denote each, independently of one another H, (CH$_2$)$_p$CON(R5)$_2$, OA, Hal, COOH, COOA, (CH$_2$)$_p$NHCOA, (CH$_2$)$_p$Het1, (CH$_2$)$_p$NR2R5, or OH;
R2 denotes H or linear or branched alkyl with 1, 2 or 3 C atoms, wherein one or two H atoms of the alkyl group are optionally replaced by OR6, NR5R6, NHCOR5, CONR5R6;
R4 denotes H or A;
R5 denotes H or linear or branched alkyl with 1, 2 or 3 C atoms;
R6 denotes H or linear or branched alkyl with 1, 2 or 3 C atoms;
Z is absent or denotes Ar-diyl or Het-diyl;
L denotes (CH$_2$)$_n$ wherein one or two CH$_2$ groups are optionally replaced by O and/or a CH=CH-group, and/or wherein one or two H atoms are optionally replaced by OR2, NR2R5 or Het1;
Ar-diyl denotes 1,2-, 1,3- or 1,4-phenylen optionally substituted with from 1 to 5 groups independently selected from the group consisting of Hal, CN, —CF$_3$, —OCF$_3$, OH, O-A, SO$_2$-A, COOH, COOA, —CO-A, O-phenyl, SO$_2$-phenyl, SO$_2$—CF$_3$, Het2 and A;
Het-diyl denotes an unsaturated, saturated or aromatic 5- or 6-membered heterocycle having 1 to 2 N, O and/or S atoms, which are optionally unsubstituted or mono-, di- or trisubstituted by Hal, CN, —CF$_3$, —OCF$_3$, O-A, SO$_2$-A, COOH, COOA, —CO-A, O-phenyl, SO$_2$-phenyl, SO$_2$—CF$_3$, Het2 and/or A;
A denotes an unbranched or branched alkyl having 1 to 10 C atoms, in which 1 to 5 H atoms are optionally replaced by F and/or in which one or two non-adjacent CH$_2$ groups are optionally replaced by O;
Het1 denotes morpholinyl, piperidinyl or pyrrolidinyl;
Het2 denotes morpholinyl, piperidinyl or pyrrolidinyl;
Hal denotes F, Cl, Br, I;
n denotes 1, 2, 3, 4, 5 or 6;
p denotes 0, 1 or 2
or a pharmaceutically acceptable salt thereof.

2. The compound of claim 1, wherein R4 is H or methyl.

3. The compound of claim 1, wherein Het-diyl denotes pyridine-diyl, pyrimidine-diyl, pyridazin-diyl, pyrazol-diyl, imidazol-diyl, piperidin-diyl or pyrrolidin-diyl, each of which is unsubstituted or disubstituted by A.

4. The compound of claim 1, wherein Z is 1,3-phenylen, which is unsubstituted or monosubstituted by A, Hal, OH, or OA.

5. A compound selected from the group consisting of:

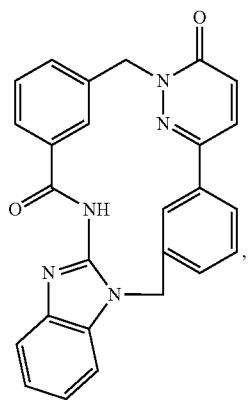

1

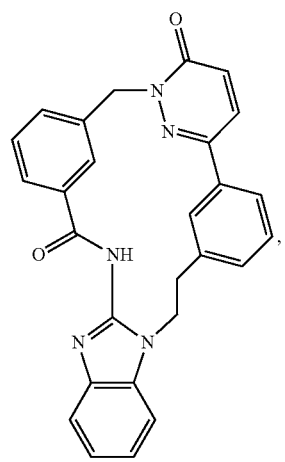

2

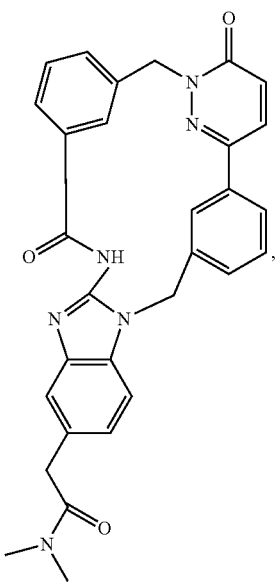

3a

113
-continued
4
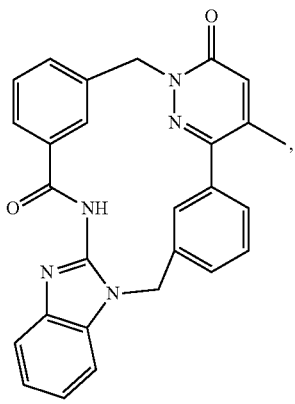
3b
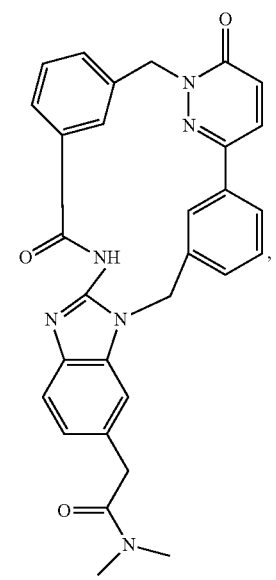
5
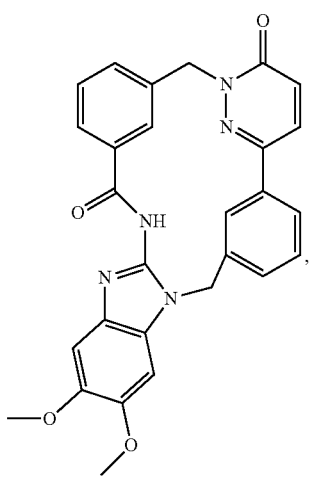
114
-continued
6
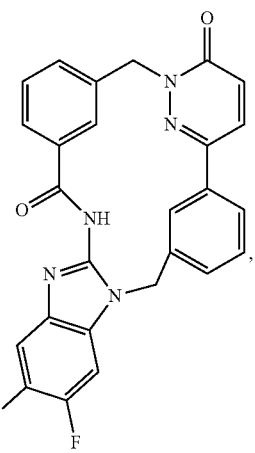
7
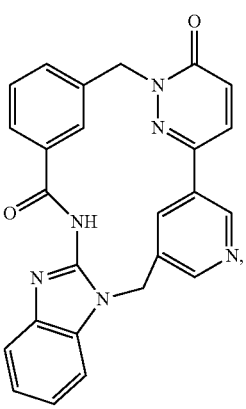
8

-continued
9
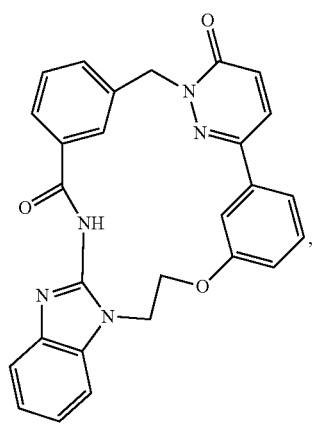
10
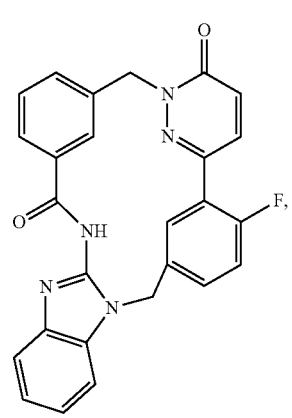
11
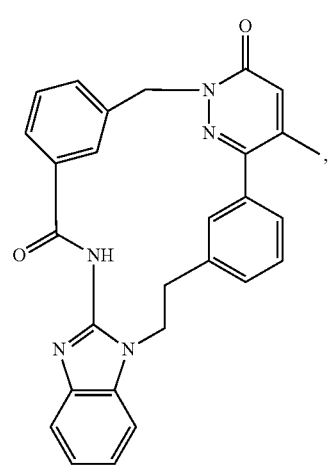
-continued
12
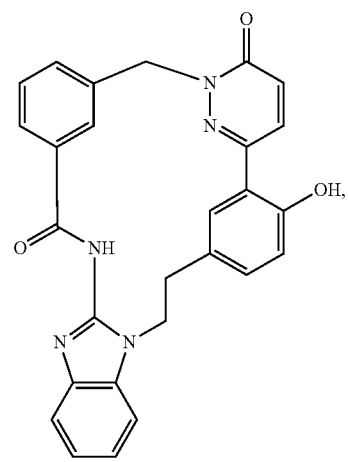
13
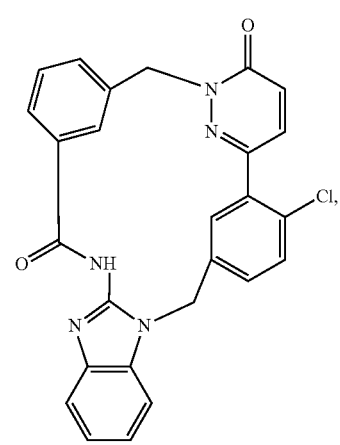
14
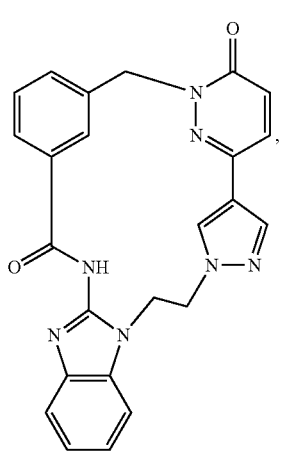

117
-continued
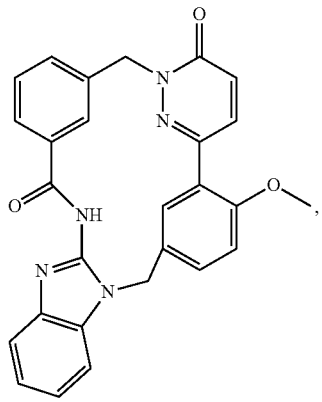
15
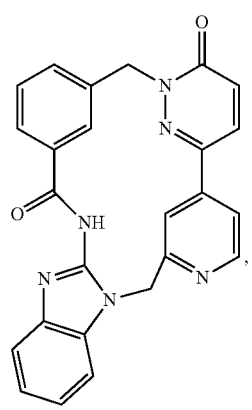
16
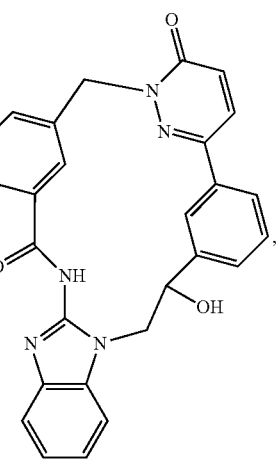
17
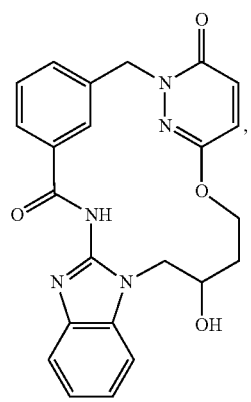
18
118
-continued
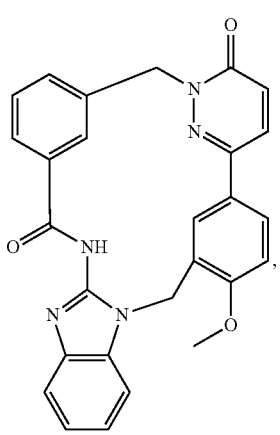
19
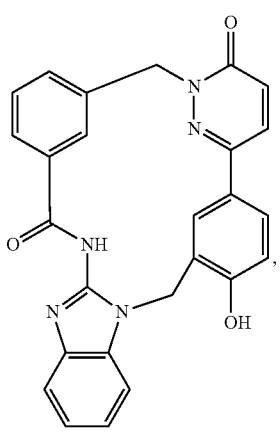
20
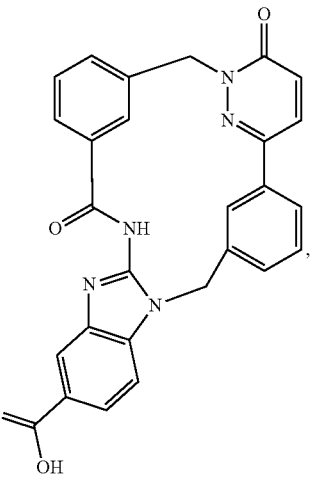
21

119
-continued
22
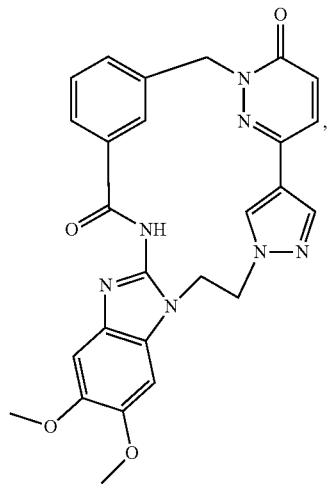
23
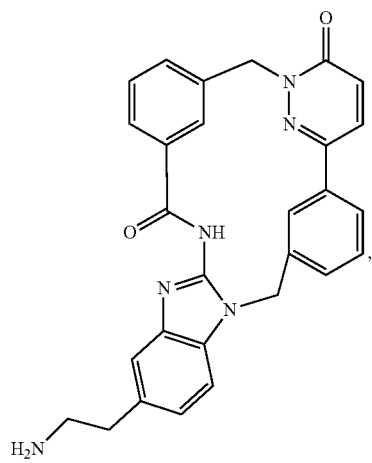
24
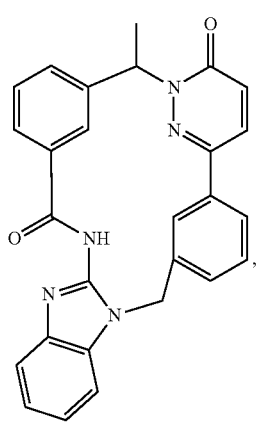
120
-continued
25
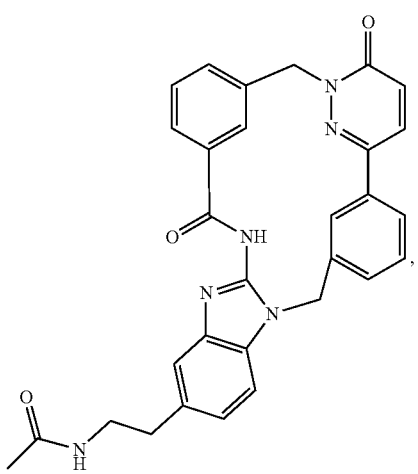
26
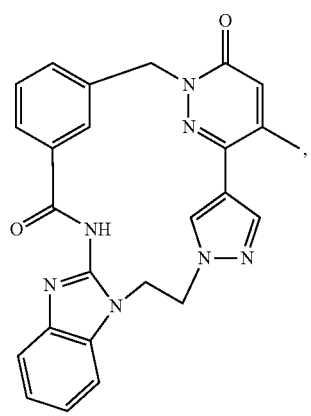
27
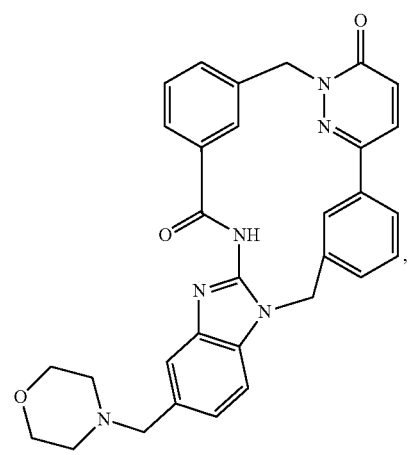

-continued
28
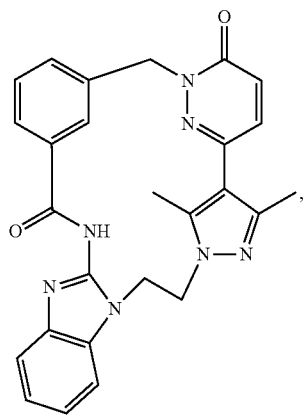
29
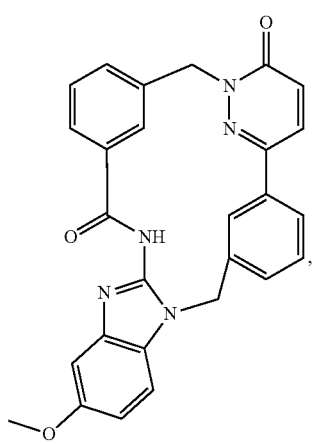
30
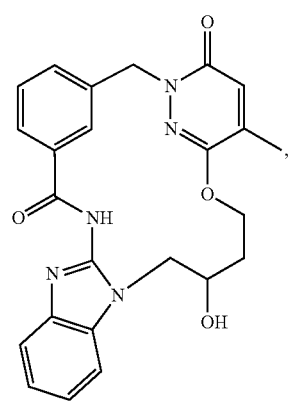
-continued
31
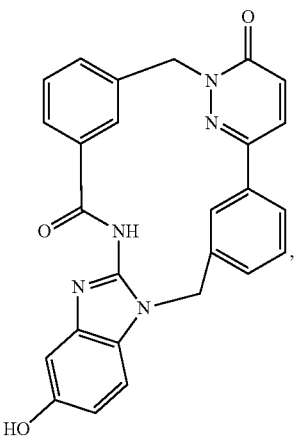
32a
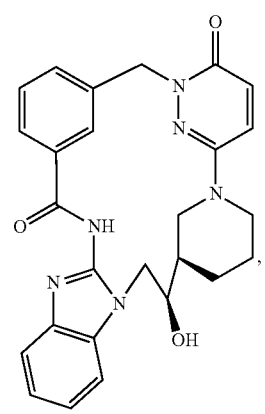
32b
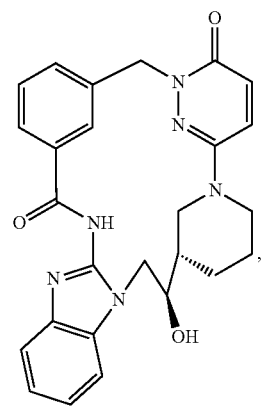

33
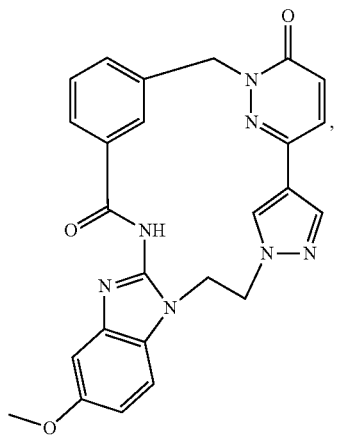
34
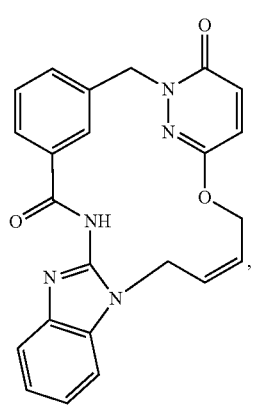
35
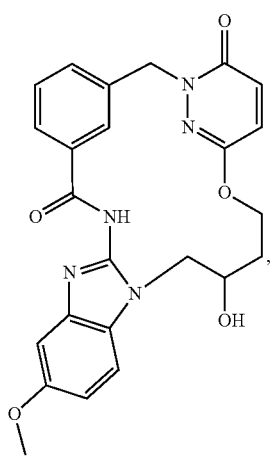
36a
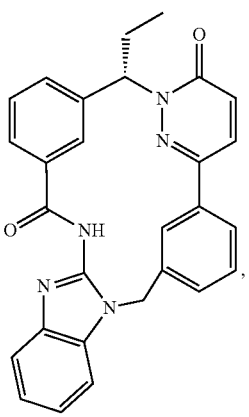
36b
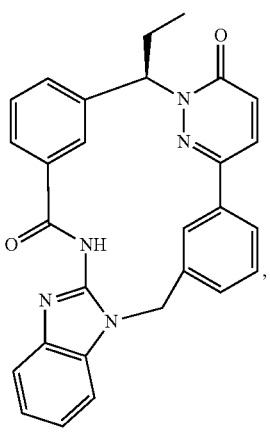
37
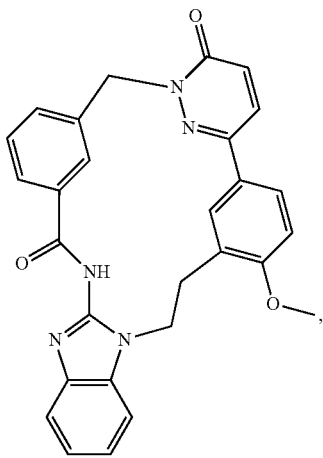

38
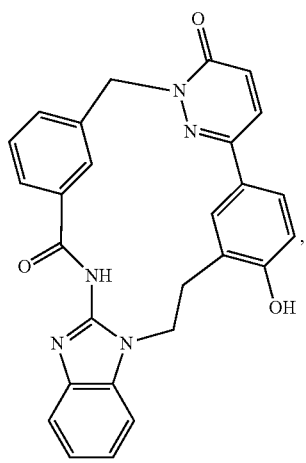

39
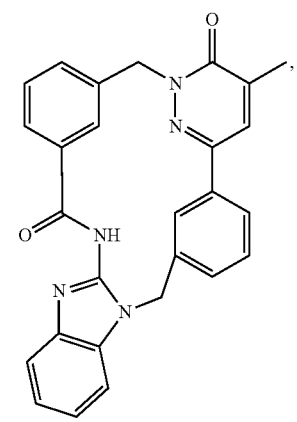

40
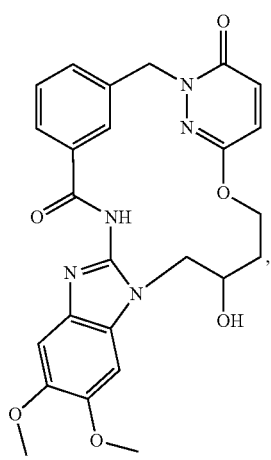

41
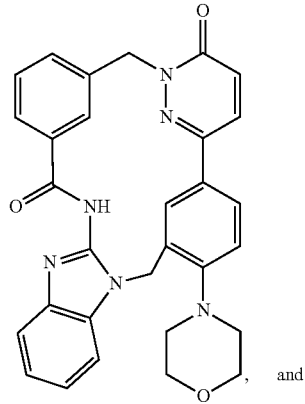

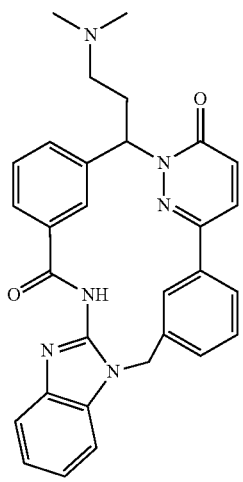

or a pharmaceutically acceptable salt thereof.

6. A pharmaceutical composition, comprising: the compound of claim 1 and at least one pharmaceutically acceptable carrier or excipient.

7. A kit consisting of separate packs of:
   (a) an effective amount of the compound of claim 1, and
   (b) an effective amount of a further medicament active ingredient.

8. The pharmaceutical composition of claim 6, further comprising: a medicament effective for treatment of an inflammatory disease or an immune disorder.

9. The pharmaceutical composition of claim 8, further comprising an immunomodulating agent.

10. A process for synthesizing the compound of claim 1, the process comprising:
   macrocyclizing a compound of formula (II) to obtain the compound of claim 1, wherein R1, R2, R3, R4, Z and L are the same as in claim 1 and A1 is H, Li, Na or K:

127
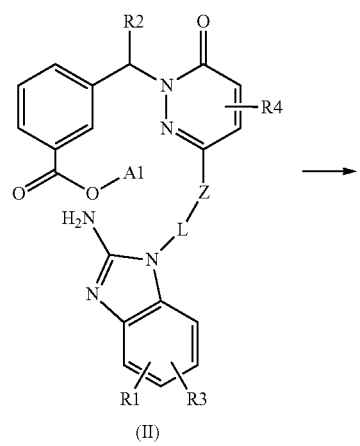
(II)
128
-continued
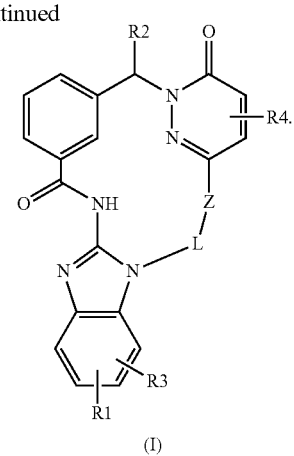
(I)
* * * * *